US008008010B1

(12) United States Patent
Kuersten et al.

(10) Patent No.: US 8,008,010 B1
(45) Date of Patent: Aug. 30, 2011

(54) CHIMERIC OLIGONUCLEOTIDES FOR LIGATION-ENHANCED NUCLEIC ACID DETECTION, METHODS AND COMPOSITIONS THEREFOR

(75) Inventors: R. Scott Kuersten, Austin, TX (US); Brittan L. Pasloske, Austin, TX (US)

(73) Assignee: Applied Biosystems, LLC, Carlsbad, CA (US)

( * ) Notice: Subject to any disclaimer, the term of this patent is extended or adjusted under 35 U.S.C. 154(b) by 123 days.

(21) Appl. No.: 12/147,847

(22) Filed: Jun. 27, 2008

Related U.S. Application Data

(60) Provisional application No. 60/946,624, filed on Jun. 27, 2007.

(51) Int. Cl.
*C12Q 1/68* (2006.01)
*C07H 21/02* (2006.01)
*C07H 21/04* (2006.01)

(52) U.S. Cl. ............................ 435/6; 536/23.1; 536/24.3

(58) Field of Classification Search ...... 435/6; 536/23.1, 536/24.3
See application file for complete search history.

(56) References Cited

U.S. PATENT DOCUMENTS

| | | | |
|---|---|---|---|
| 4,988,617 A | 1/1991 | Landegren et al. | |
| 5,185,243 A | 2/1993 | Ullman et al. | |
| 5,476,930 A | 12/1995 | Letsinger et al. | |
| 5,494,810 A * | 2/1996 | Barany et al. | 435/91.52 |
| 5,514,543 A | 5/1996 | Grossman et al. | |
| 5,681,943 A | 10/1997 | Letsinger et al. | |
| 5,807,674 A | 9/1998 | Tyagi | |
| 6,004,826 A | 12/1999 | Segev | |
| 6,030,787 A * | 2/2000 | Livak et al. | 435/6 |
| 6,130,073 A | 10/2000 | Eggerding | |
| 6,297,016 B1 | 10/2001 | Egholm et al. | |
| 6,469,151 B1 | 10/2002 | Egholm et al. | |
| 6,511,810 B2 | 1/2003 | Bi et al. | |
| 6,797,470 B2 | 9/2004 | Barany et al. | |
| 6,849,255 B2 * | 2/2005 | Gazit et al. | 424/93.21 |
| 7,129,050 B2 | 10/2006 | Grossman et al. | |
| 7,153,658 B2 | 12/2006 | Andersen et al. | |
| 2003/0077609 A1 | 4/2003 | Jakobsen et al. | |
| 2003/0119004 A1 | 6/2003 | Wenz et al. | |
| 2003/0143599 A1* | 7/2003 | Makarov et al. | 435/6 |
| 2004/0106112 A1 | 6/2004 | Nilsson et al. | |
| 2004/0175733 A1 | 9/2004 | Andersen et al. | |
| 2004/0219565 A1 | 11/2004 | Kauppinen et al. | |
| 2004/0259128 A1 | 12/2004 | Kawasaki et al. | |
| 2005/0272080 A1 | 12/2005 | Palma et al. | |
| 2006/0003337 A1 | 1/2006 | Brandis et al. | |
| 2006/0019288 A1 | 1/2006 | Andersen et al. | |
| 2006/0051749 A1 | 3/2006 | Wang et al. | |
| 2006/0063163 A1 | 3/2006 | Chen et al. | |
| 2006/0078894 A1 | 4/2006 | Winkler et al. | |
| 2006/0194225 A1 | 8/2006 | Spier | |
| 2006/0281108 A1 | 12/2006 | Monforte et al. | |
| 2007/0015187 A1 | 1/2007 | Lao et al. | |
| 2007/0020644 A1 | 1/2007 | Kolykhalov et al. | |
| 2010/0087329 A1* | 4/2010 | Wang | 506/9 |

FOREIGN PATENT DOCUMENTS

| | | |
|---|---|---|
| EP | 0320308 | 11/1993 |
| EP | 0439182 | 4/1996 |
| WO | WO 90/01069 | 2/1990 |
| WO | WO 01/77383 | 10/2001 |
| WO | WO 2004/085667 | 10/2004 |

OTHER PUBLICATIONS

Fan et al., A versatile assay for high-throughput gene expression profiling on universal array matrices. Genome Research 14 : 878-885 (2004).*
Silber et al., Purification and properties of bacteriophage T4-induced RNA ligase. PNAS 69(10) : 3009-3013 (1972).*
Zhang et al., "Amplification of target-specific, ligation-dependent circular probe" Gene 1998 211: 277-285.
Abramovitz et al., "Optimization of RNA extraction from FFPE tissues for expression profiling in the DASL assay," BioTechniques Mar. 2008 44: 3 417-423.
Adler et al., "Guide RNA requirement for editing-site-specific endonucleolytic cleavage of preedited mRNA by mitochondrial ribonucleoprotein particles in *Trypanosoma brucei*," Mol. Cell. Biol. 1997 17: 5377-5385.
Bibikova et al., "Gene Expression Profiles in Formalin-Fixed, Paraffin-Embedded Tissues Obtained with a Novel Assay for Microarray Analysis," Clin Chem 2004 50: 2384-2386.
Cronin et al., "Measurement of Gene Expression in Archival Paraffin-Embedded Tissues: Development and Performance of a 92-Gene Reverse Transcriptase-Polymerase Chain Reaction Assay," Am J Pathol 2004 164: 35-42.
Freier et al., "The ups and downs of nucleic acid duplex stability: structure-stability studies on chemically-modified DNA:RNA duplexes," Nucl. Acids Res. 1997 25: 4429-4443.
Gillespie et al., "Evaluation of Non-Formalin Tissue Fixation for Molecular Profiling Studies," Am J Pathol 2002 160: 449-457.
Gumport et al., "T4 RNA Ligase as a Nucleic Acid Synthesis and Modification Reagent in Gene Amplification and Analysis," 1981 2: 313-345.
Ho et al. "Bacteriophage T4 RNA ligase 2 (gp24.1) exemplifies a family of RNA ligases found in all phylogenetic domains," PNAS 2002 99:12709-12714.
Ho et al., "Structure and Mechanism of RNA Ligase," Structure 2004 12 327-339.

(Continued)

*Primary Examiner* — E C Whisenant

(57) ABSTRACT

Ligation-enhanced nucleic acid detection assay embodiments for detection of RNA or DNA are described. The assay embodiments rely on ligation of chimeric oligonucleotide probes to generate a template for amplification and detection. The assay embodiments are substantially independent of the fidelity of a polymerase for copying compromised nucleic acid. Very little background amplification is observed and as few as 1000 copies of target nucleic acid can be detected. Method embodiments are particularly adept for detection of RNA from compromised samples such as formalin-fixed and paraffin-embedded samples. Heavily degraded and cross-linked nucleic acids of compromised samples, in which classic quantitative real time PCR assays typically fail to adequately amplify signal, can be reliably detected and quantified.

13 Claims, 31 Drawing Sheets

OTHER PUBLICATIONS

Figure 1B:
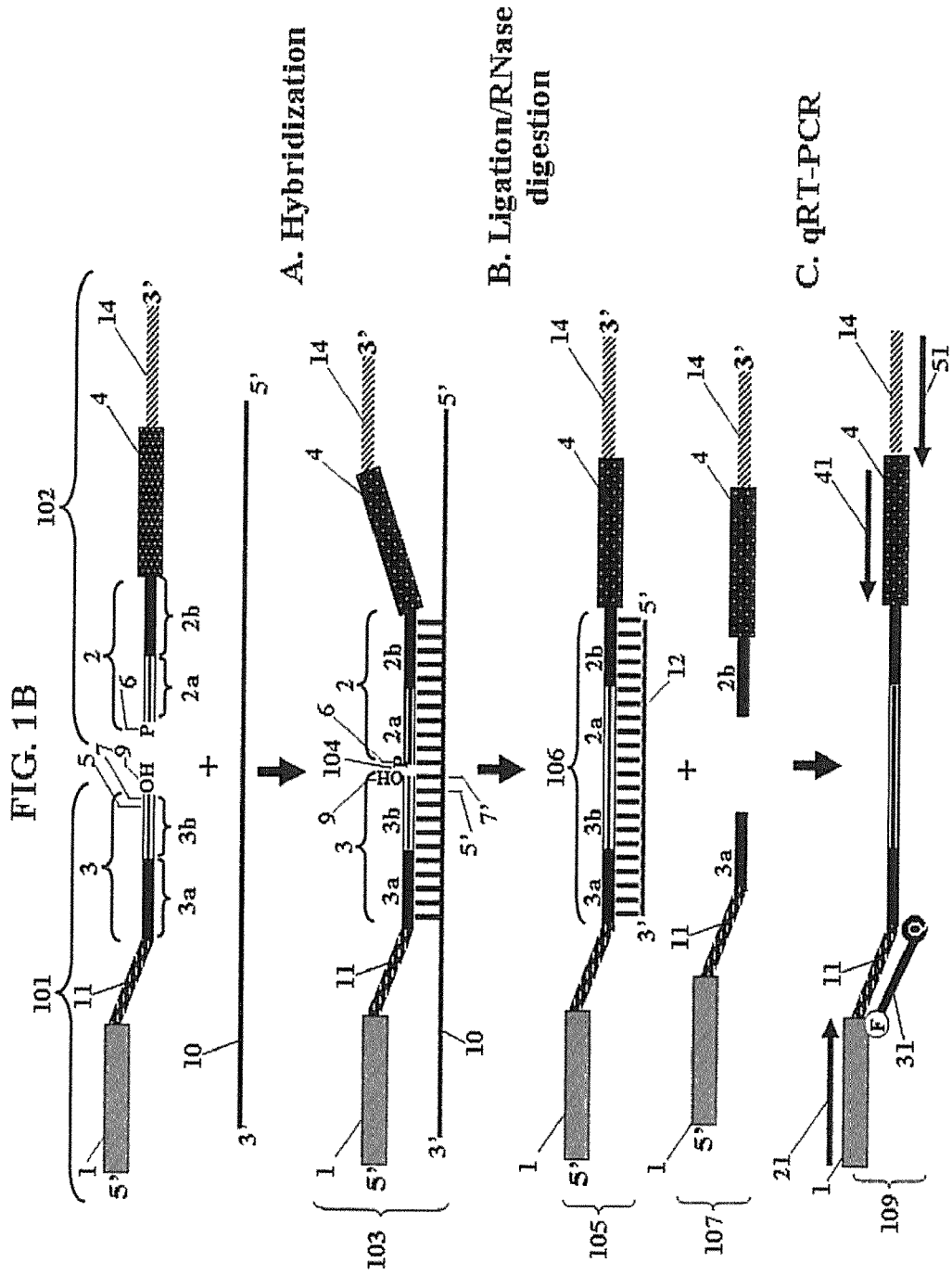

Hsuih et al., "Novel, ligation-dependent PCR assay for detection of Hepatitis C in serum," J. Clin. Microbiol. 1996 34: 501-507.

Karimi-Busheri et al. "Repair of DNA strand gaps and nicks containing 3'-phosphate and 5'- hydroxyl termini by purified mammalian enzymes," Nucl. Acids Res. 1998 26: 4395-4400.

Leong, Anthony S-Y, "Fixation and Fixatives" http://home.primus.com.au/royellis/fix.htm, pp. 1-27, Sep. 19 2003.

Masuda et al. "Analysis of chemical modification of RNA from formalin-fixed samples and optimization of molecular biology applications for such samples," Nucl. Acids Res. 1999 27: 4436-4443.

Miyauchi et al. "Further study of Hepatitis C virus RNA detection in formalin-fixed, paraffin-embedded liver tissues by ligation-dependent polymerase chain reaction," Pathology International 1998 48 428-432.

Nandakumar et al., "Dual Mechanisms whereby a Broken RNA End Assists the Catalysis of its Repair by T4 RNA Ligase 2" J. Biol. Chem. 2005 280: 23484-23489.

Nandakumar et al., "How an RNA Ligase Discriminates RNA versus DNA Damage," Molecular Cell 2004 16: 211-221.

Nandakumar et al., "RNA Substrate Specificity and Structure-guided Mutational Analysis of Bacteriophage T4 RNA Ligase 2," J. Biol. Chem. 2004 279: 31337-31347.

Nilsson et al., "Enhanced detection and distinction of RNA by enzymatic probe ligation," Nature Biotechnology 2000 18: 791-793.

Nilsson et al., "RNA-templated DNA ligation for transcript analysis," Nucl. Acids Res. 2001 29: 578-581.

Park et al., "Detection of Hepatitis C virus RNA using ligation-dependent polymerase chain reaction in formalin-fixed, paraffin-embedded liver tissues," Am J Pathol 1996 149: 1485-1491.

Raymond et al.,"*Deinococcus radiodurans*RNA ligase exemplifies a novel ligase clade with a distinctive N-terminal module that is important for 5'-PO4 nick sealing and ligase adenylylation but dispensable for phosphodiester formation at an adenylylated nick," Nucl. Acids Res. 2007 35: 839-849.

Specht et al., "Quantitative Gene Expression Analysis in Microdissected Archival Formalin-Fixed and Paraffin-Embedded Tumor Tissue" Am J Pathol 2001 158: 419-429.

Urieli-Shoval et al., "Preservation of RNA for In Situ Hybridization: Carnoy's Versus Formaldehyde Fixation," Journal of Histochemistry and Cytochemistry 1992 40:12 1879-1885.

Wood et al., "RNA Ligase: Picking Up the Pieces", Molecular Cell 2004 13(4) pp. 455-456.

Yarkin et al., "Detection of HPV DNA in Cervical Specimens Collected in Cytologic Solution by Ligation-Dependent PCR," Acta Cytologica 2003 47(3) 450-456.

Yin et al., "Structure-Function Analysis of T4 RNA Ligase 2", J. Biol. Chem, 2003 278: 17601-17608.

Yin et al., "Characterization of bacteriophage KVP40 and T4 RNA ligase 2" Virology 319(1) 2004 141-151.

Zhang et al., "Target-specific, ligation-dependent amplification of circularized probe" Cancer Detection and Prevention 1996; 20(5).

* cited by examiner

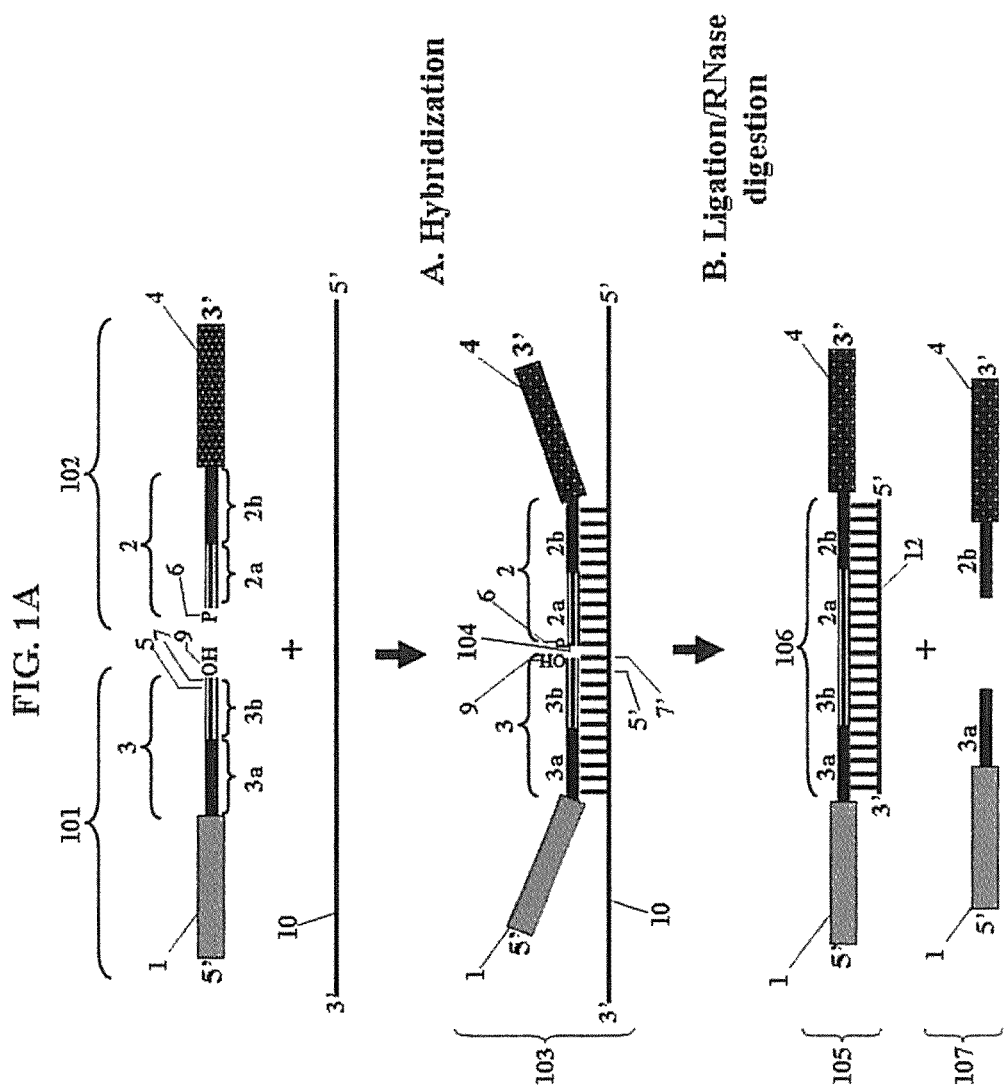

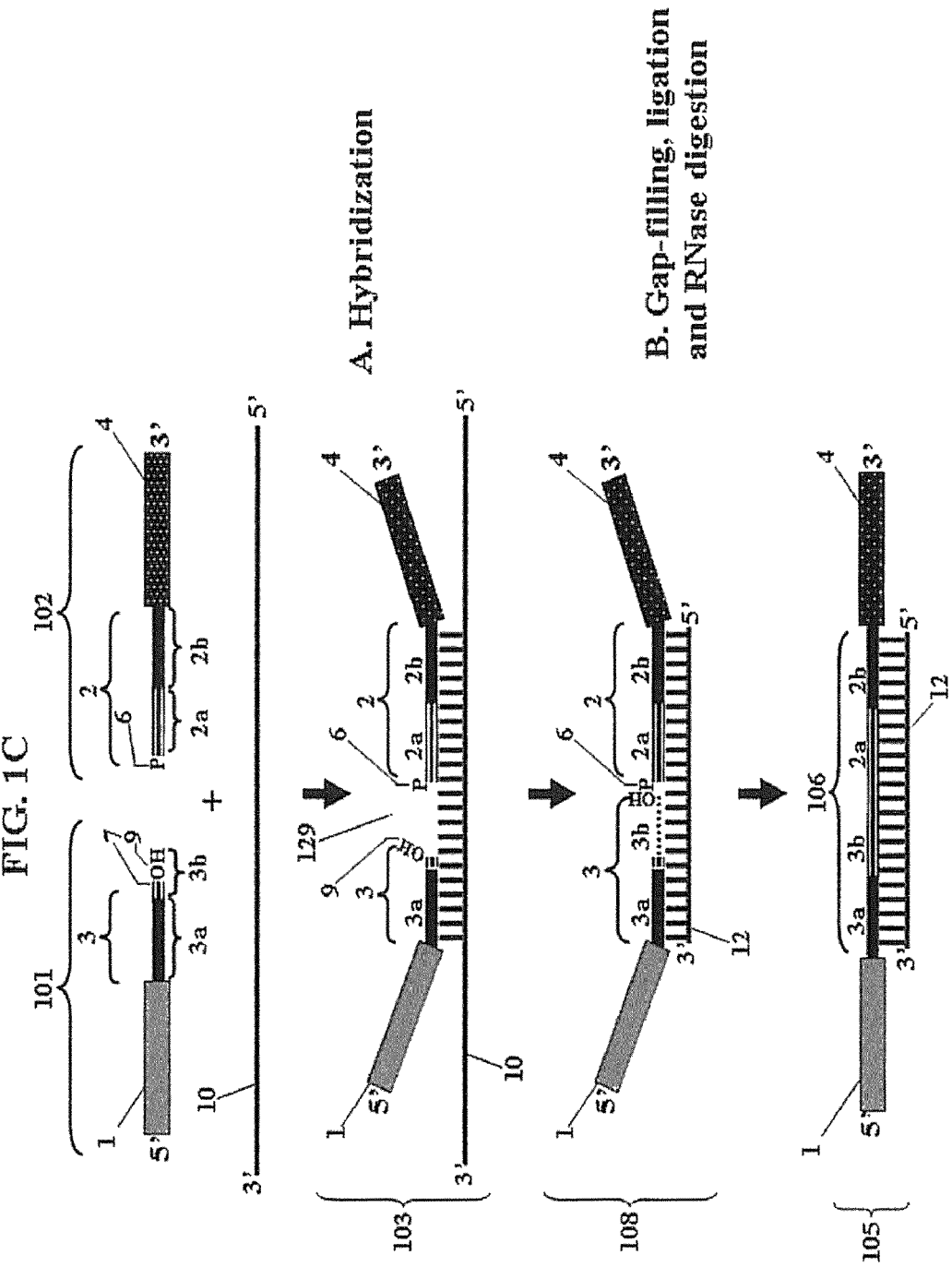

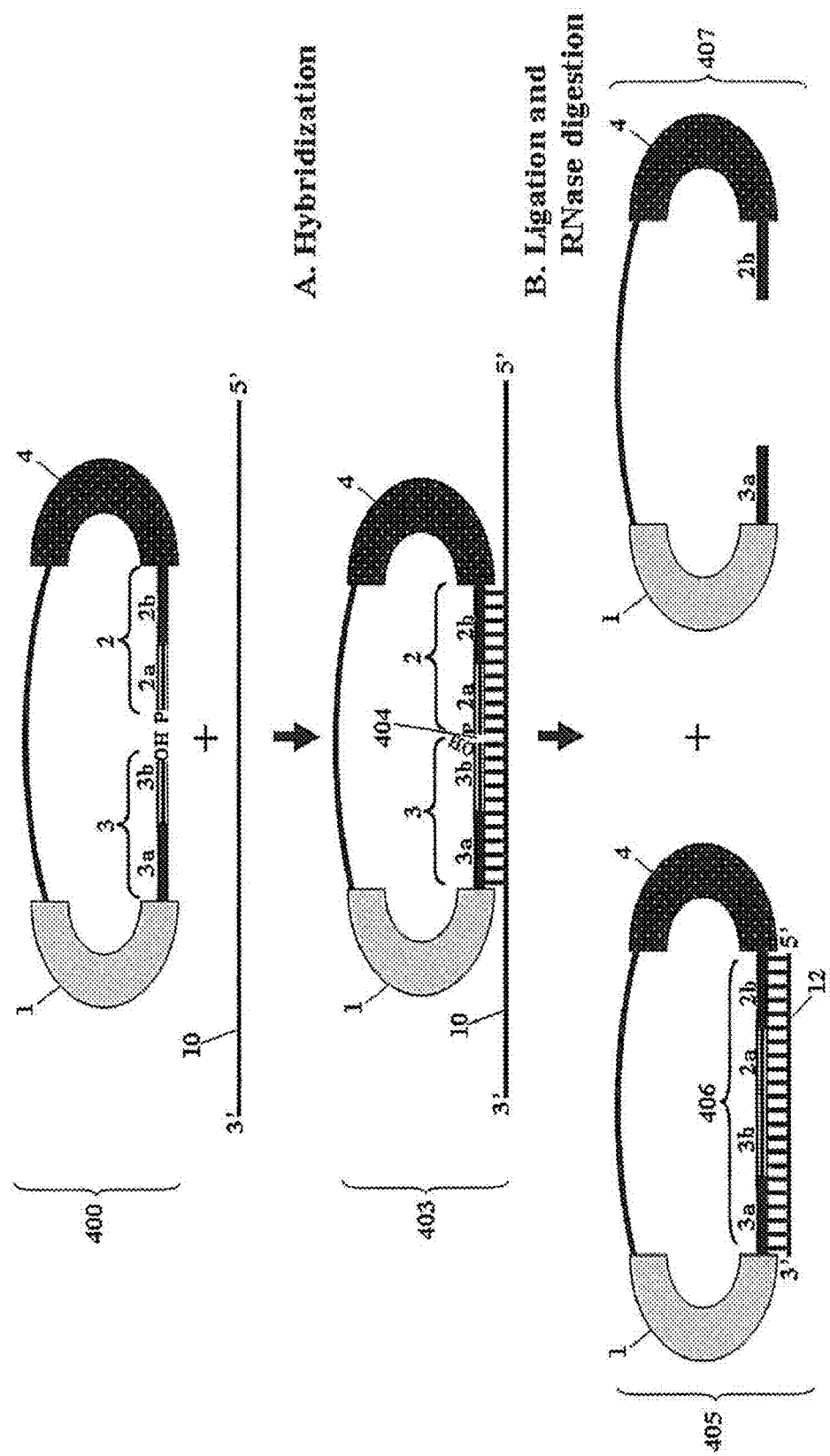

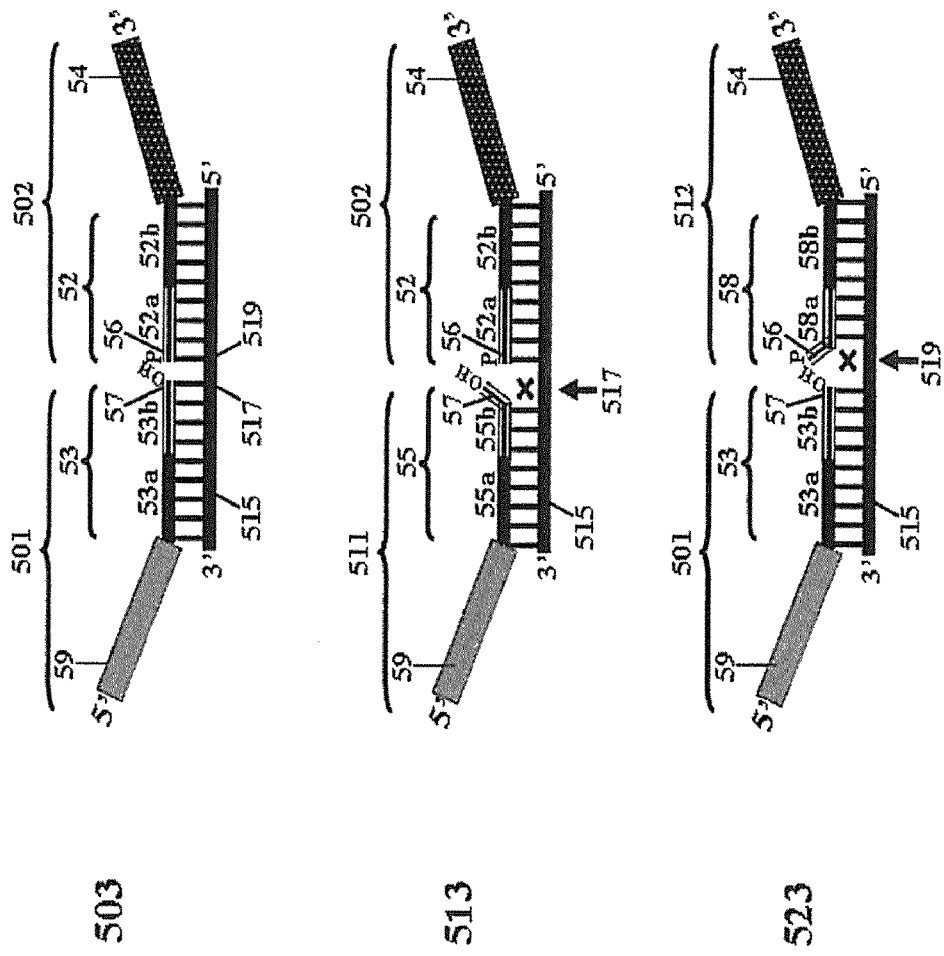

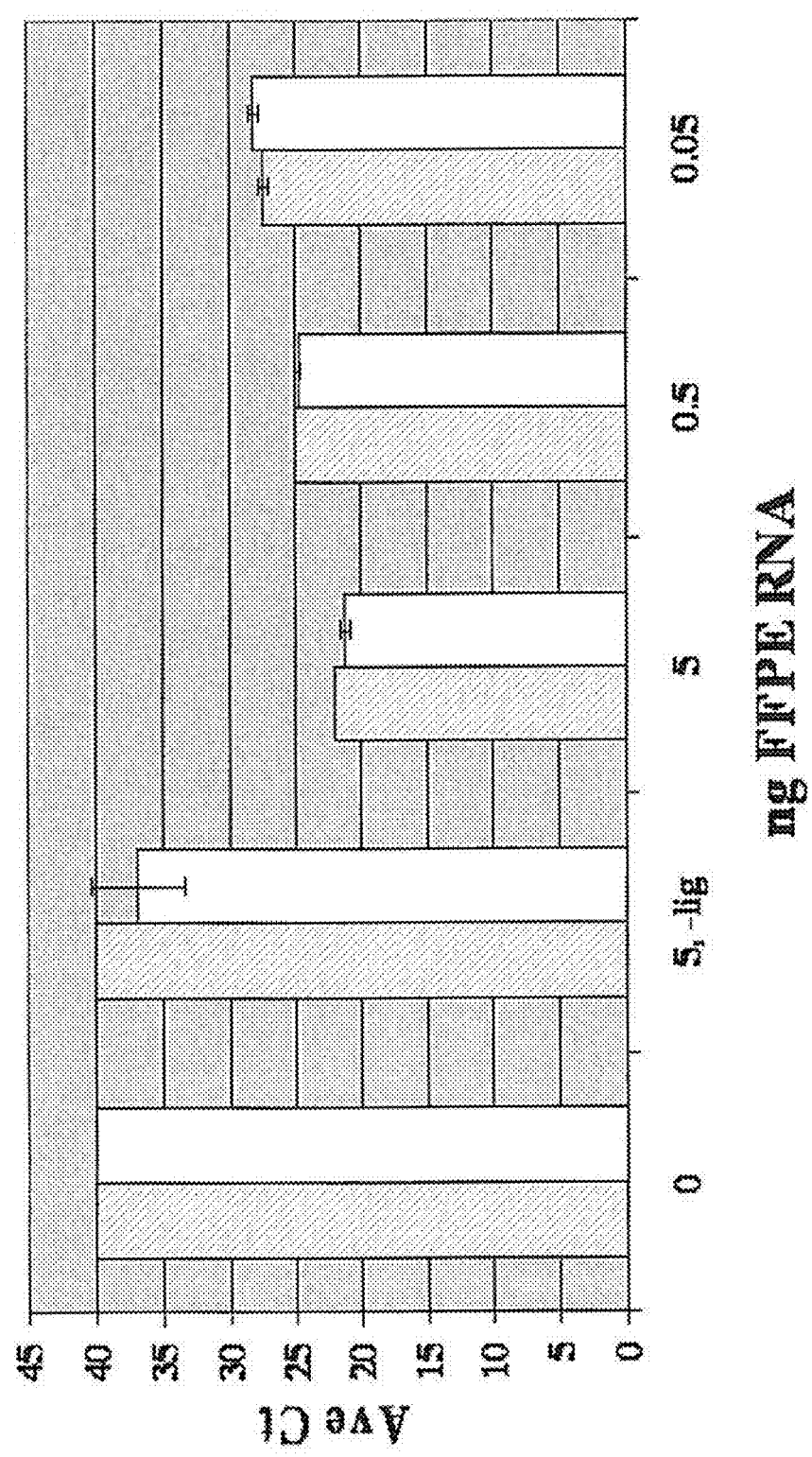

SEQUENCE LISTING

<160> NUMBER OF SEQ ID NOS: 34

<210> SEQ ID NO 1
<211> LENGTH: 35
<212> TYPE: DNA
<213> ORGANISM: Artificial
<220> FEATURE:
<223> OTHER INFORMATION: Synthetic DNA
<220> FEATURE:
<221> NAME/KEY: primer_bind
<222> LOCATION: (1)..(23)
<223> OTHER INFORMATION: deoxyribonucleotides
<220> FEATURE:
<221> NAME/KEY: misc_difference
<222> LOCATION: (24)..(29)
<223> OTHER INFORMATION: nucleotide analogs
<220> FEATURE:
<221> NAME/KEY: misc_RNA
<222> LOCATION: (30)..(35)
<223> OTHER INFORMATION: ribonucleotides

<400> SEQUENCE: 1
gctcacctta acgtagagtc tgcuaggaug gcaag                              35

<210> SEQ ID NO 2
<211> LENGTH: 35
<212> TYPE: DNA
<213> ORGANISM: Artificial
<220> FEATURE:
<223> OTHER INFORMATION: Synthetic DNA/RNA
<220> FEATURE:
<221> NAME/KEY: misc_RNA
<222> LOCATION: (1)..(7)
<223> OTHER INFORMATION: ribonucleotides
<220> FEATURE:
<221> NAME/KEY: misc_difference
<222> LOCATION: (8)..(13)
<223> OTHER INFORMATION: nucleotide analogs
<220> FEATURE:
<221> NAME/KEY: primer_bind
<222> LOCATION: (14)..(35)
<223> OTHER INFORMATION: deoxyribonucleotides

<400> SEQUENCE: 2
ggacuuccug uaatattgtt ggggtagtcg gacct                              35

-continued

```
<210> SEQ ID NO 3
<211> LENGTH: 23
<212> TYPE: DNA
<213> ORGANISM: Artificial
<220> FEATURE:
<223> OTHER INFORMATION: Synthetic DNA
<220> FEATURE:
<221> NAME/KEY: primer_bind
<222> LOCATION: (1)..(23)

<400> SEQUENCE: 3
gctcacccta acgtagagtc tgc                                              23

<210> SEQ ID NO 4
<211> LENGTH: 23
<212> TYPE: DNA
<213> ORGANISM: Artificial
<220> FEATURE:
<223> OTHER INFORMATION: Synthetic DNA
<220> FEATURE:
<221> NAME/KEY: primer_bind
<222> LOCATION: (1)..(23)

<400> SEQUENCE: 4
aggtccgact acccccaacaa tat                                             23

<210> SEQ ID NO 5
<211> LENGTH: 15
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (1)..(15)
<223> OTHER INFORMATION: detector probe sequence

<400> SEQUENCE: 5
taggatggca aggga                                                       15

<210> SEQ ID NO 6
<211> LENGTH: 35
<212> TYPE: DNA
<213> ORGANISM: Artificial
<220> FEATURE:
<223> OTHER INFORMATION: Synthetic DNA/RNA
<220> FEATURE:
<221> NAME/KEY: primer_bind
<222> LOCATION: (1)..(23)
<223> OTHER INFORMATION: deoxyribonucleotides
<220> FEATURE:
<221> NAME/KEY: misc_feature
<222> LOCATION: (24)..(29)
<223> OTHER INFORMATION: nucleotide analogs
<220> FEATURE:
<221> NAME/KEY: misc_RNA
<222> LOCATION: (30)..(35)
<223> OTHER INFORMATION: ribonucleotides

<400> SEQUENCE: 6
gctcacccta acgtagagtc tgcggcuggc gacgc                                 35

<210> SEQ ID NO 7
<211> LENGTH: 35
<212> TYPE: DNA
<213> ORGANISM: Artificial
<220> FEATURE:
<223> OTHER INFORMATION: Synthetic DNA/RNA
<220> FEATURE:
<221> NAME/KEY: misc_RNA
<222> LOCATION: (1)..(7)
<223> OTHER INFORMATION: ribonucleotides
```

```
<220> FEATURE:
<221> NAME/KEY: misc_difference
<222> LOCATION: (8)..(13)
<223> OTHER INFORMATION: nucleotide analogs
<220> FEATURE:
<221> NAME/KEY: primer_bind
<222> LOCATION: (14)..(35)
<223> OTHER INFORMATION: deoxyribonucleotides

<400> SEQUENCE: 7
aaaagaagau gcgtattgtt ggggtagtcg gacct                              35

<210> SEQ ID NO 8
<211> LENGTH: 35
<212> TYPE: DNA
<213> ORGANISM: Artificial
<220> FEATURE:
<223> OTHER INFORMATION: Synthetic DNA/RNA
<220> FEATURE:
<221> NAME/KEY: primer_bind
<222> LOCATION: (1)..(23)
<223> OTHER INFORMATION: deoxyribonucleotides
<220> FEATURE:
<221> NAME/KEY: misc_difference
<222> LOCATION: (24)..(29)
<223> OTHER INFORMATION: nucleotide analogs
<220> FEATURE:
<221> NAME/KEY: misc_RNA
<222> LOCATION: (30)..(35)
<223> OTHER INFORMATION: ribonucleotides

<400> SEQUENCE: 8
gctcacctta acgtagagtc tgcucagugg cacca                              35

<210> SEQ ID NO 9
<211> LENGTH: 35
<212> TYPE: DNA
<213> ORGANISM: Artificial
<220> FEATURE:
<223> OTHER INFORMATION: Synthetic DNA/RNA
<220> FEATURE:
<221> NAME/KEY: misc_RNA
<222> LOCATION: (1)..(7)
<223> OTHER INFORMATION: ribonucleotides
<220> FEATURE:
<221> NAME/KEY: misc_difference
<222> LOCATION: (8)..(13)
<223> OTHER INFORMATION: nucleotide analogs
<220> FEATURE:
<221> NAME/KEY: primer_bind
<222> LOCATION: (14)..(35)
<223> OTHER INFORMATION: deoxyribonucleotides

<400> SEQUENCE: 9
accgauccaa agutattgtt ggggtagtcg gacct                              35

<210> SEQ ID NO 10
<211> LENGTH: 14
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (1)..(14)
<223> OTHER INFORMATION: detector probe sequence

<400> SEQUENCE: 10
ctggcgacgc aaaa                                                    14

<210> SEQ ID NO 11
<211> LENGTH: 15
```

```
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (1)..(15)
<223> OTHER INFORMATION: detector probe sequence

<400> SEQUENCE: 11
tcagtggcac caacc                                                          15

<210> SEQ ID NO 12
<211> LENGTH: 35
<212> TYPE: DNA
<213> ORGANISM: Artificial
<220> FEATURE:
<223> OTHER INFORMATION: Synthetic DNA/RNA
<220> FEATURE:
<221> NAME/KEY: primer_bind
<222> LOCATION: (1)..(23)
<223> OTHER INFORMATION: deoxyribonucleotides
<220> FEATURE:
<221> NAME/KEY: misc_RNA
<222> LOCATION: (24)..(35)
<223> OTHER INFORMATION: ribonucleotides

<400> SEQUENCE: 12
gctcacccta acgtagagtc tgcguaccac accca                                    35

<210> SEQ ID NO 13
<211> LENGTH: 35
<212> TYPE: DNA
<213> ORGANISM: Artificial
<220> FEATURE:
<223> OTHER INFORMATION: Synthetic DNA/RNA
<220> FEATURE:
<221> NAME/KEY: primer_bind
<222> LOCATION: (1)..(23)
<223> OTHER INFORMATION: deoxyribonucleotides
<220> FEATURE:
<221> NAME/KEY: misc_feature
<222> LOCATION: (24)..(25)
<223> OTHER INFORMATION: nucleotide analogs
<220> FEATURE:
<221> NAME/KEY: misc_RNA
<222> LOCATION: (26)..(35)
<223> OTHER INFORMATION: ribonucleotides

<400> SEQUENCE: 13
gctcacccta acgtagagtc tgcguaccac accca                                    35

<210> SEQ ID NO 14
<211> LENGTH: 35
<212> TYPE: DNA
<213> ORGANISM: Artificial
<220> FEATURE:
<223> OTHER INFORMATION: Synthetic DNA/RNA
<220> FEATURE:
<221> NAME/KEY: primer_bind
<222> LOCATION: (1)..(23)
<223> OTHER INFORMATION: deoxyribonucleotides
<220> FEATURE:
<221> NAME/KEY: misc_difference
<222> LOCATION: (24)..(27)
<223> OTHER INFORMATION: nucleotide analogs
<220> FEATURE:
<221> NAME/KEY: misc_RNA
<222> LOCATION: (28)..(35)
<223> OTHER INFORMATION: ribonucleotides

<400> SEQUENCE: 14
gctcacccta acgtagagtc tgcguaccac accca                                    35
```

```
<210> SEQ ID NO 15
<211> LENGTH: 35
<212> TYPE: DNA
<213> ORGANISM: Artificial
<220> FEATURE:
<223> OTHER INFORMATION: Synthetic DNA/RNA
<220> FEATURE:
<221> NAME/KEY: primer_bind
<222> LOCATION: (1)..(23)
<223> OTHER INFORMATION: deoxyribonucleotides
<220> FEATURE:
<221> NAME/KEY: misc_difference
<222> LOCATION: (24)..(29)
<223> OTHER INFORMATION: nucleotide analogs
<220> FEATURE:
<221> NAME/KEY: misc_RNA
<222> LOCATION: (30)..(35)
<223> OTHER INFORMATION: ribonucleotides

<400> SEQUENCE: 15
gctcacctta acgtagagtc tgcguaccac accca                              35

<210> SEQ ID NO 16
<211> LENGTH: 35
<212> TYPE: DNA
<213> ORGANISM: Artificial
<220> FEATURE:
<223> OTHER INFORMATION: Synthetic DNA/RNA
<220> FEATURE:
<221> NAME/KEY: primer_bind
<222> LOCATION: (1)..(23)
<223> OTHER INFORMATION: deoxyribonucleotides
<220> FEATURE:
<221> NAME/KEY: misc_difference
<222> LOCATION: (24)..(31)
<223> OTHER INFORMATION: nucleotide analogs
<220> FEATURE:
<221> NAME/KEY: misc_RNA
<222> LOCATION: (32)..(35)
<223> OTHER INFORMATION: ribonucleotides

<400> SEQUENCE: 16
gctcacctta acgtagagtc tgcguaccac accca                              35

<210> SEQ ID NO 17
<211> LENGTH: 35
<212> TYPE: DNA
<213> ORGANISM: Artificial
<220> FEATURE:
<223> OTHER INFORMATION: Synthetic DNA/RNA
<220> FEATURE:
<221> NAME/KEY: primer_bind
<222> LOCATION: (1)..(23)
<223> OTHER INFORMATION: deoxyribonucleotides
<220> FEATURE:
<221> NAME/KEY: misc_difference
<222> LOCATION: (24)..(33)
<223> OTHER INFORMATION: nucleotide analogs
<220> FEATURE:
<221> NAME/KEY: misc_RNA
<222> LOCATION: (34)..(35)
<223> OTHER INFORMATION: ribonucleotides

<400> SEQUENCE: 17
gctcacctta acgtagagtc tgcguaccac accca                              35

<210> SEQ ID NO 18
<211> LENGTH: 35
<212> TYPE: DNA
<213> ORGANISM: Artificial
<220> FEATURE:
<223> OTHER INFORMATION: Synthetic DNA/RNA
```

```
<220> FEATURE:
<221> NAME/KEY: misc_RNA
<222> LOCATION: (1)..(13)
<223> OTHER INFORMATION: ribonucleotides
<220> FEATURE:
<221> NAME/KEY: primer_bind
<222> LOCATION: (14)..(35)
<223> OTHER INFORMATION: deoxyribonucleotides

<400> SEQUENCE: 18
gccgacaaaa ugctattgtt ggggtagtcg gacct                            35

<210> SEQ ID NO 19
<211> LENGTH: 35
<212> TYPE: DNA
<213> ORGANISM: Artificial
<220> FEATURE:
<223> OTHER INFORMATION: Synthetic DNA
<220> FEATURE:
<221> NAME/KEY: misc_RNA
<222> LOCATION: (1)..(11)
<223> OTHER INFORMATION: ribonucleotides
<220> FEATURE:
<221> NAME/KEY: misc_difference
<222> LOCATION: (12)..(13)
<223> OTHER INFORMATION: nucleotide analogs
<220> FEATURE:
<221> NAME/KEY: primer_bind
<222> LOCATION: (14)..(35)
<223> OTHER INFORMATION: deoxyribonucleotides

<400> SEQUENCE: 19
gccgacaaaa ugctattgtt ggggtagtcg gacct                            35

<210> SEQ ID NO 20
<211> LENGTH: 35
<212> TYPE: DNA
<213> ORGANISM: Artificial
<220> FEATURE:
<223> OTHER INFORMATION: Synthetic DNA/RNA
<220> FEATURE:
<221> NAME/KEY: misc_RNA
<222> LOCATION: (1)..(9)
<223> OTHER INFORMATION: ribonucleotides
<220> FEATURE:
<221> NAME/KEY: misc_difference
<222> LOCATION: (10)..(13)
<223> OTHER INFORMATION: nucleotide analogs
<220> FEATURE:
<221> NAME/KEY: primer_bind
<222> LOCATION: (14)..(35)
<223> OTHER INFORMATION: deoxyribonucleotides

<400> SEQUENCE: 20
gccgacaaaa ugctattgtt ggggtagtcg gacct                            35

<210> SEQ ID NO 21
<211> LENGTH: 35
<212> TYPE: DNA
<213> ORGANISM: Artificial
<220> FEATURE:
<223> OTHER INFORMATION: Synthetic DNA
<220> FEATURE:
<221> NAME/KEY: misc_RNA
<222> LOCATION: (1)..(7)
<223> OTHER INFORMATION: ribonucleotides
<220> FEATURE:
<221> NAME/KEY: misc_difference
<222> LOCATION: (8)..(13)
<223> OTHER INFORMATION: nucleotide analogs
<220> FEATURE:
<221> NAME/KEY: primer_bind
<222> LOCATION: (14)..(35)
<223> OTHER INFORMATION: deoxyribonucleotides
```

```
<400> SEQUENCE: 21
gccgacaaaa ugctattgtt ggggtagtcg gacct                         35

<210> SEQ ID NO 22
<211> LENGTH: 35
<212> TYPE: DNA
<213> ORGANISM: Artificial
<220> FEATURE:
<223> OTHER INFORMATION: Synthetic DNA/RNA
<220> FEATURE:
<221> NAME/KEY: misc_RNA
<222> LOCATION: (1)..(5)
<223> OTHER INFORMATION: ribonucleotides
<220> FEATURE:
<221> NAME/KEY: misc_difference
<222> LOCATION: (6)..(13)
<223> OTHER INFORMATION: nucleotide analogs
<220> FEATURE:
<221> NAME/KEY: primer_bind
<222> LOCATION: (14)..(35)
<223> OTHER INFORMATION: deoxyribonucleotides

<400> SEQUENCE: 22
gccgacaaaa ugctattgtt ggggtagtcg gacct                         35

<210> SEQ ID NO 23
<211> LENGTH: 35
<212> TYPE: DNA
<213> ORGANISM: Artificial
<220> FEATURE:
<223> OTHER INFORMATION: Synthetic DNA/RNA
<220> FEATURE:
<221> NAME/KEY: misc_RNA
<222> LOCATION: (1)..(3)
<223> OTHER INFORMATION: ribonucleotides
<220> FEATURE:
<221> NAME/KEY: misc_difference
<222> LOCATION: (4)..(13)
<223> OTHER INFORMATION: nucleotide analogs
<220> FEATURE:
<221> NAME/KEY: primer_bind
<222> LOCATION: (14)..(35)
<223> OTHER INFORMATION: deoxyribonucleotides

<400> SEQUENCE: 23
gccgacaaaa ugctattgtt ggggtagtcg gacct                         35

<210> SEQ ID NO 24
<211> LENGTH: 25
<212> TYPE: RNA
<213> ORGANISM: Artificial
<220> FEATURE:
<223> OTHER INFORMATION: Synthetic RNA
<220> FEATURE:
<221> NAME/KEY: misc_difference
<222> LOCATION: (1)..(6)
<223> OTHER INFORMATION: nucleotide analogs
<220> FEATURE:
<221> NAME/KEY: misc_RNA
<222> LOCATION: (7)..(19)
<223> OTHER INFORMATION: ribonucleotides
<220> FEATURE:
<221> NAME/KEY: misc_difference
<222> LOCATION: (20)..(25)
<223> OTHER INFORMATION: nucleotide analogs

<400> SEQUENCE: 24
guaccacacc cagccgacaa aaugc                                    25

<210> SEQ ID NO 25
<211> LENGTH: 25
```

```
<212> TYPE: DNA
<213> ORGANISM: Artificial
<220> FEATURE:
<223> OTHER INFORMATION: Synthetic DNA

<400> SEQUENCE: 25
gcattttgtc ggctgggtgt ggtac                                    25

<210> SEQ ID NO 26
<211> LENGTH: 25
<212> TYPE: DNA
<213> ORGANISM: Artificial
<220> FEATURE:
<223> OTHER INFORMATION: Synthetic DNA

<400> SEQUENCE: 26
gcattttgtc ggcagggtgt ggtac                                    25

<210> SEQ ID NO 27
<211> LENGTH: 25
<212> TYPE: DNA
<213> ORGANISM: Artificial
<220> FEATURE:
<223> OTHER INFORMATION: Synthetic DNA

<400> SEQUENCE: 27
gcattttgtc gggtgggtgt ggtac                                    25

<210> SEQ ID NO 28
<211> LENGTH: 25
<212> TYPE: RNA
<213> ORGANISM: Artificial
<220> FEATURE:
<223> OTHER INFORMATION: Synthetic RNA

<400> SEQUENCE: 28
gcauuuuguc ggcugggugu gguac                                    25

<210> SEQ ID NO 29
<211> LENGTH: 25
<212> TYPE: RNA
<213> ORGANISM: Artificial
<220> FEATURE:
<223> OTHER INFORMATION: Synthetic RNA
<220> FEATURE:
<221> NAME/KEY: misc_difference
<222> LOCATION: (1)..(6)
<223> OTHER INFORMATION: nucleotide analogs
<220> FEATURE:
<221> NAME/KEY: misc_RNA
<222> LOCATION: (7)..(19)
<223> OTHER INFORMATION: ribonucleotides
<220> FEATURE:
<221> NAME/KEY: misc_difference
<222> LOCATION: (20)..(25)
<223> OTHER INFORMATION: nucleotide analogs

<400> SEQUENCE: 29
uaggauggca agggacuucc uguaa                                    25

<210> SEQ ID NO 30
<211> LENGTH: 25
<212> TYPE: DNA
<213> ORGANISM: Artificial
<220> FEATURE:
<223> OTHER INFORMATION: Synthetic DNA

<400> SEQUENCE: 30
ttacaggaag tcccttgcca tccta                                    25
```

```
<210> SEQ ID NO 31
<211> LENGTH: 25
<212> TYPE: DNA
<213> ORGANISM: Artificial
<220> FEATURE:
<223> OTHER INFORMATION: Synthetic DNA

<400> SEQUENCE: 31
ttacaggaag tccgttgcca tccta                                              25

<210> SEQ ID NO 32
<211> LENGTH: 25
<212> TYPE: DNA
<213> ORGANISM: Artificial
<220> FEATURE:
<223> OTHER INFORMATION: Synthetic DNA

<400> SEQUENCE: 32
ttacaggaag tcgcttgcca tccta                                              25

<210> SEQ ID NO 33
<211> LENGTH: 25
<212> TYPE: RNA
<213> ORGANISM: Artificial
<220> FEATURE:
<223> OTHER INFORMATION: Synthetic RNA

<400> SEQUENCE: 33
uuacaggaag ucccuugcca uccua                                              25

<210> SEQ ID NO 34
<211> LENGTH: 15
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (1)..(15)
<223> OTHER INFORMATION: detector probe sequence

<400> SEQUENCE: 34
taccacaccc agccg                                                         15
```

CHIMERIC OLIGONUCLEOTIDES FOR LIGATION-ENHANCED NUCLEIC ACID DETECTION, METHODS AND COMPOSITIONS THEREFOR

The present application claims the benefit of U.S. Provisional Application No. 60/946,624 filed Jun. 27, 2007; the contents of which are incorporated herein in their entirety.

The U.S. government has certain rights in this application pursuant to grant no. PHS 2004-2 from the National Institutes of Health and SB grant no. R43 GM075511.

FIELD

The present teachings generally relate to compositions, methods, and kits for detecting and/or quantifying nucleic acid molecules in a sample.

INTRODUCTION

Real-time PCR is routinely used for detection of nucleic acid, and real-time quantitative reverse transcriptase-PCR (qRT-PCR) is routinely used for detection of RNA and for studying gene expression. However, modifications of DNA and RNA due to degradation or sample treatment tend to inhibit the ability of traditional polymerases to replicate template sequences, often resulting in inaccurate measurements and unreliable genomic and, gene expression data. The present teachings provide composition, method and kit embodiments for use in detection and/or quantitation of nucleic acid that is independent of the fidelity of polymerases to copy a modified nucleic acid template.

SUMMARY

Ligation-enhanced nucleic acid detection assay embodiments are provided for detection of short segments of RNA or DNA. In certain embodiments, the assay relies on ligation of probes to generate a template for amplification. Such embodiments do not depend upon the fidelity of a polymerase to copy the short segments of target nucleic acid. Very little background amplification is observed and as few as 1000 copies of target nucleic acid can be reliably detected and quantified. The total assay time can be about 4.5 hrs. In some embodiments, the short segments of RNA or DNA are from a compromised sample. Method embodiments are particularly adept for RNA detection from formalin-fixed and paraffin-embedded (FFPE) samples. Target nucleic acids in heavily degraded and cross-linked FFPE samples, in which classic qRT-PCR assays fail to reliably amplify signal, can be reliably detected and quantified using the assay embodiments provided. Assay embodiments provided are amenable to multiplex detection.

Embodiments of the ligation-enhanced nucleic acid detection assay use at least one first chimeric oligonucleotide probe comprising at least two types of nucleotides from the nucleotide types of deoxyribonucleotides, nucleotide analogs and ribonucleotides. In certain embodiments, a deoxyribonucleotide is present in a primer-specific portion of a probe which serves as a priming site for amplification. In certain embodiments, a nucleotide analog is present in a target-specific portion of a probe to favor strong duplex formation between the probe and a target nucleic acid in the sample. In certain embodiments, a ribonucleotide is present in the target-specific portion and, in some embodiments, is positioned for ligation. Together with at least one second probe, certain probe set embodiments are designed to hybridize to a target nucleic acid such that the 3' end of at least one first probe comprising a forward priming site is either positioned immediately adjacent to, or positioned sufficiently close to the 5' end of at least one second probe comprising a reverse priming site, either leaving a nick between them or leaving a gap that can be filled using a polymerase. In this context, the target nucleic acid acts as a splint or bridge to bring the ends of the probes in close proximity to each other. The probes, thus designed, can use a short (as short as 12 nt) detection footprint.

Embodiments provided include at least one first chimeric oligonucleotide probe, comprising, in a 5' to 3' direction: a primer-specific portion comprising an amplification primer nucleotide sequence; and a target-specific portion, the target-specific portion having complementarity to a 3' portion of a preselected sequence of a target nucleic acid, a length of 6 nucleotides to 44 nucleotides, at least one nucleotide analog at one of the six 5'-most nucleotides wherein the nucleotide analog has enhanced affinity for base pairing as compared to a corresponding non-modified nucleotide, and 3'-OH and 2'-OR groups on the 3'-terminal nucleotide, wherein R comprises H or $C_1$-$C_3$ alkyl.

Further embodiments include a set of chimeric oligonucleotide probes, the probe set Comprising at least one first chimeric oligonucleotide probe; and at least one second chimeric oligonucleotide probe comprising, in a 5' to 3' direction: a target-specific portion having a 5'-terminal nucleotide comprising a 5'-phosphate group, complementarity to a 5' portion of the preselected sequence of the target nucleic acid, a length of 6 nucleotides to 44 nucleotides, and a primer-specific portion comprising an amplification primer nucleotide sequence. In certain embodiments, when the at least one first and the at least one second chimeric oligonucleotide probes are annealed to the target nucleic acid, the 3' hydroxyl group of the at least one first chimeric oligonucleotide probe is positioned immediately adjacent to the 5' phosphate group of the at least one second chimeric oligonucleotide probe. In some embodiments, the probes of a target-specific probe set are designed to hybridize to adjacent regions of the target nucleic acid sequence and, tinder suitable conditions, the probes can be ligated together to form a ligation product.

In some embodiments of the set of chimeric oligonucleotide probes, the 3'-terminal nucleotide, the 3'-penultimate nucleotide, or both of the 3'-terminal and the 3'-penultimate nucleotides of the at least one first chimeric oligonucleotide probe comprise non-modified ribonucleotides. In certain embodiments of the set of chimeric oligonucleotide probes, the 3'-terminal nucleotide, the 3'-penultimate nucleotide, or both of the 3'-terminal and the 3'-penultimate nucleotides of the at least one first chimeric oligonucleotide probe comprise nucleotide analogs having enhanced affinity for base pairing as compared to a non-modified ribonucleotide. In certain embodiments, the 5'-terminal nucleotide of the target-specific portion of the second chimeric oligonucleotide probe comprises a non-modified ribonucleotide.

In certain probe set embodiments, the target-specific portion of the at least one second chimeric oligonucleotide probe comprises at least one nucleotide analog at one of the six 3'-most nucleotides, wherein the nucleotide analog has enhanced affinity for base pairing as compared to a corresponding non-modified nucleotide.

In certain probe set embodiments, the 5'-most nucleotide of the target-specific region of the at least one first chimeric oligonucleotide probe comprises a nucleotide analog. In certain embodiments, two, three, four, five, or six of the six most 5'-nucleotides of the target-specific portion of the at least one first chimeric oligonucleotide probe comprise a nucleotide analog. For some embodiments, the nucleotide analogs are contiguous.

In certain probe, set embodiments, the 3'-most nucleotide of the target-specific region of the at least one second chimeric oligonucleotide probe comprises a nucleotide analog. For further embodiments, two, three, four, five, or six of the six most 3'-nucleotides of the target-specific portion of the at least one second chimeric oligonucleotide probe comprise a nucleotide analog. For some embodiments, the nucleotide analogs are contiguous.

The target-specific portion of the at least one first chimeric oligonucleotide probe comprises, in certain embodiments, in a 5' to 3' direction, a first portion and a second portion, wherein the first portion comprises primarily nucleotide analogs and the second portion comprises primarily non-modified ribonucleotides. In certain embodiments, the first portion comprises primarily nucleotide analogs and the second portion comprises at least one deoxyribonucleotide.

Similarly, in some embodiments, the target-specific portion of the at least one second chimeric oligonucleotide probe comprises, in a 5' to 3' direction, a first portion and a second portion, wherein the first portion comprises primarily non-modified ribonucleotides and the second portion comprises primarily nucleotide analogs. In certain embodiments, the first portion comprises at least one deoxyribonucleotide and the second portion comprises primarily nucleotide analogs.

In certain probe set embodiments, when nucleotide sequences of the probes are taken together, the sequences comprise a nucleotide sequence corresponding to at least a part of a detector probe, or the at least one first chimeric oligonucleotide probe comprises a nucleotide sequence corresponding to at least a part of a detector probe, or the target-specific portion of the at least one first chimeric oligonucleotide probe comprises a nucleotide sequence corresponding to at least a part of a detector probe.

In certain probe set embodiments, the nucleotide sequence of the target-specific portion of the at least one first chimeric oligonucleotide probe taken together with the target-specific portion of the at least one second chimeric oligonucleotide probe represent a sense sequence that is capable of annealing to an antisense strand of a target nucleic acid. In other embodiments, the nucleotide sequence of the target-specific portion of the at least one first chimeric oligonucleotide probe taken together with the target-specific portion of the at least one second chimeric oligonucleotide probe represent an antisense sequence that is capable of annealing to a sense strand of a target nucleic acid. In yet further embodiments, the nucleotide sequence of the target-specific portion of the at least one first chimeric oligonucleotide probe together with the nucleotide sequence of the target-specific portion of the at least one second chimeric oligonucleotide probe is designed to anneal across an exon junction of the target nucleic acid.

In certain probe set embodiments, the at least one first chimeric oligonucleotide probe comprises, in a 5' to 3' direction: a primer-specific portion comprising an amplification primer nucleotide sequence; and a target-specific portion, the target-specific portion having complementarity to a 3' portion of a preselected sequence of target nucleic acid, a length of 6 nucleotides to 44 nucleotides, at least one nucleotide analog at one of the six 5'-most nucleotides wherein the nucleotide analog has enhanced affinity for base pairing as compared to a corresponding non-modified nucleotide, and 3'-OH and 2'-OR groups on the 3'-terminal nucleotide, wherein R comprises H or $C_1$-$C_3$ alkyl; the at least one second chimeric oligonucleotide probe comprises, in a 5' to 3' direction: a target-specific portion having a 5'-terminal nucleotide comprising a 5'-phosphate group, complementary to a 5' portion of the preselected sequence of the target nucleic acid, at least one nucleotide analog at one of the six 3'-most nucleotides wherein the nucleotide analog has enhanced affinity for base pairing as compared to a corresponding non-modified nucleotide, a length of 6 nucleotides to 44 nucleotides, and a primer-specific portion comprising an amplification primer nucleotide sequence; wherein, when the at least one first and the at least one second chimeric oligonucleotide probes are annealed to the target-nucleic acid, the 3' hydroxyl group of the at least one first chimeric oligonucleotide probe is positioned immediately adjacent to the 5' phosphate group of the at least one second chimeric oligonucleotide probe.

Certain method embodiments for detecting a target nucleic acid in a sample comprise (a) contacting the sample with a set of chimeric oligonucleotide probes for a time and under conditions suitable to form an annealed product; (b) contacting the annealed product with a polypeptide having double-strand dependent ligase activity for a time and under conditions suitable to form a ligated product; and (c) detecting the target nucleic acid in the sample by detecting the ligated product, or a surrogate thereof. In certain embodiments, the method further comprises adding a single-strand specific ribonuclease prior to (b), in or during (b), or prior to (c). In certain embodiments, contacting the sample with at least one set of chimeric oligonucleotide probes comprises isolating nucleic acid from the sample and contacting the isolated nucleic acids with the at least one set of chimeric oligonucleotide probes.

Certain embodiments of the disclosed methods include multiplex assays for detecting or quantitating a multiplicity of different target nucleic acids; other embodiments are directed to singleplex assays for detecting or quantitating a single, target nucleic acid; while some embodiments contemplate a multiplex assay comprising at least one singleplex reaction.

In certain embodiments, a method for detecting a target nucleic acid in a sample comprises contacting the sample with a set of chimeric oligonucleotide probes for a time and under conditions suitable to form an annealed product; contacting the annealed product with a polypeptide having double-strand dependent ligase activity, such as T4 Rnl2 ligase or an enzymatically active mutant or variant thereof, for a time and under conditions suitable to form a ligated product; and detecting the target nucleic acid by detecting the ligated product. The method may further comprise adding a single-strand specific ribonuclease prior to, in or during, contacting with the polypeptide having ligase activity, or prior to detecting the target nucleic acid. In a further embodiment, the method may comprise adding a protease prior to detecting the target nucleic acid. In another embodiment, the method may comprise isolating nucleic acid from the sample and contacting the isolated nucleic acid with the at least one set of chimeric oligonucleotide probes.

Embodiments of teachings include, for example, compositions comprising at least one first chimeric oligonucleotide probe, at least one second chimeric oligonucleotide probe, a polypeptide having double-strand dependent ligase activity, or a combination thereof, and kits as described below. Further embodiments include gap-filled probes, a plurality of probes, and a single probe that, when ligated, forms a circular probe.

Nucleic acid detection embodiments herein are useful for samples from a variety of environments such as for genetic analysis, for cancer or disease detection, for forensic analysis, for human identification including paternity testing or criminal investigations, for transplantation screening, for expression analysis, or for quality control and certification of products and processes, for example. Certain of the environments may result in compromised samples. In certain quality control or certification embodiments, at least one synthetic control target nucleic acid having a control target detection region, and at least one set of synthetic control chimeric oligonucleotide probes having target-specific portions for the target detection region are provided. Such a set of control probes hybridizes to the control target nucleic acid but does not hybridize to sequences in a test sample thereby providing a measure for quality control. Kits may comprise such synthetic control target nucleic acids and chimeric probes. These and other features of the present teachings will become more apparent from the description herein.

DRAWINGS

The skilled artisan will understand that the drawings, described below, are for illustration purposes only. The drawings are not intended to limit the scope of the present teachings in any way.

FIG. 1A-FIG. 1C provide schematic diagrams depicting a general overview of certain exemplary embodiments for detection of an RNA target.

Figure 2A:
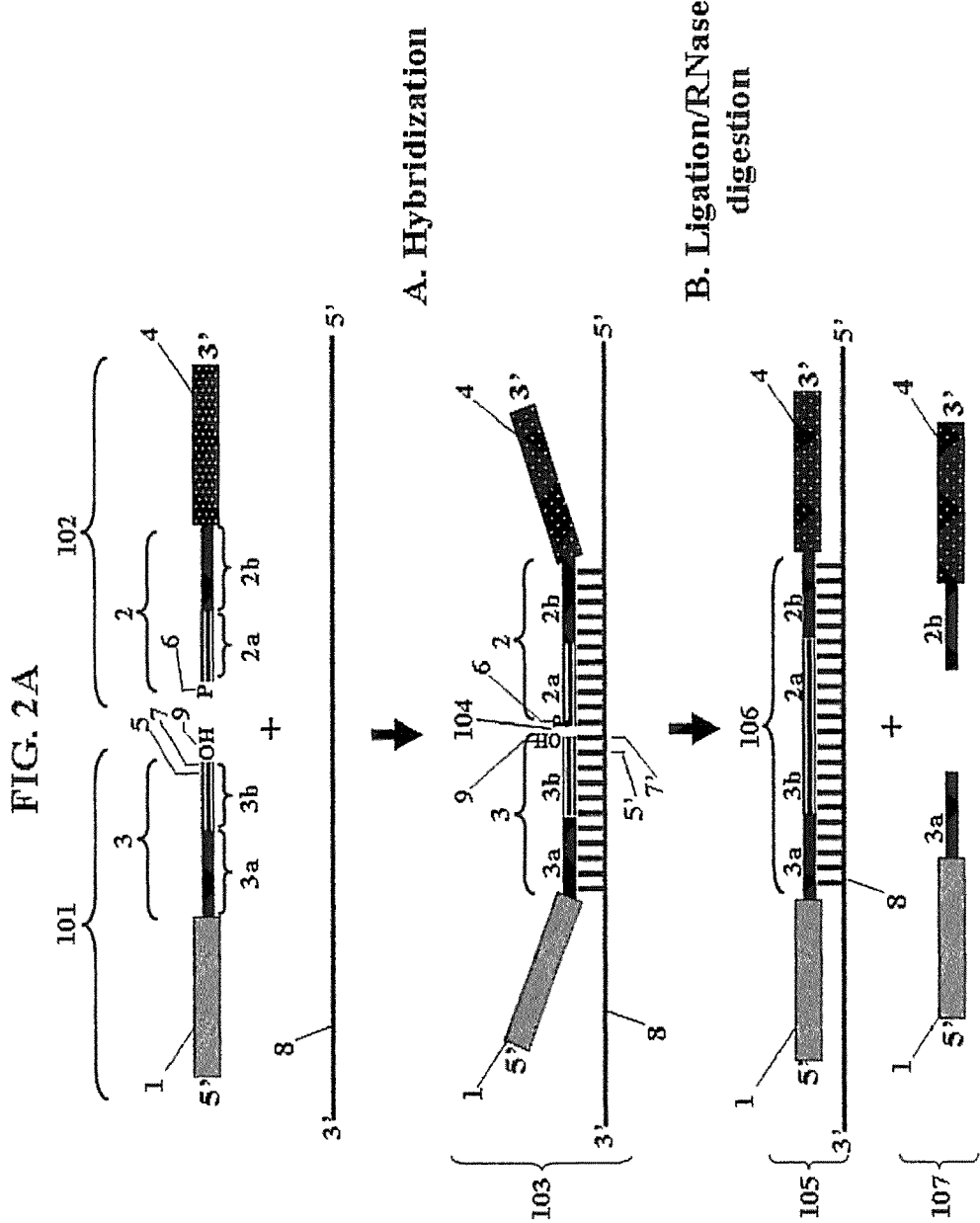
Figure 2B:
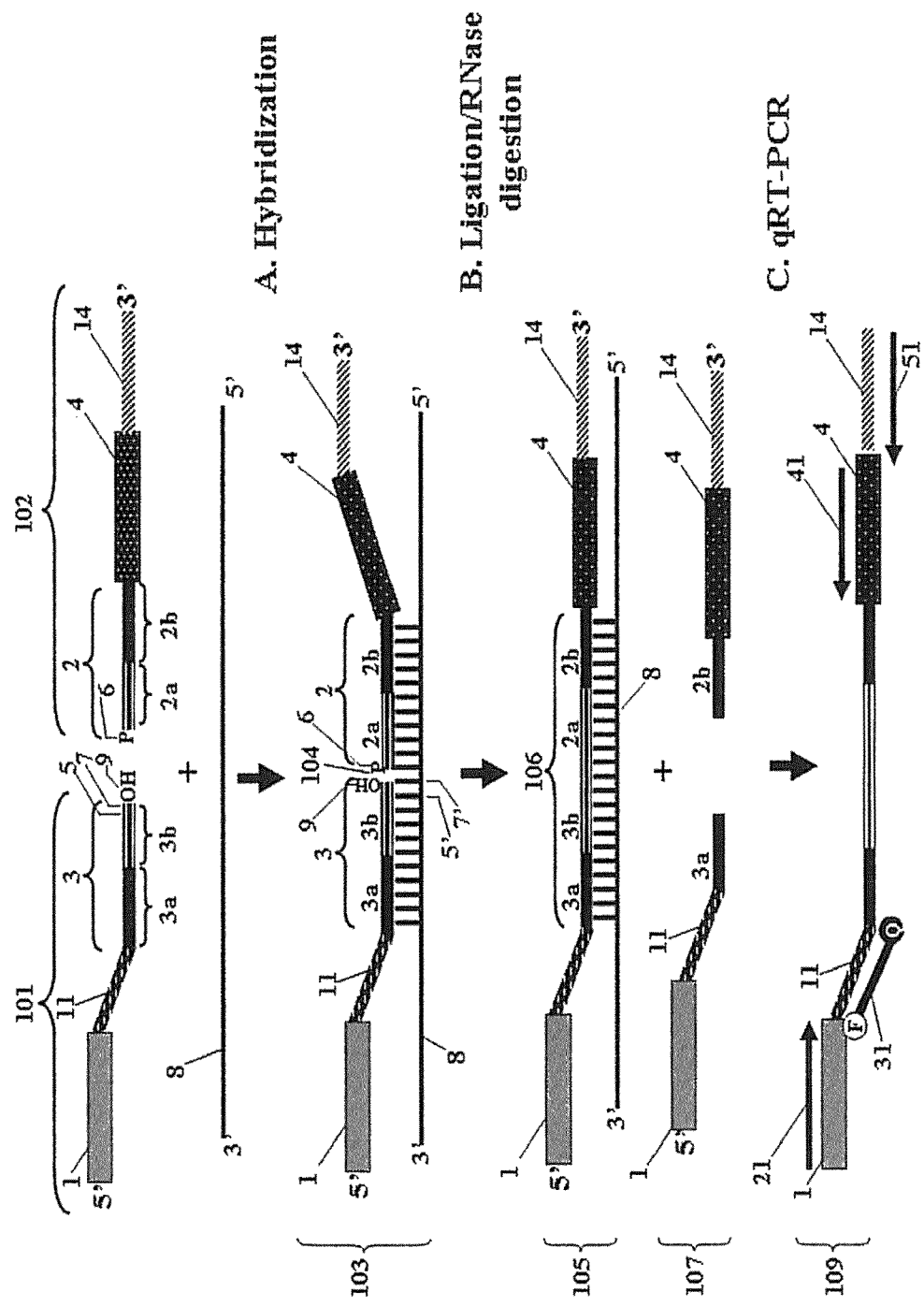

FIG. 2A-FIG. 2B provide a schematic diagrams depicting a general overview of certain exemplary embodiments for detection of a DNA target.

Figure 3:
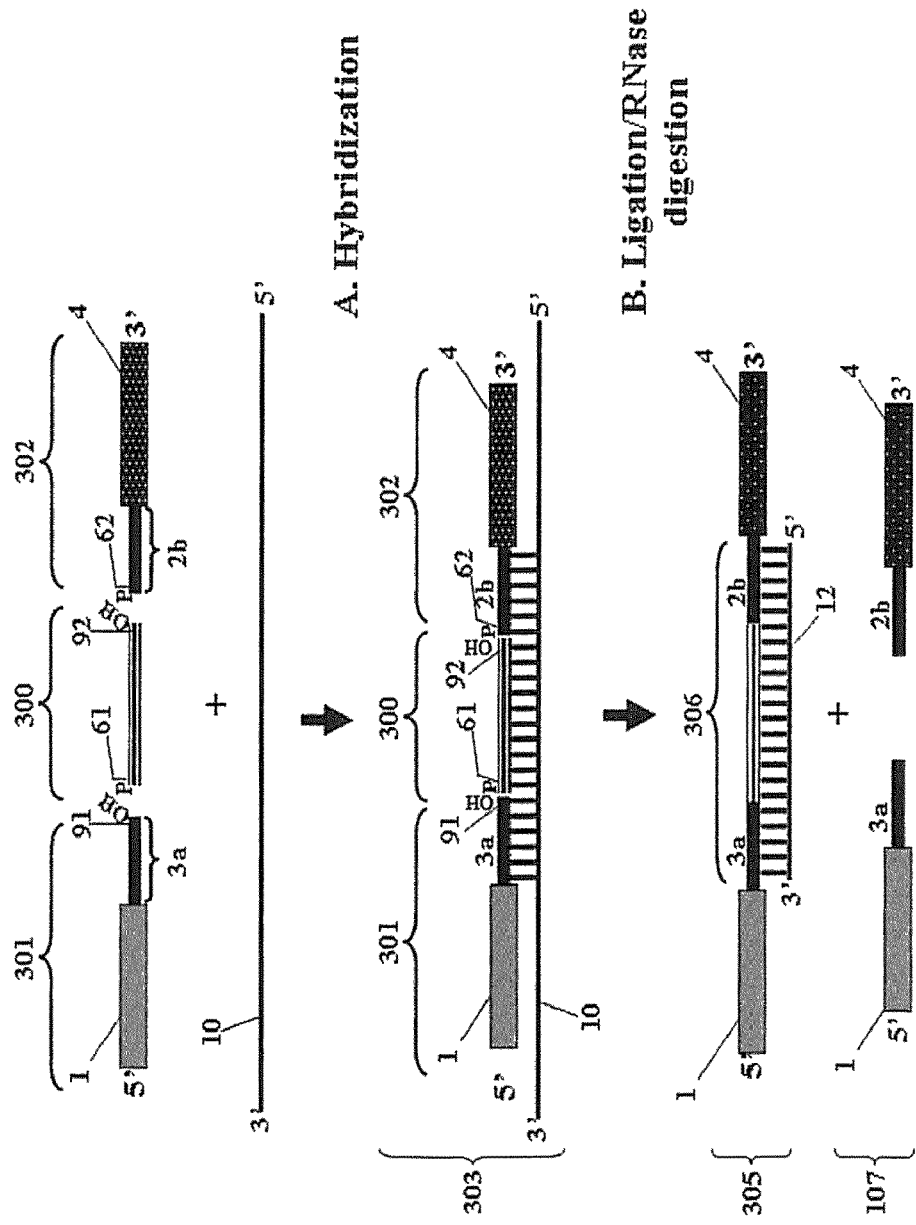

FIG. 3 provides a schematic diagram depicting a general overview of further exemplary embodiments for detection of an RNA target using three probes.

FIG. 4 provides a schematic diagram depicting a general overview of further exemplary embodiments for detection using a single probe.

FIG. 5 provides a schematic diagram depicting a general overview of certain exemplary embodiments for detection of a single nucleotide polymorphism.

Figure 6A:
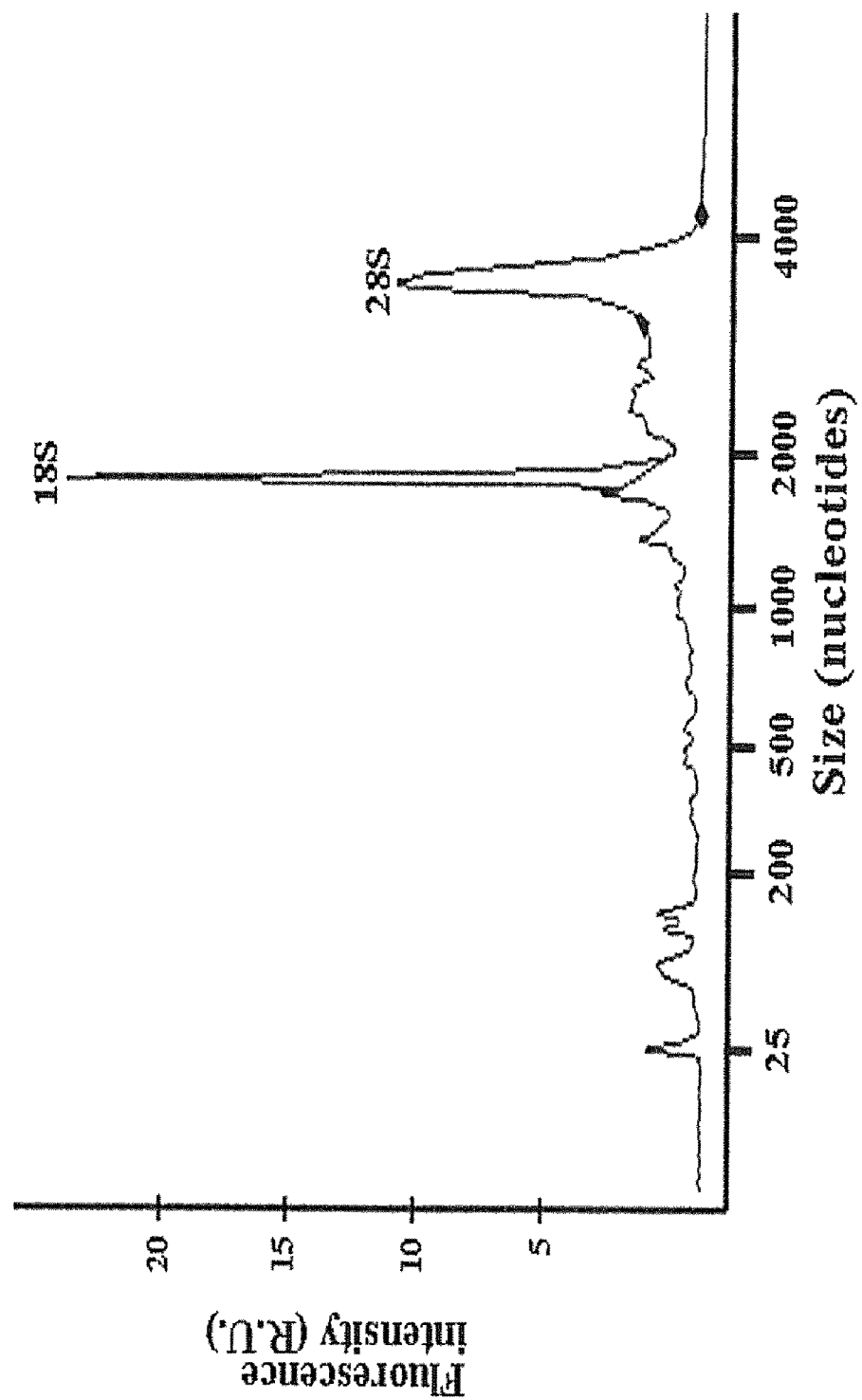
Figure 6B:
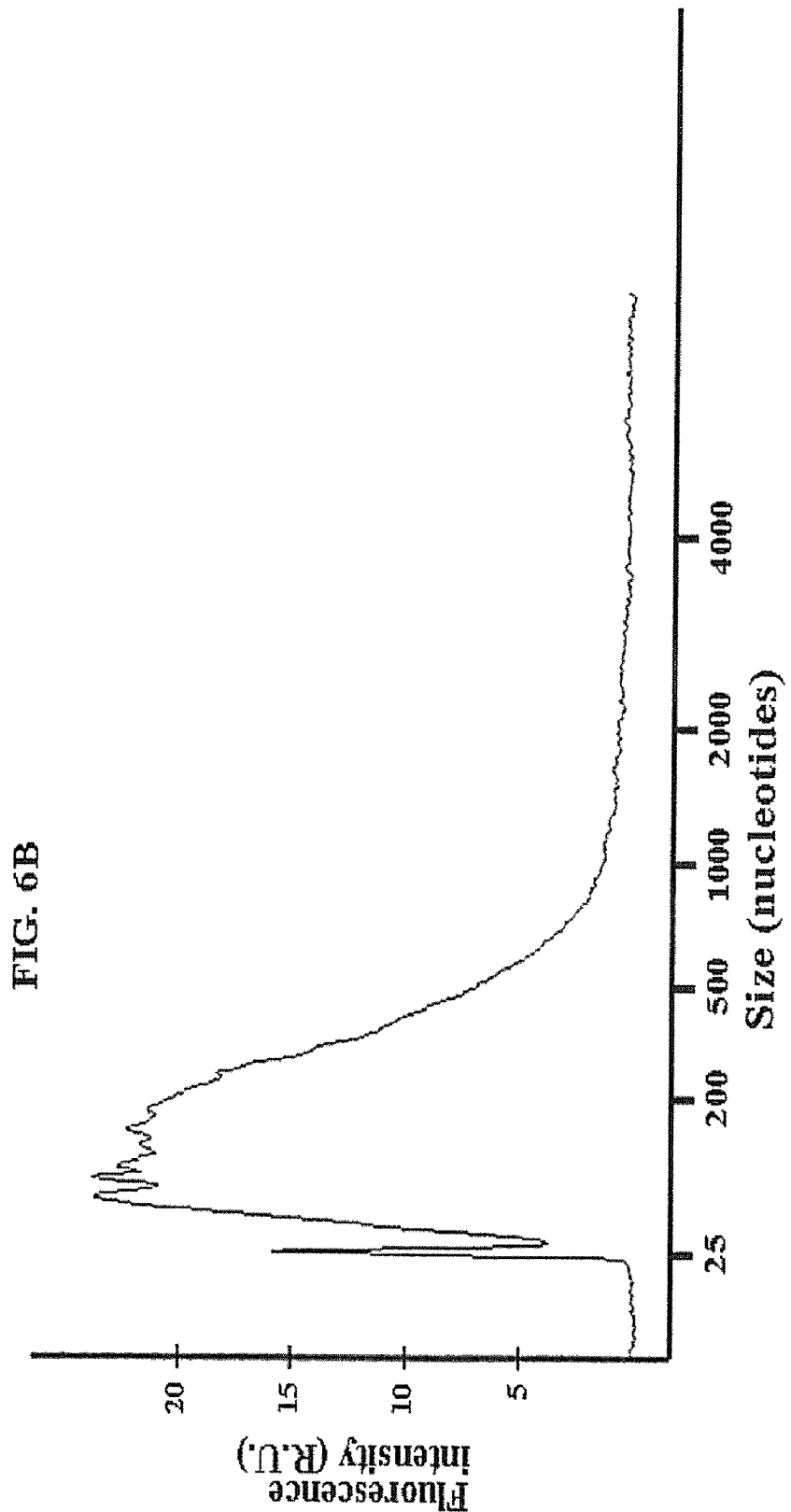
Figure 6C:
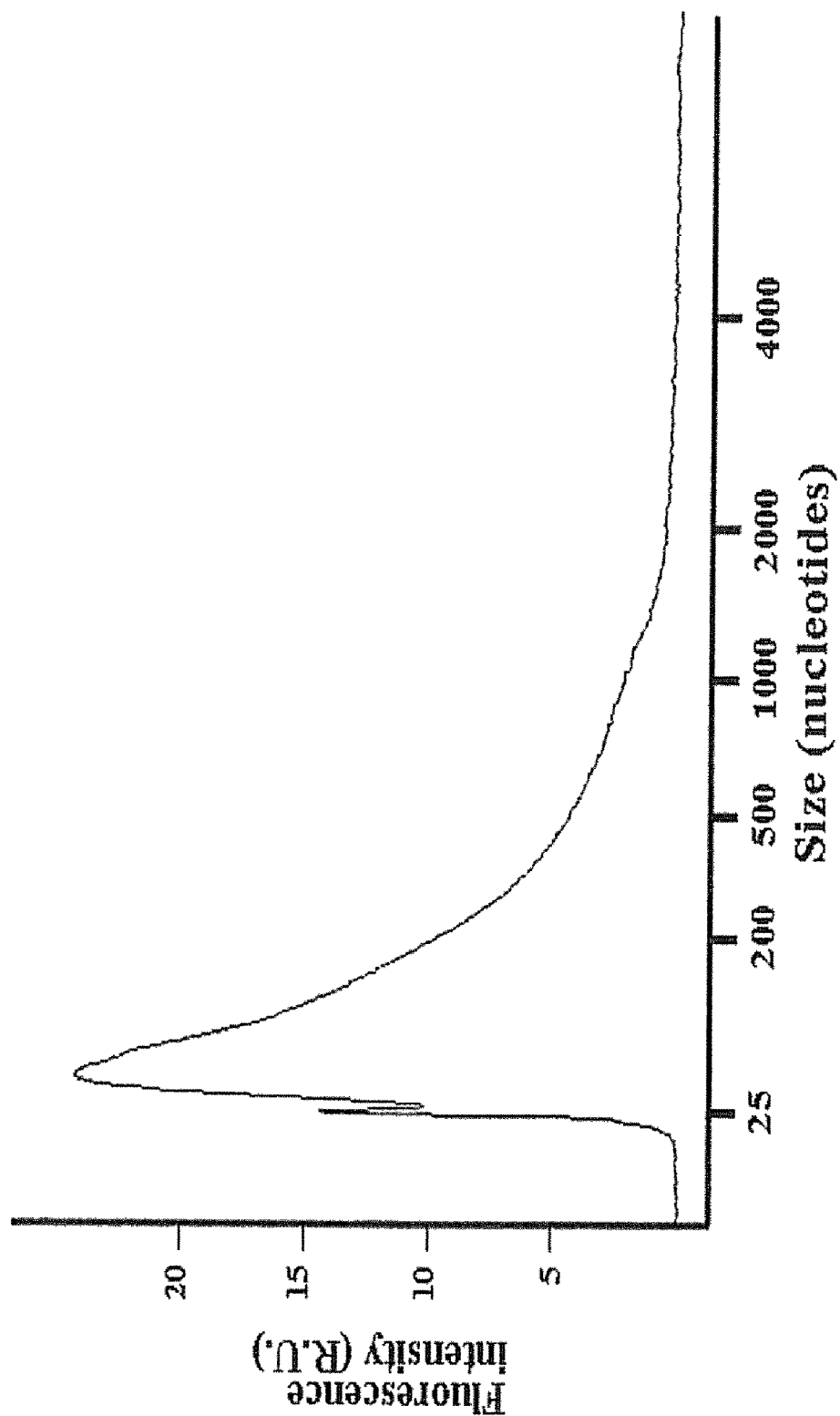

FIG. 6A-FIG. 6C provide a comparison of RNA from frozen tissue versus FFPE tissue samples analyzed as described in Example 1. The x-axis represents size of RNA in nucleotides and the y-axis represents fluorescence intensity in relative units (R.U.). Frozen tissue shows the profile of intact RNA (FIG. 6A); the 18S and 28S ribosomal RNAs are clearly evident. The fixed samples show a profile of highly fragmented, small RNA that peaks early in the profile (FIG. 6B and FIG. 6C).

Figure 7:
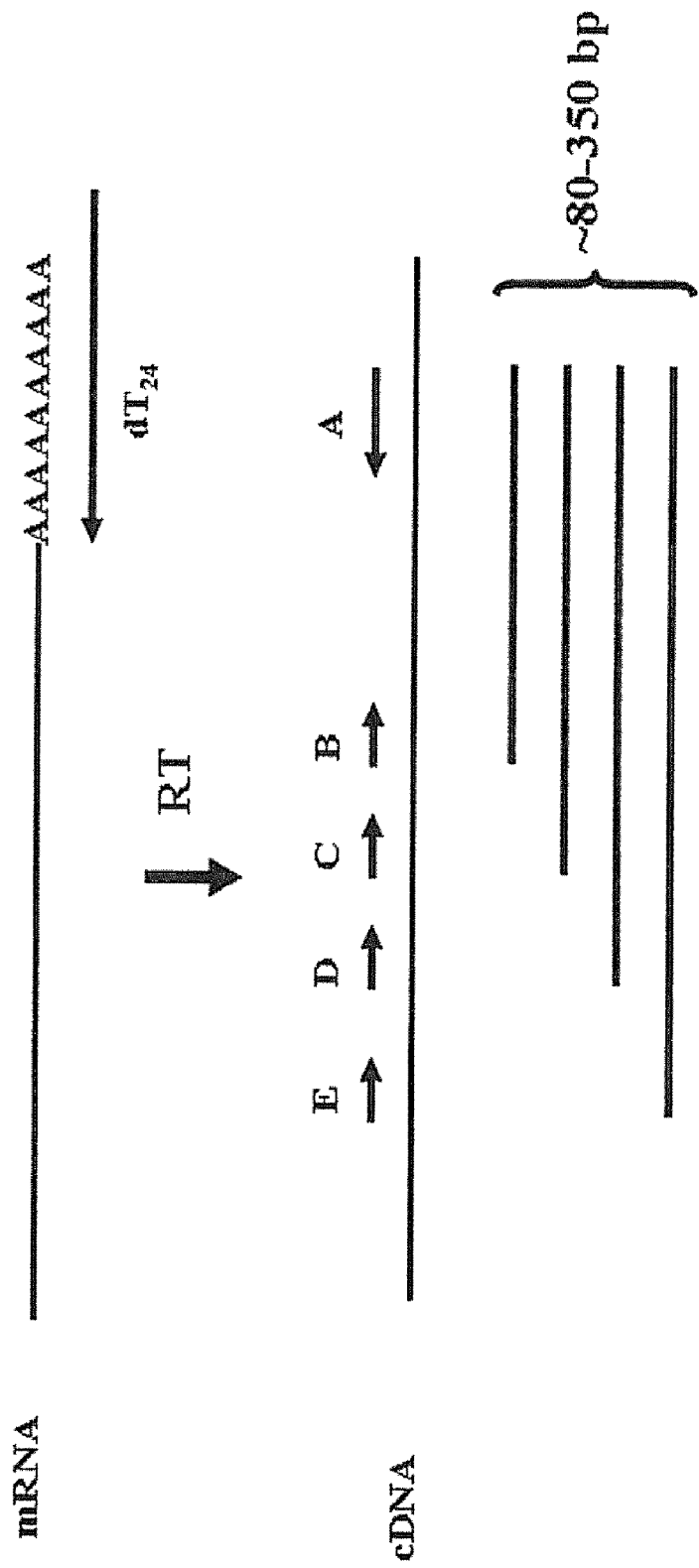

FIG. 7 provides a schematic for an integrity assay for determining the RNA quality of a sample analyzed as in Example 1. When the RNA quality is poor, the ability to amplify longer products decreases. RT, reverse transcriptase; A represents a reverse primer; B, C, D, and E represent forward primers.

Figure 8A:
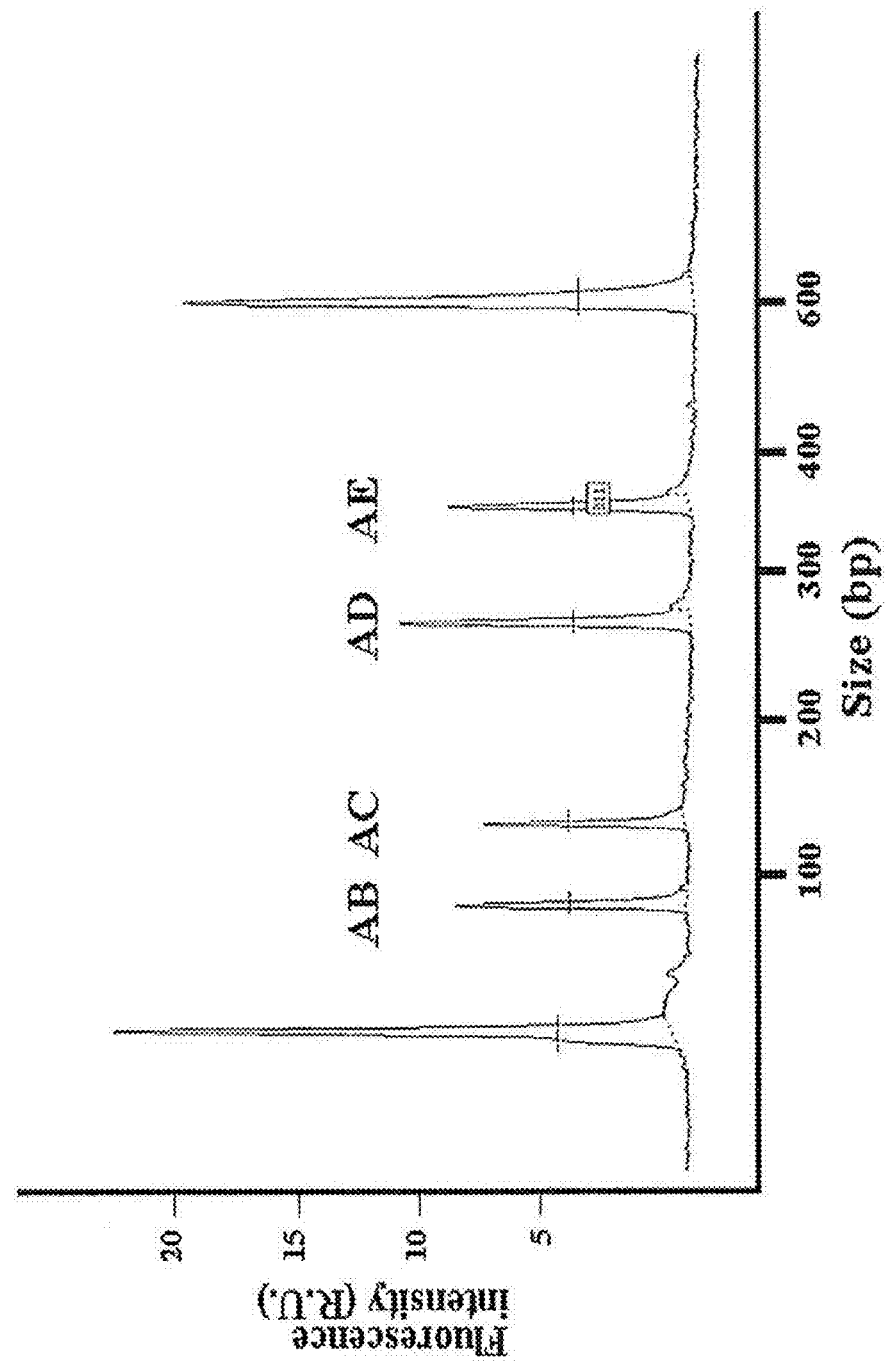
Figure 8B:
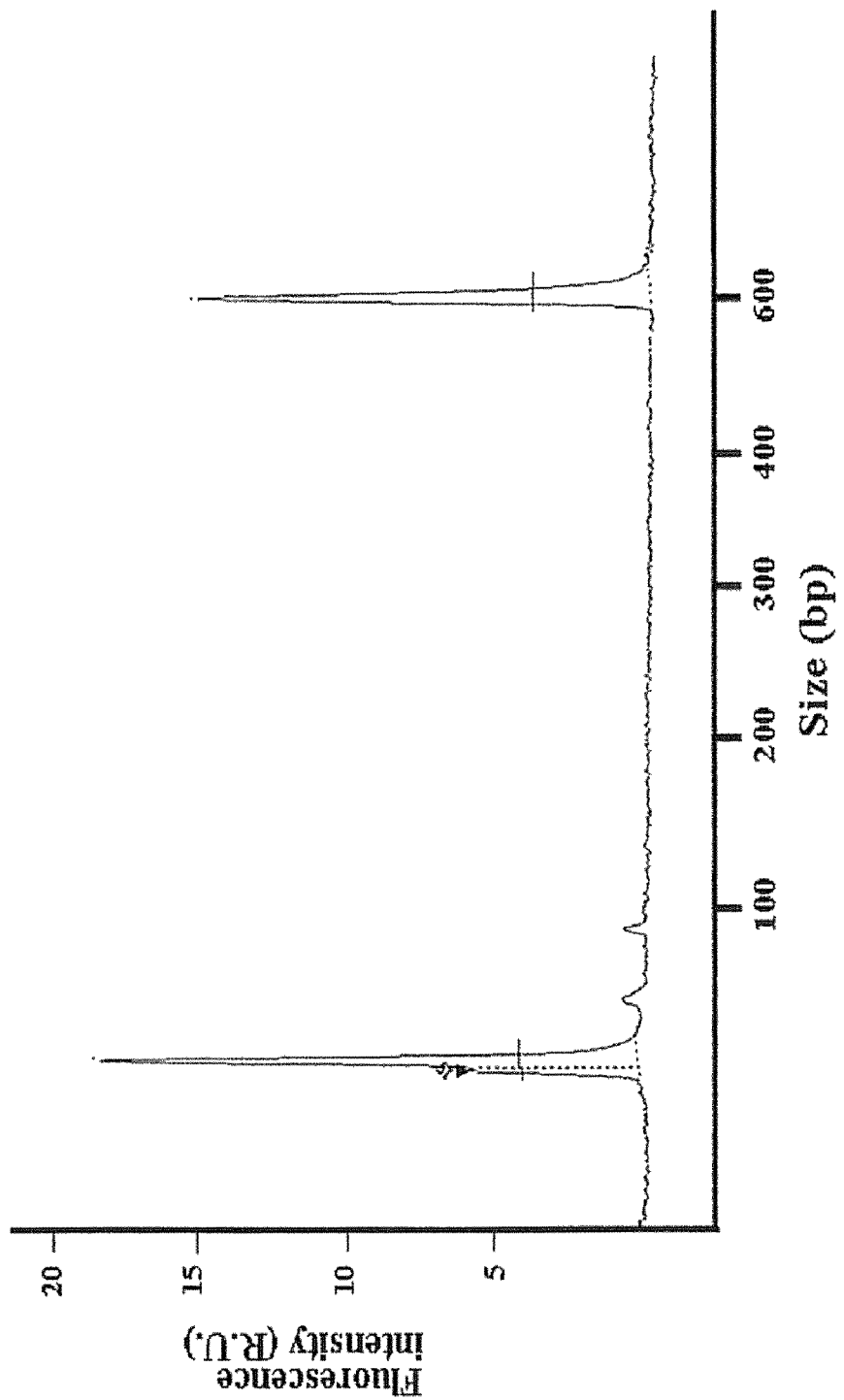

FIG. 8A-FIG. 8B provide results of integrity assays comparing amplified products from a 2-year old FFPE sample (FIG. 8A) with a 13-year old FFPE sample (FIG. 8B). AB, AC, AD, and AE, refer to the products schematically shown in FIG. 7. The x-axis represents size of amplified product in base pairs and the y-axis represents fluorescence intensity in relative units. The older sample does not produce any detectable amplified product.

Figure 9B:
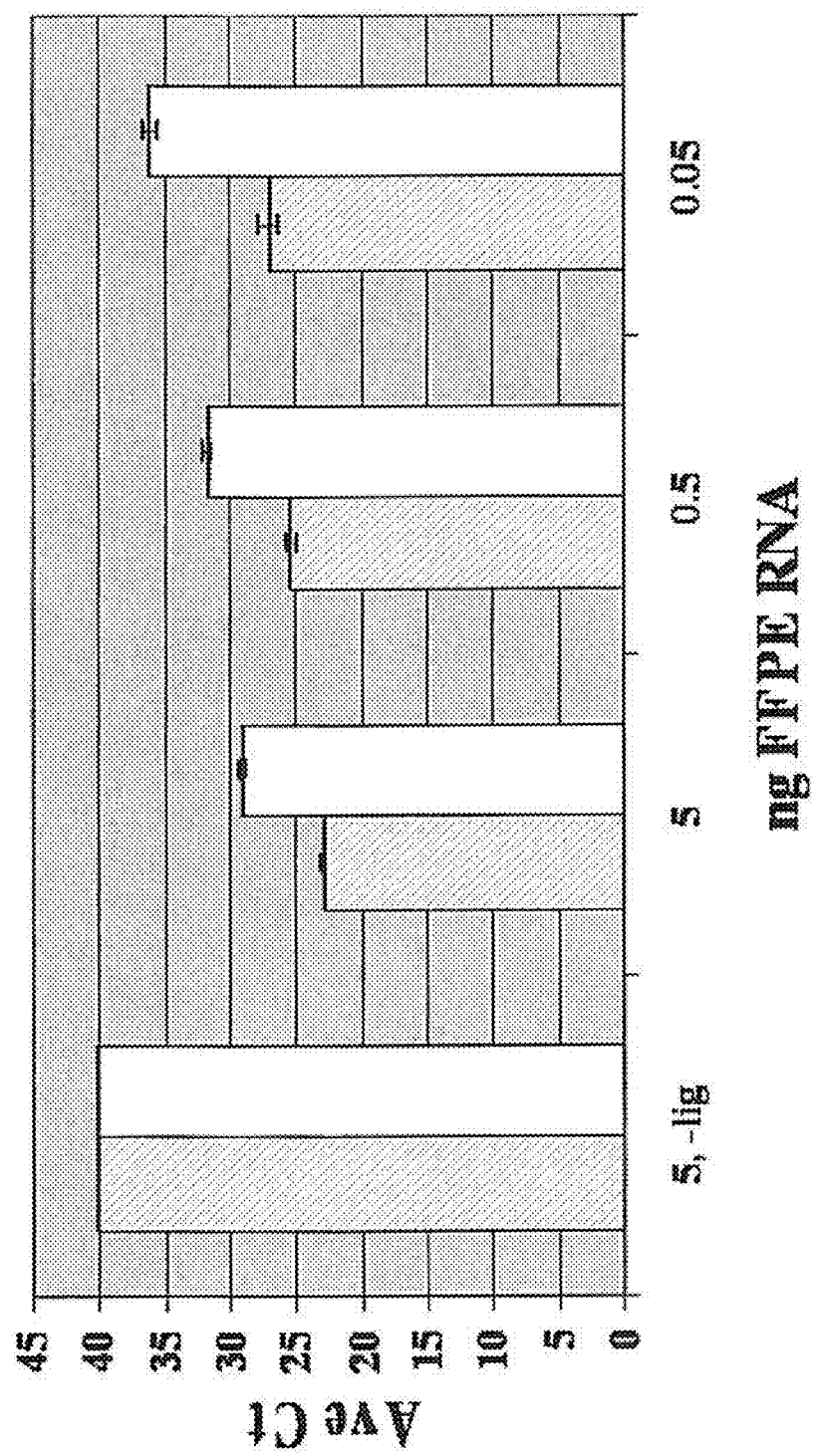

FIG. 9A-FIG. 9B provide results comparing standard qRT-PCR (open bars) to one ligation-enhanced nucleic acid detection assay embodiment (\\\) for detection of β-actin mRNA for a 2-yr old archived FFPE colon sample (FIG. 9A) and a 13-yr old archived FFPE colon sample (FIG. 9B). The x-axis represents nanograms of FFPE RNA; "-lig" refers to a ligase-negative control. The y-axis is average Ct, cycle threshold.

Figure 10A:
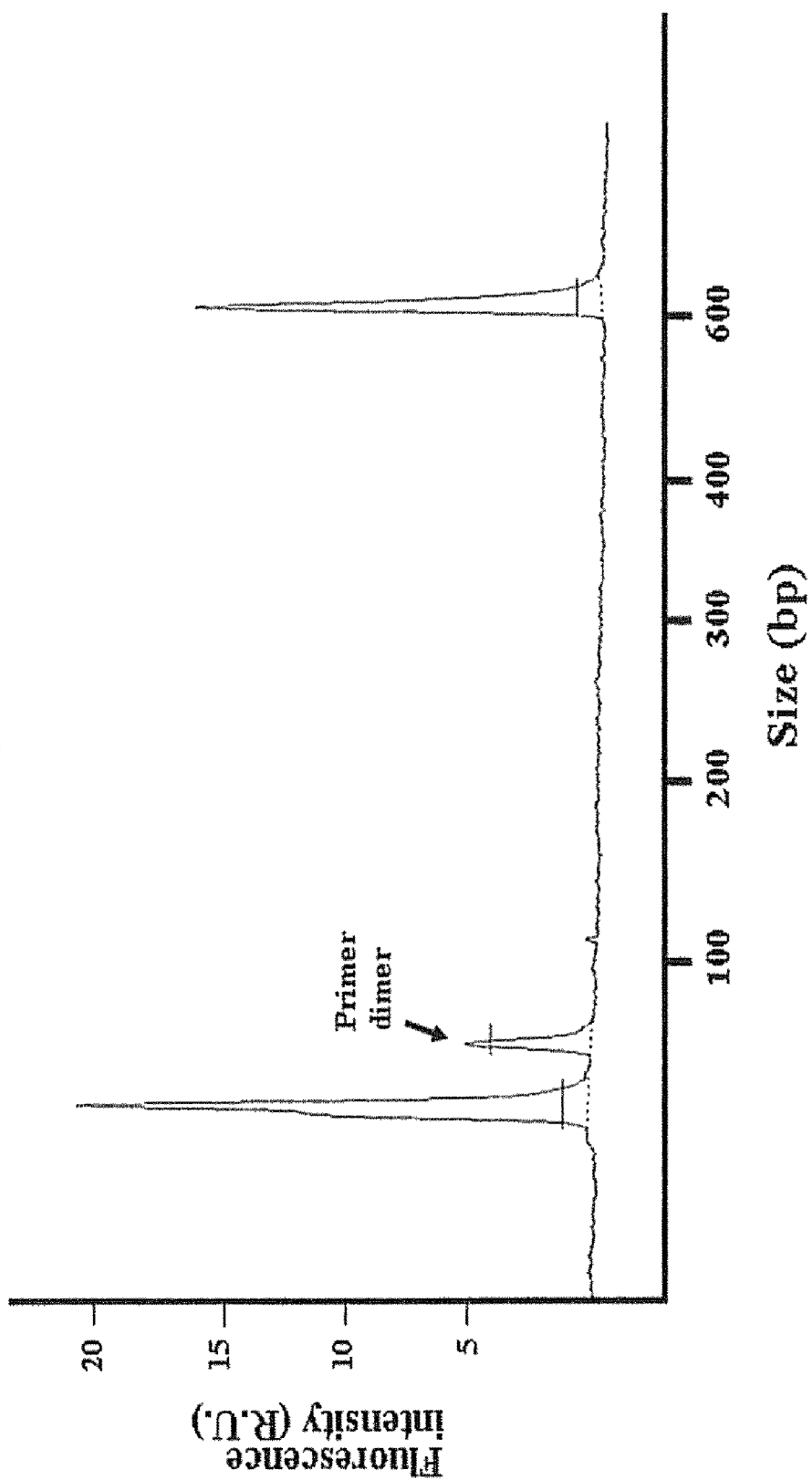
Figure 10B:
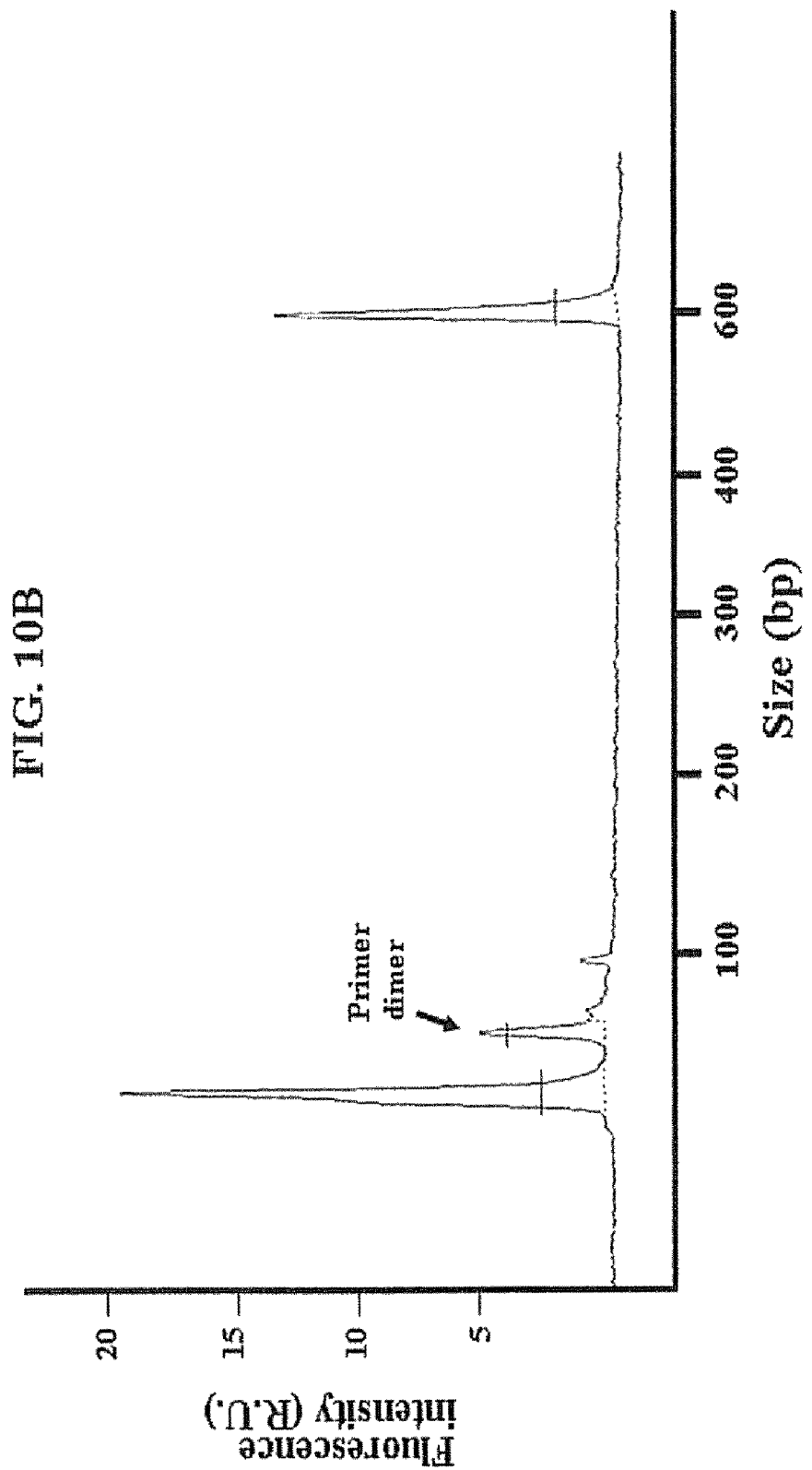
Figure 10C:
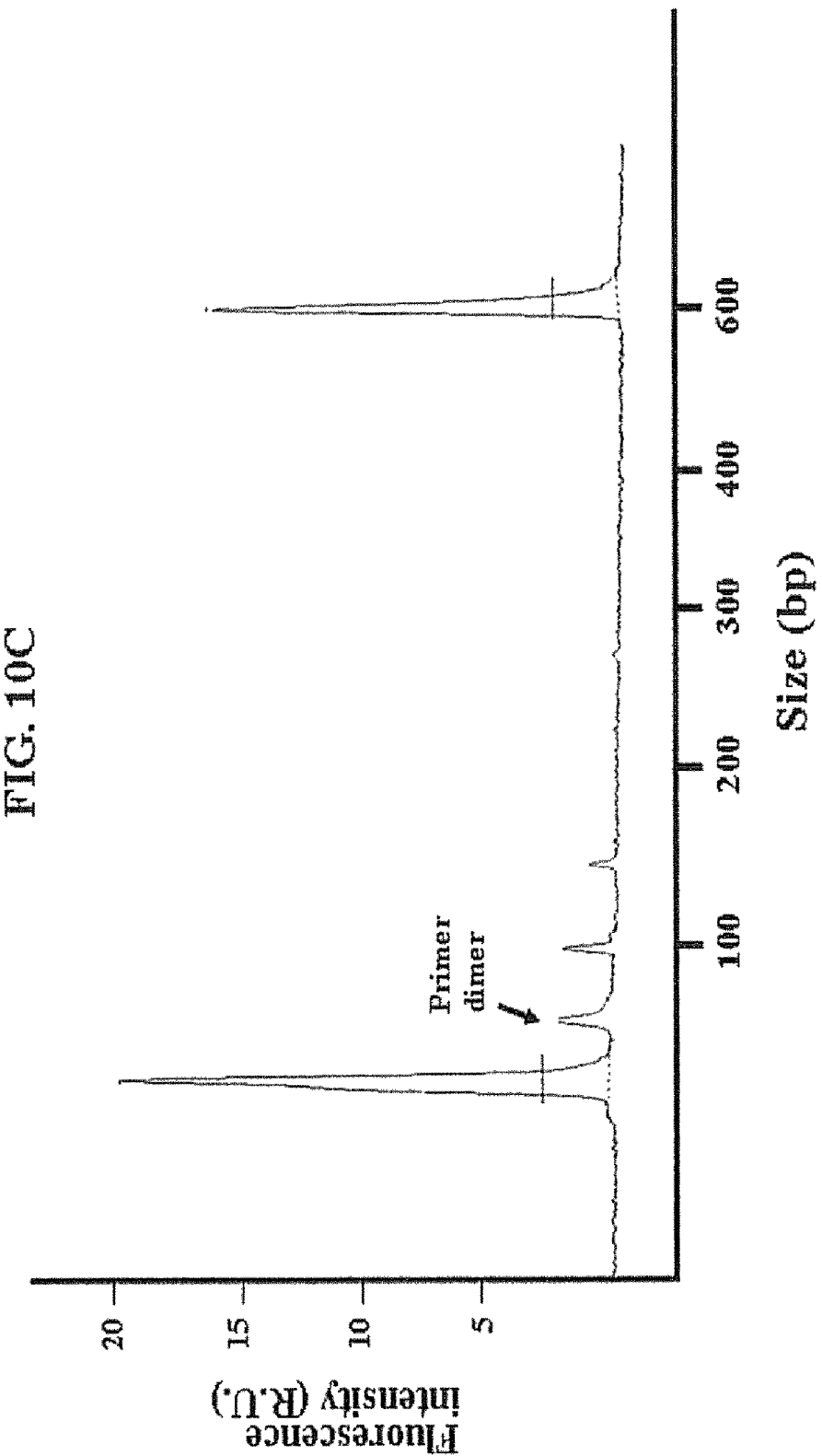
Figure 10D:
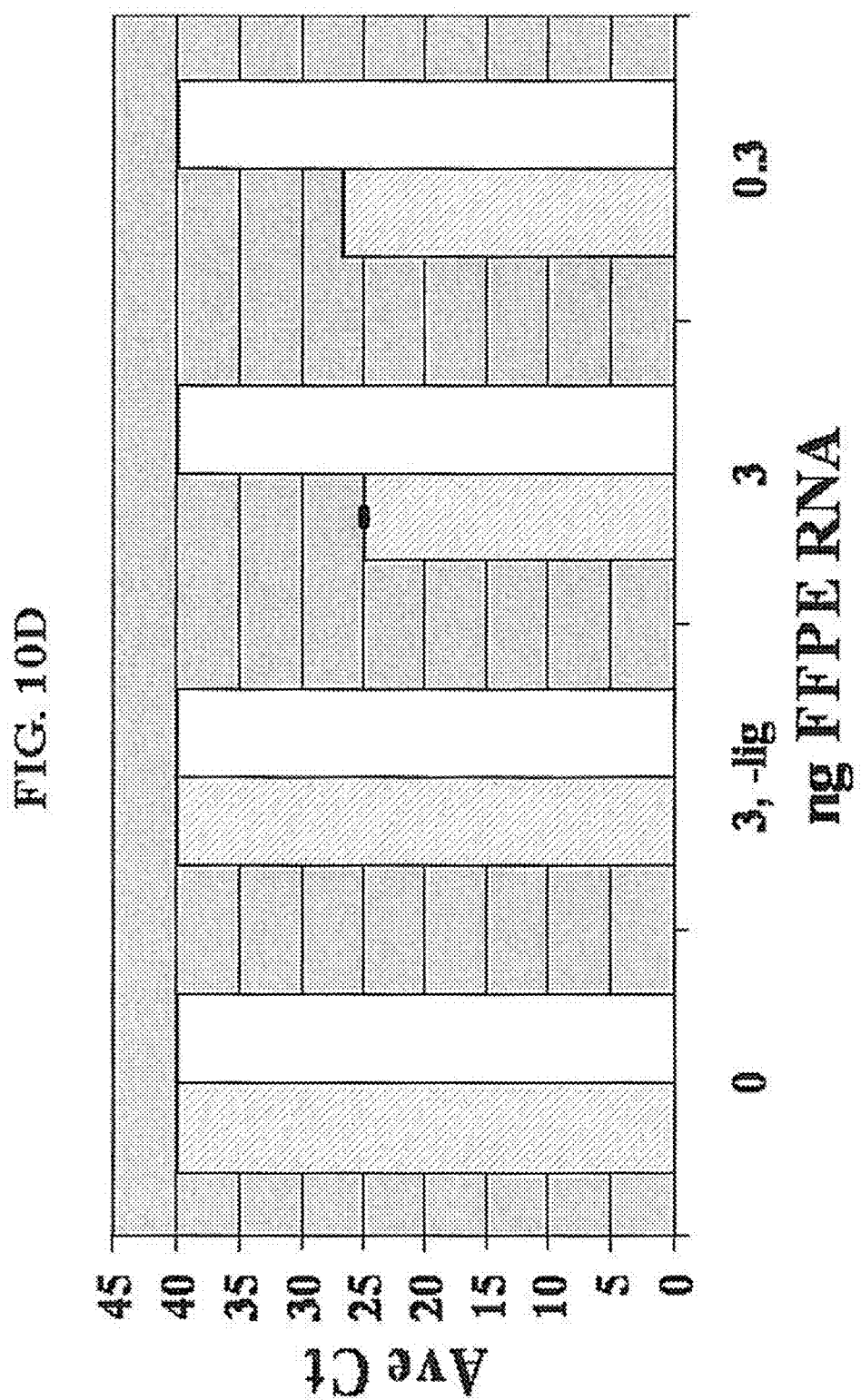
Figure 10E:
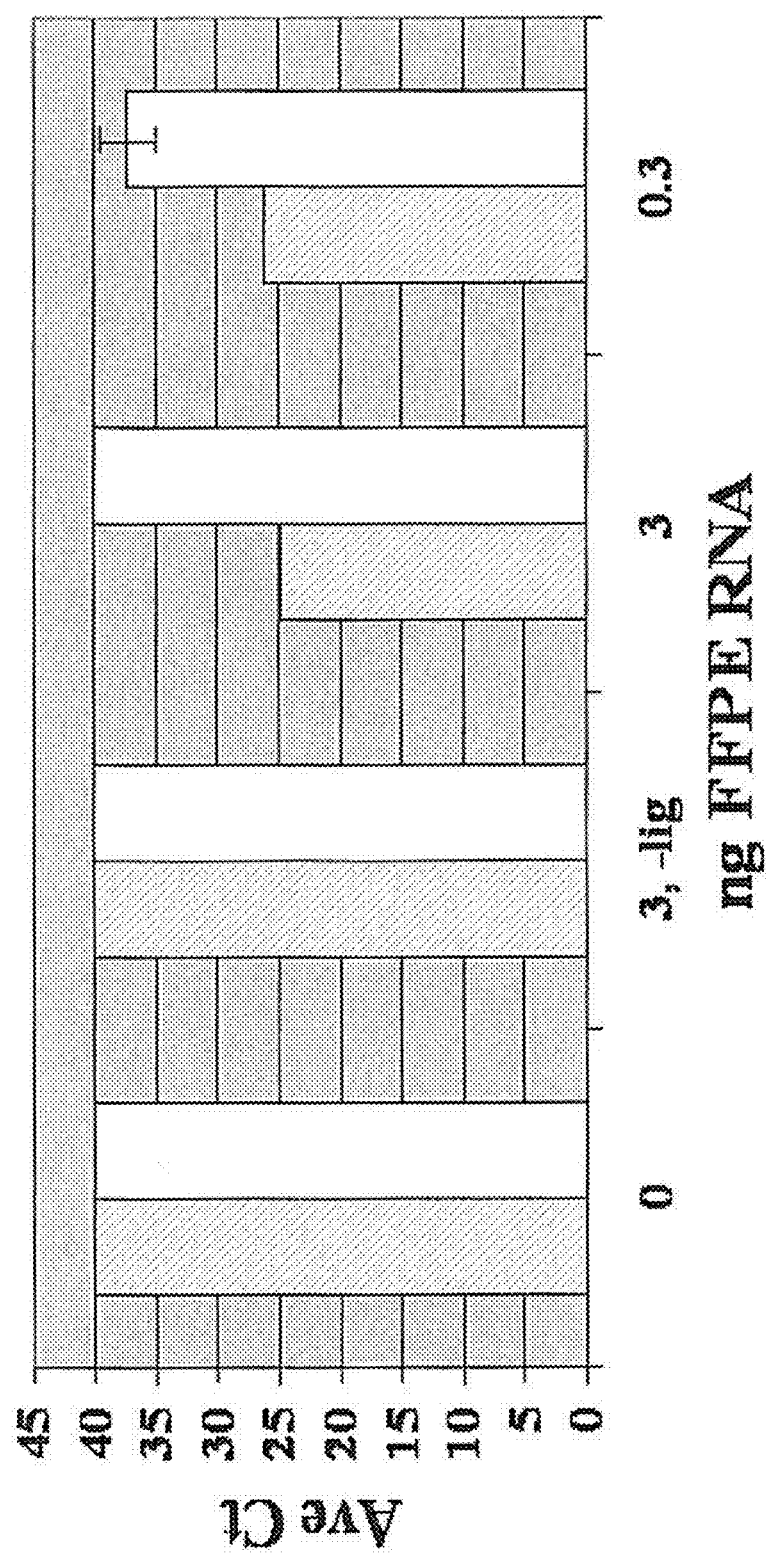
Figure 10F:
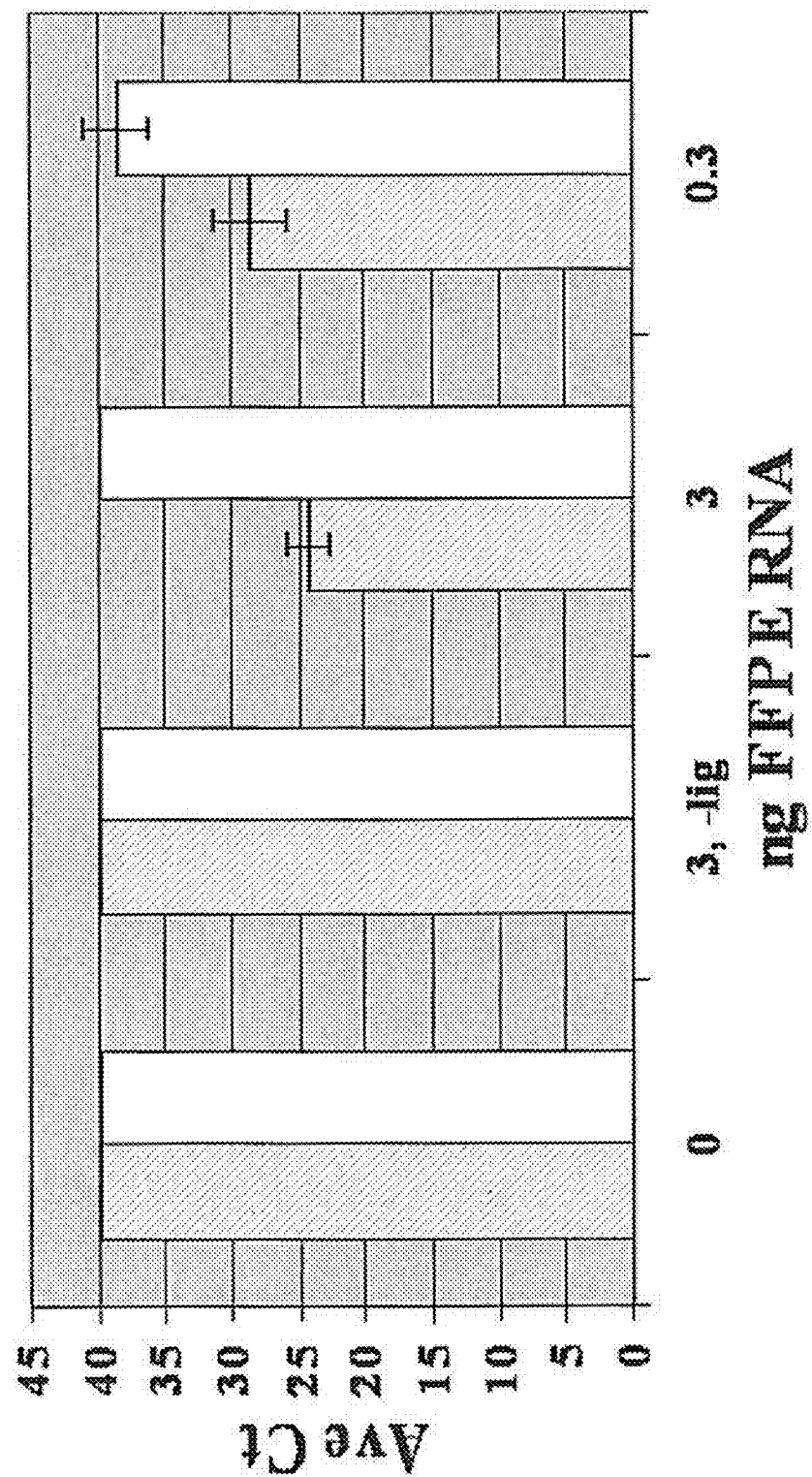

FIG. 10A-FIG. 10F. FIG. 10A-FIG. 10C provide results of integrity assays comparing amplified products for three archived FFPE tissue samples as described in Example 3. That the RNA in the samples was compromised is evident from the tracings since essentially no RNA bands are present other than the PCR primer band at 38 base pairs. The y-axis represents fluorescence intensity in relative units; the x-axis represents size in base pairs. FIG. 10D-FIG. 10F provide results comparing detection of β-actin mRNA using standard qRT-PCR (open bars) to one ligation-enhanced nucleic acid detection assay embodiment (\\\) for the three compromised samples of FIG. 10A-FIG. 10C, respectively. The x-axis represents nanograms of FFPE RNA; "-lig" refers to a ligase-negative control. The y-axis is average Ct, cycle threshold.

Figure 11A:
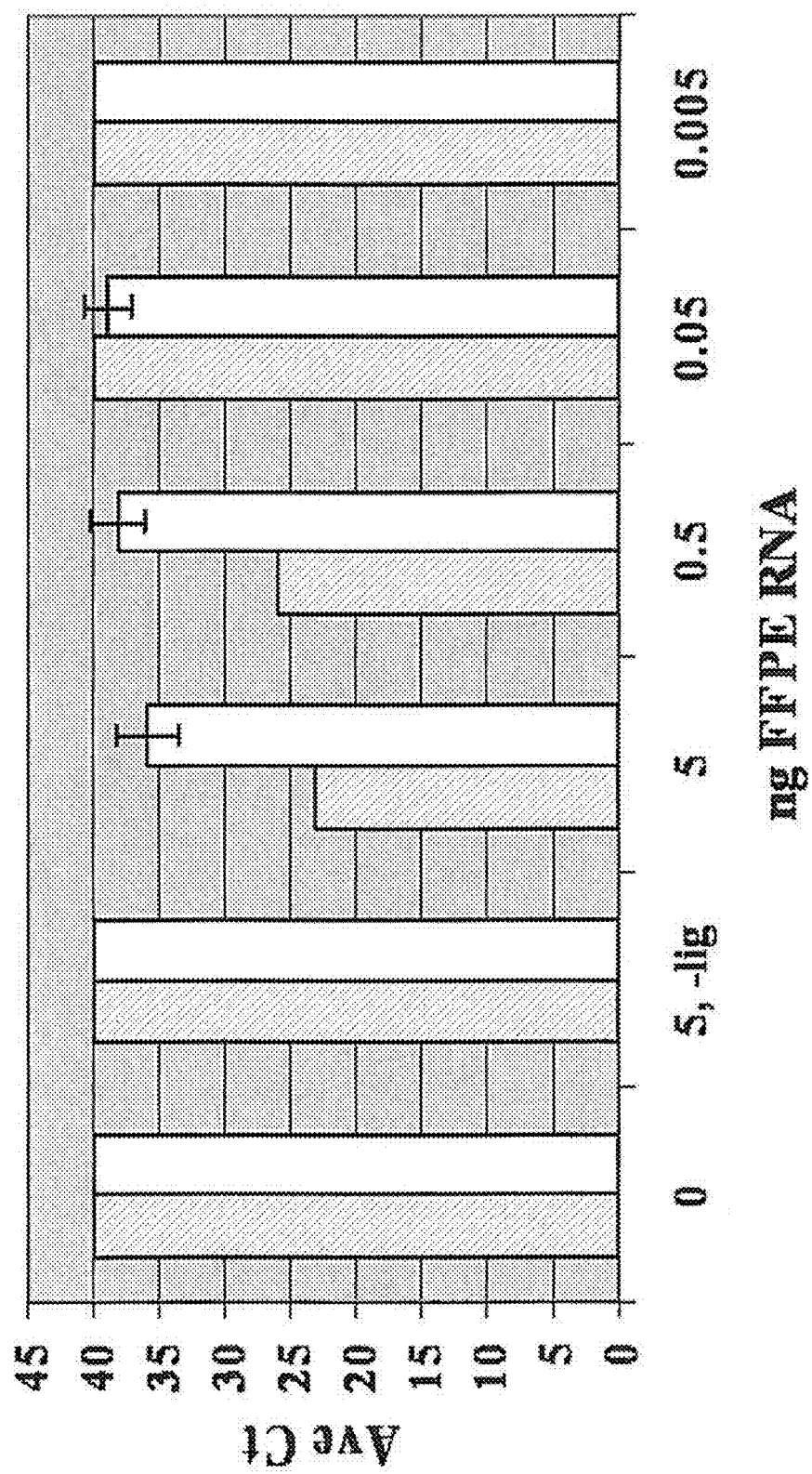
Figure 11B:
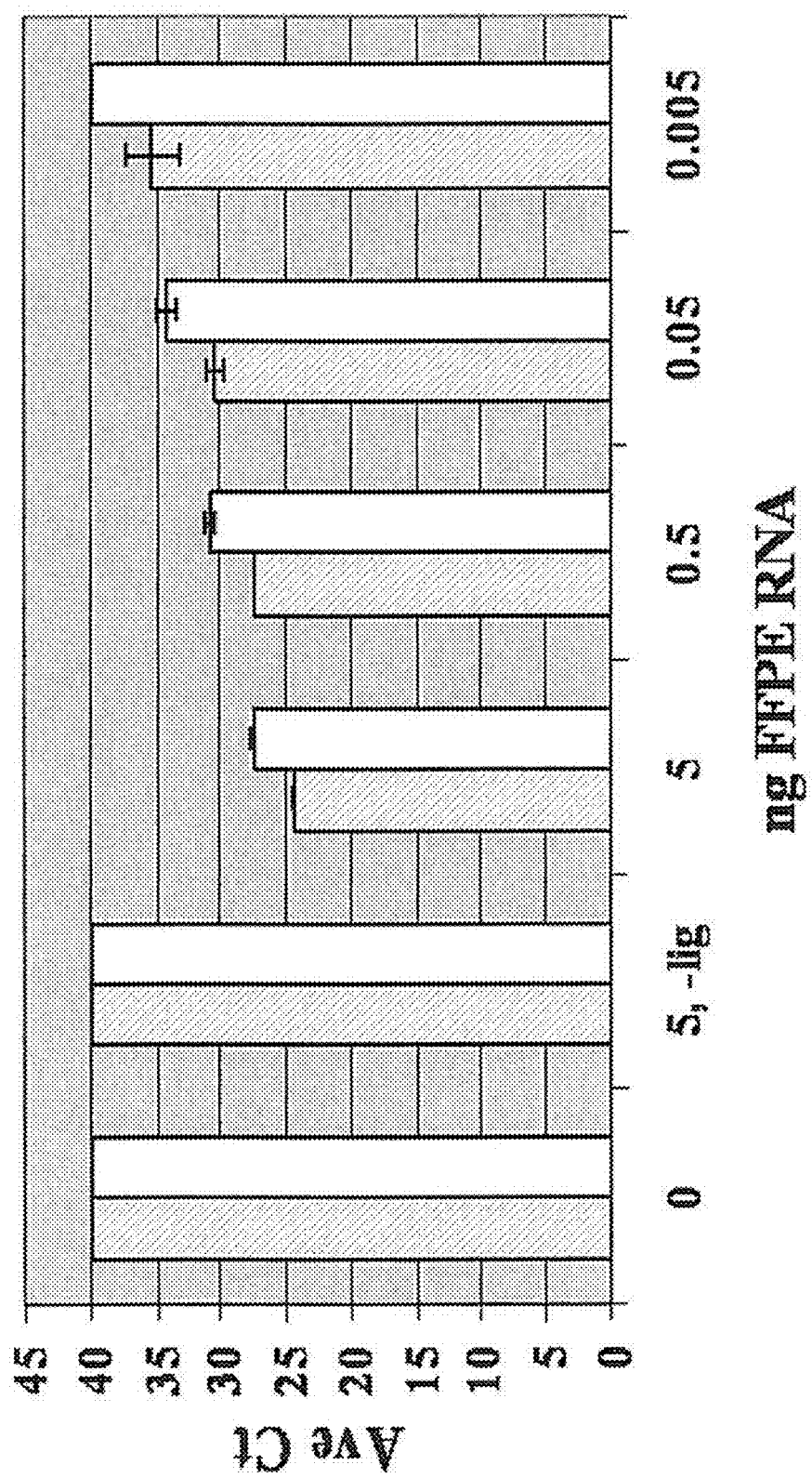
Figure 11C:
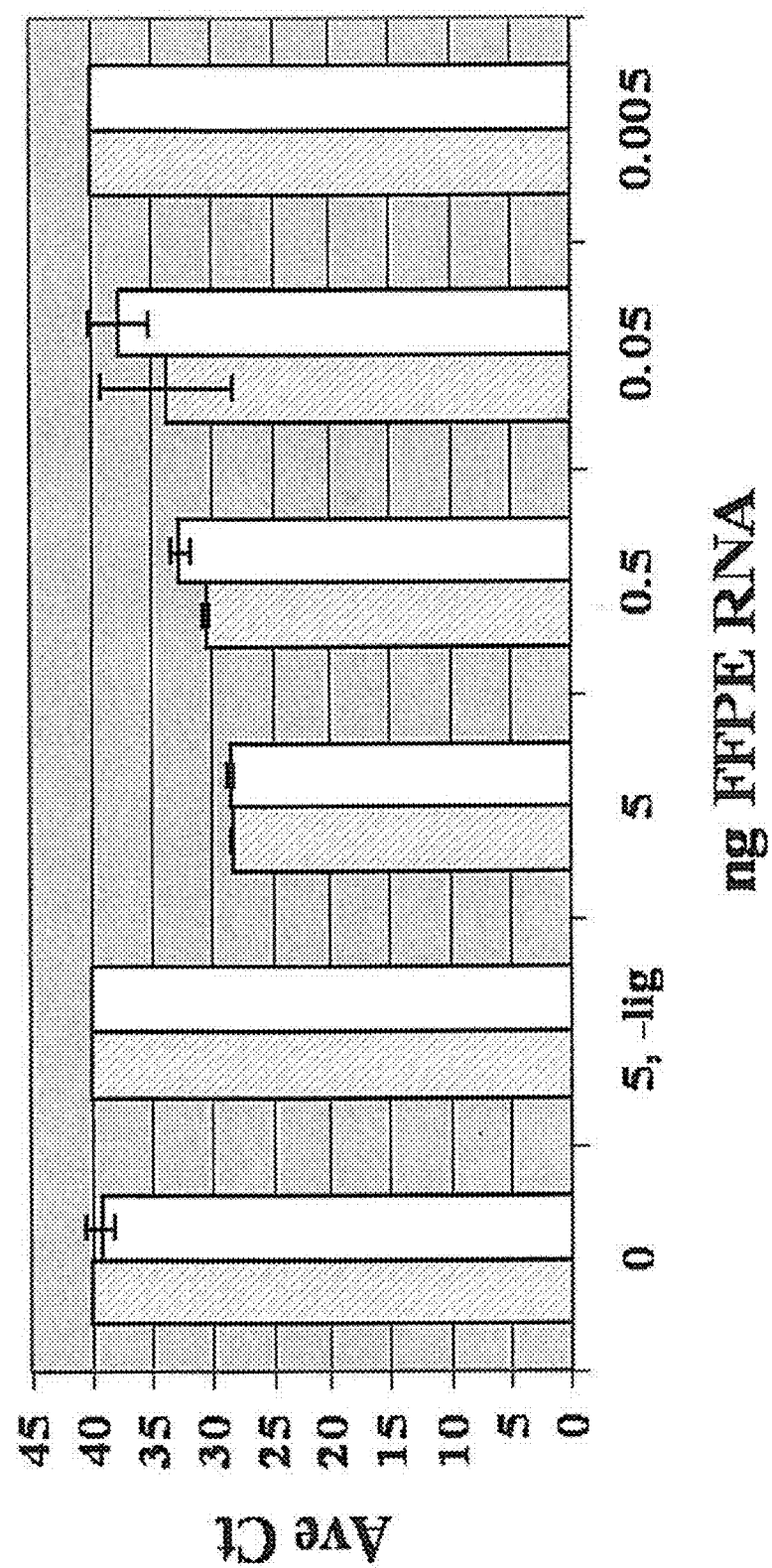

FIG. 11A-FIG. 11C provide detection results for three different target mRNAs from a 14-year old archived colon tissue block. The target mRNAs are β-actin mRNA (FIG. 11A), glyceraldehyde-3-phosphate dehydrogenase mRNA (FIG. 11B), and transferrin receptor mRNA (FIG. 11C). Traditional qRT-PCR (open bars) is compared to one ligation-enhanced nucleic acid detection assay embodiment (\\\). The x-axis represents nanograms of FFPE RNA; "-lig" refers to a ligase-negative control. The y-axis is average Ct, cycle threshold.

Figure 12A:
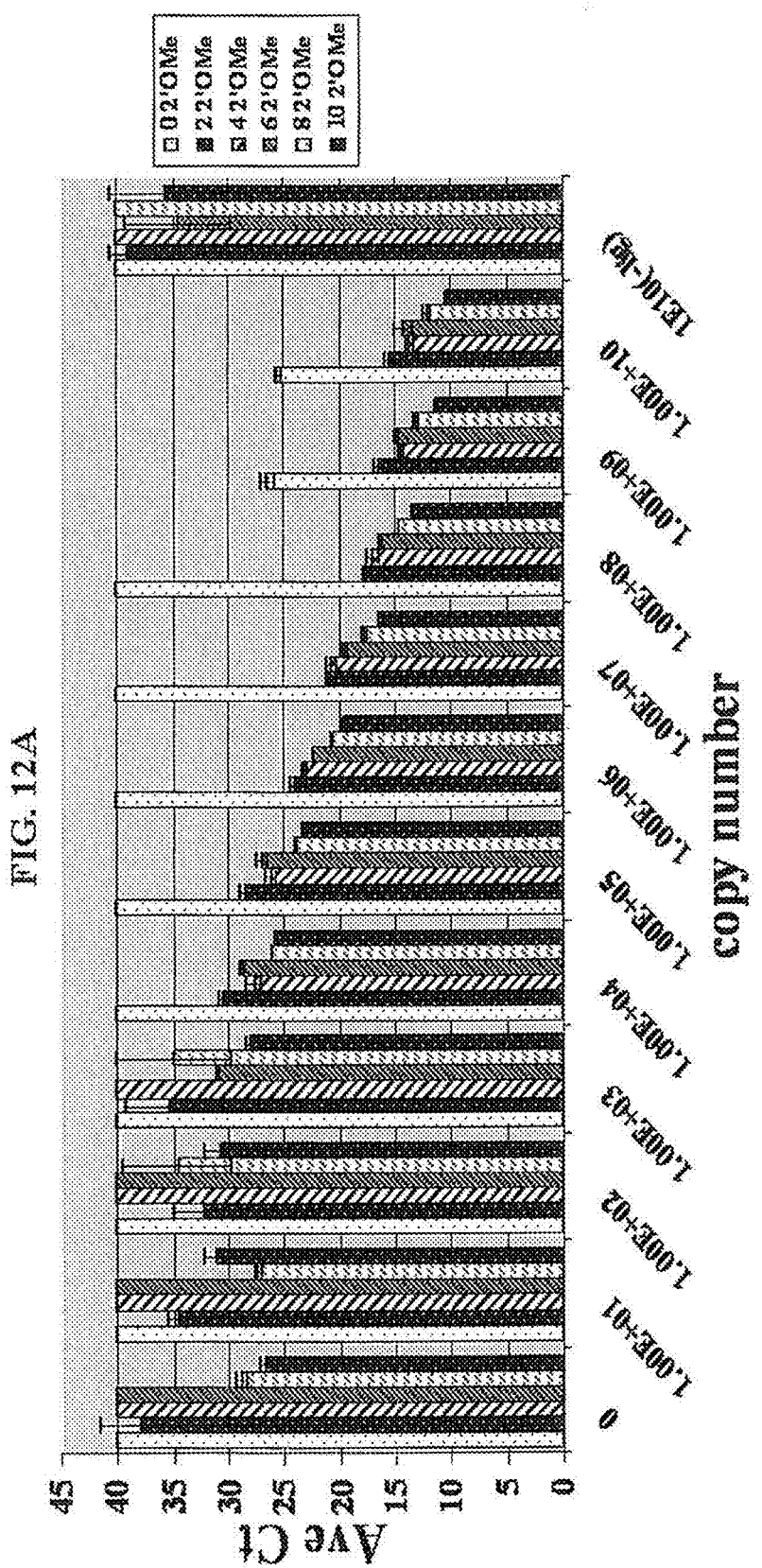
Figure 12B:
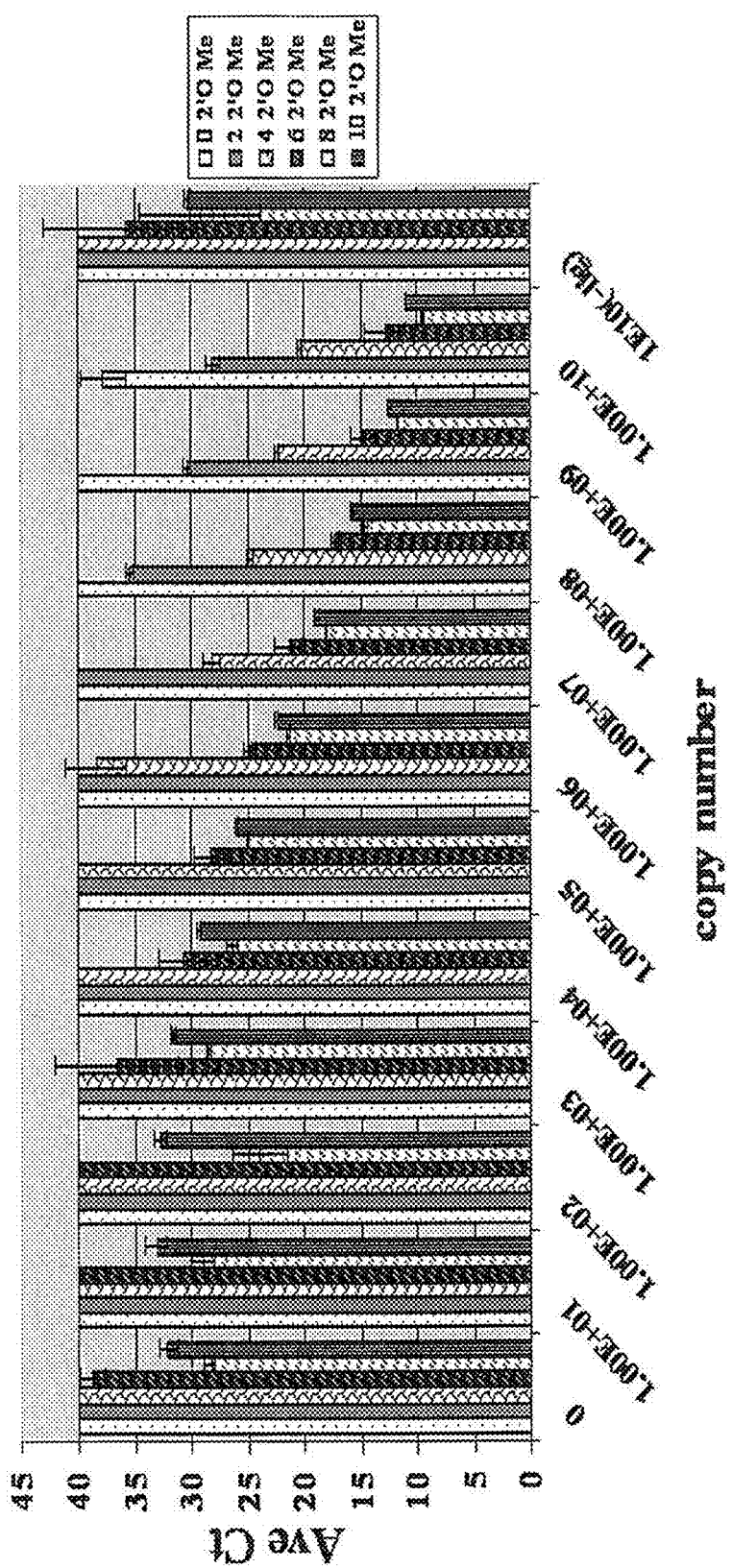

FIG. 12A-FIG. 12B provide results on the effect of including nucleotide analogs in the chimeric oligonucleotide probes of one ligation-enhanced, nucleic acid detection assay embodiment. Probes were designed to contain 0, 2, 4, 6, 8 or 10 contiguous nucleotide analogs (in these exemplary embodiments, the nucleotide analog contained a 2'-OR group where R is $CH_3$) within each target-specific portion proximal to each respective primer-specific portion. Results for the human β-glucuronidase (GUSB) probes are provided by FIG. 12A and for the β-actin probes by FIG. 12B. The x-axis represents copy number of synthetic target RNA having a length of 25 nucleotides; "-lig" refers to a ligase-negative control. The y-axis is average Ct, cycle threshold.

Figure 13A:
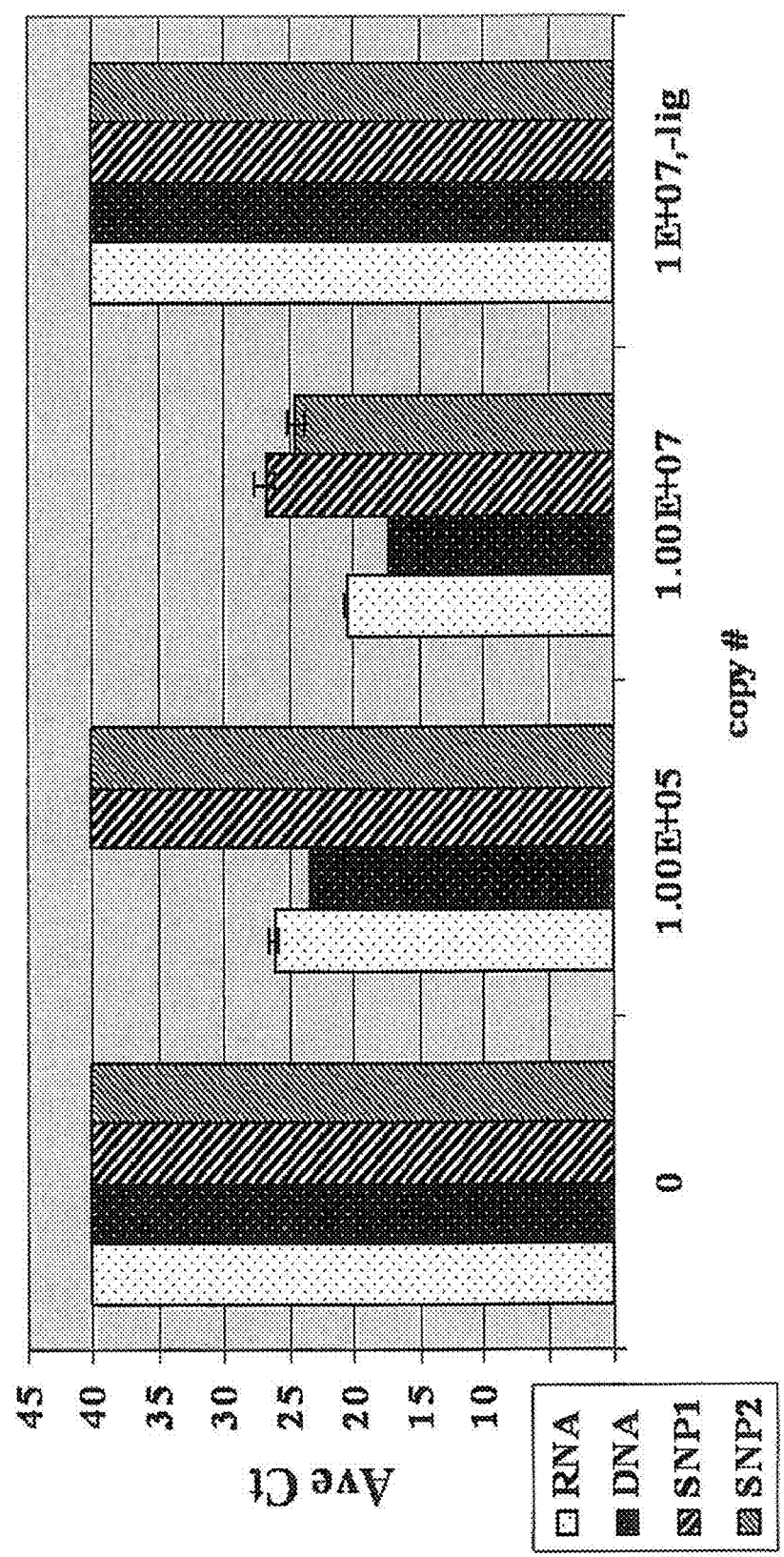
Figure 13B:
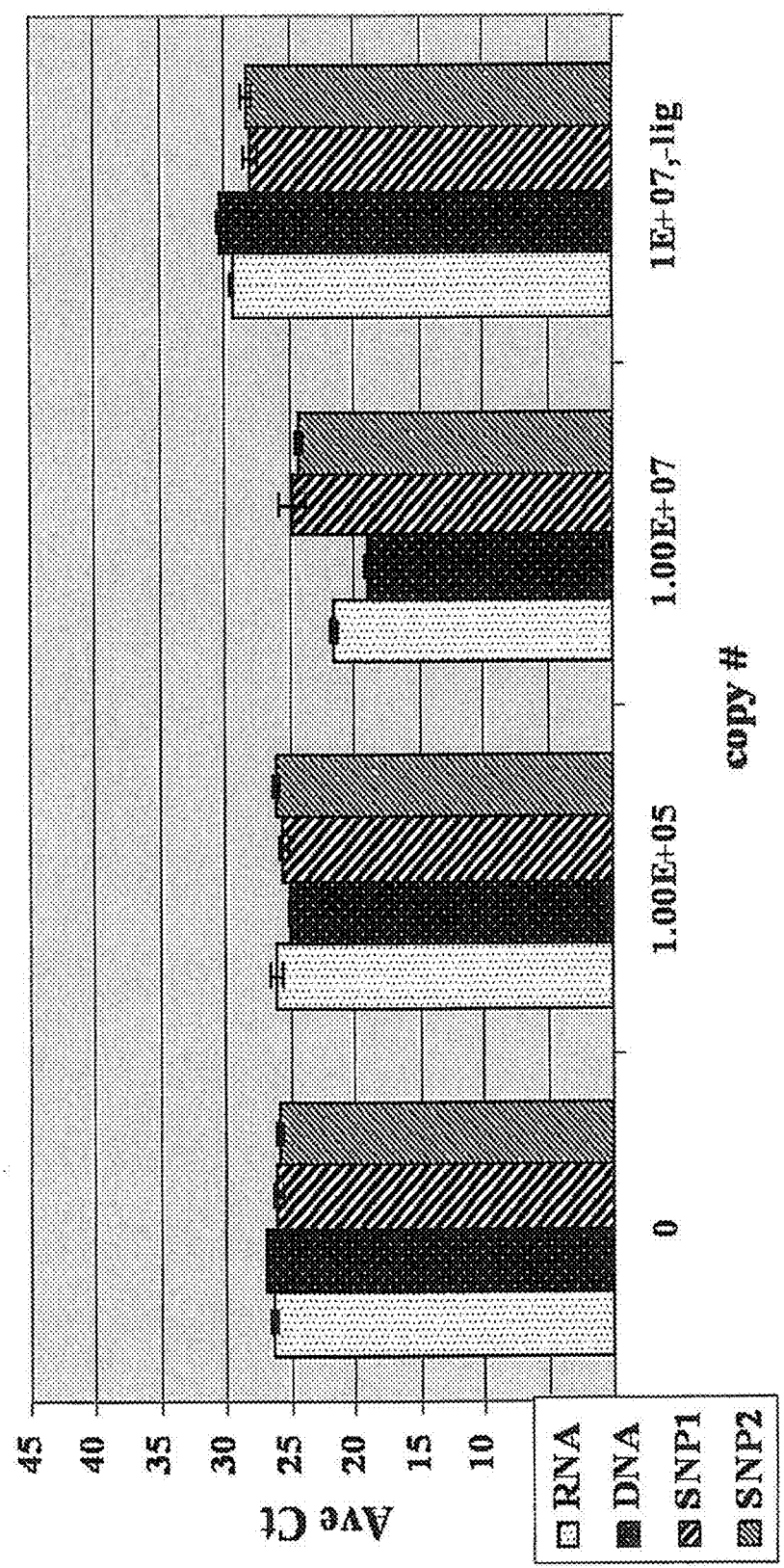
Figure 13C:
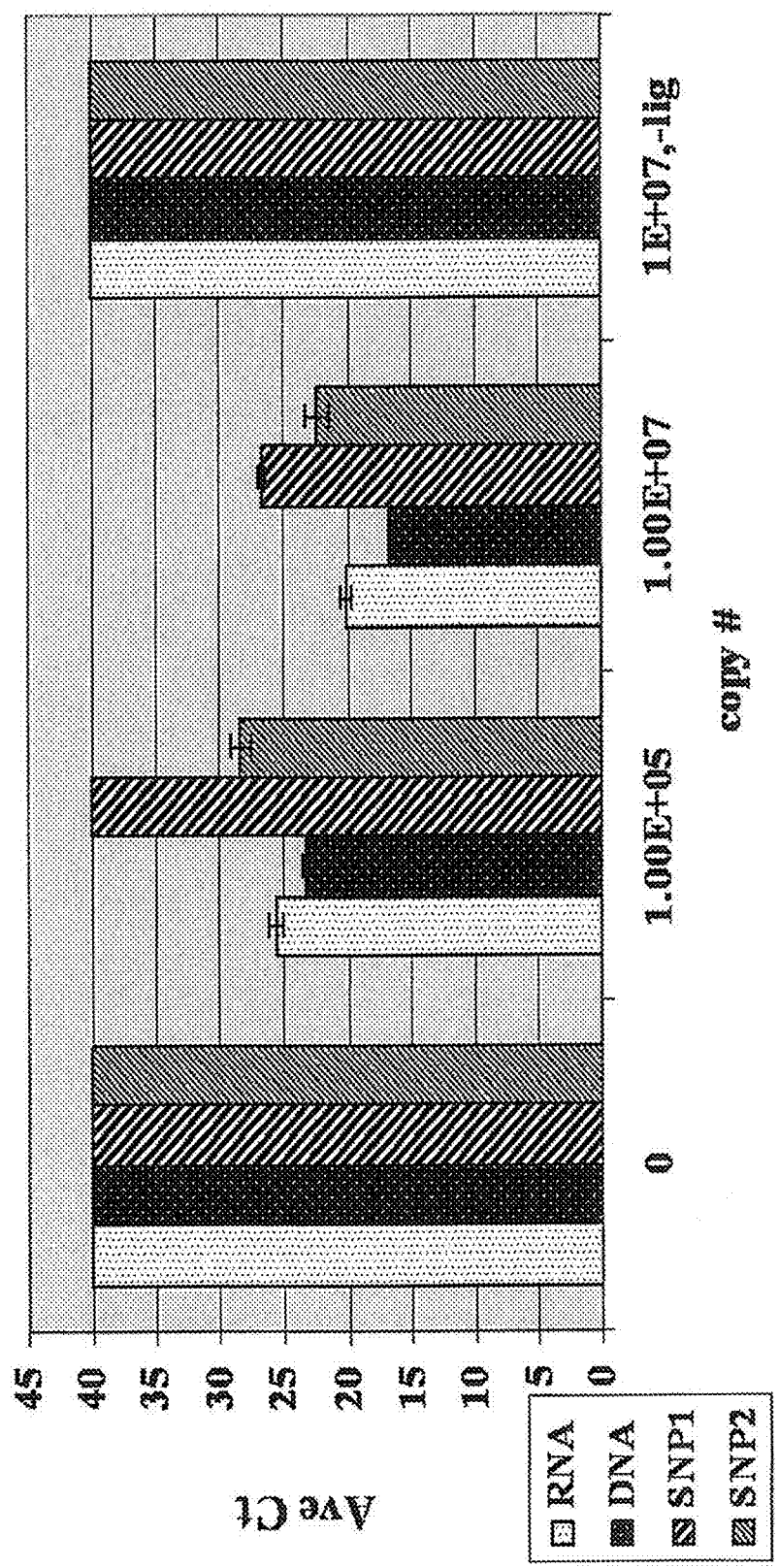
Figure 13D:
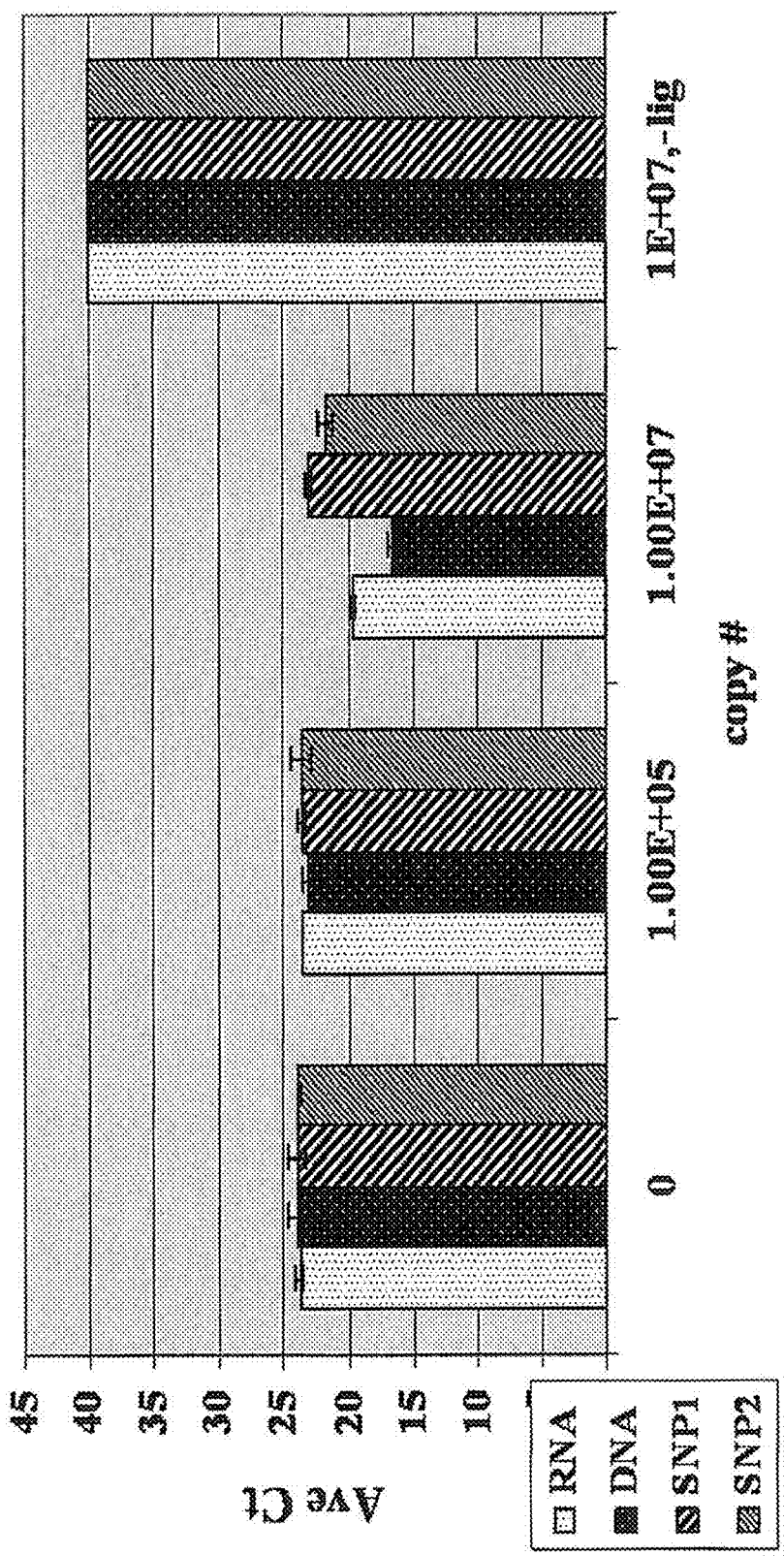

FIG. 13A-FIG. 13D provide results demonstrating detection of a single nucleotide polymorphism present at two different locations (SNP1 and SNP2) of both a target synthetic DNA sequence (total length=25 nucleotides) and a target synthetic RNA sequence (total length=25 nucleotides) for GUSB and β-actin using one ligation-enhanced nucleic acid detection assay embodiment. FIG. 13A and FIG. 13B provide results for β-actin with and without RNase treatment, respectively; FIG. 13C and FIG. 13D provide results for GUSB with and without RNase treatment, respectively. The x-axis represents copy number of synthetic target nucleic acid; "-lig" refers to a ligase-negative control. The y-axis is average Ct, cycle threshold.

REFERENCE NUMBERS OF DRAWINGS

1. Primer-specific portion of first chimeric oligonucleotide probe
2. Target-specific portion of second chimeric oligonucleotide probe
2a. First portion of target-specific portion 2
2b. Second portion of target-specific portion 2
3. Target-specific portion of first chimeric oligonucleotide probe
3a. First portion of target-specific portion 3
3b. Second portion of target-specific portion 3
4. Primer-specific portion of second chimeric oligonucleotide probe
5. 3'-Penultimate nucleotide of target-specific portion 3
5'. Nucleotide of target nucleic acid complementary to nucleotide 5
6. 5'-Terminal phosphate of 5'-terminal nucleotide of 2
7. 3'-Terminal nucleotide of target-specific portion 3

7'. Nucleotide of target nucleic acid complementary to nucleotide 7
8. DNA Target nucleic acid
9. 3'-OH group of 3'-terminal nucleotide 7
10. RNA Target nucleic acid
11. Detector probe sequence
12. RNase-treated RNA target
14. Reverse transcription primer sequence
21. First (forward) amplification primer
31. Detector probe having a fluorophore F and a quencher Q attached thereto
41. Second (reverse) amplification primer
51. Direction of reverse transcription of ligated product
52. Target-specific portion of probe 502 or of probe 512
52a. First portion of target-specific portion 52
52b. Second portion of target-specific portion 52
53. Target-specific portion of probe 501
53a. First portion of target-specific portion 53
53b. Second portion of target-specific portion 53
54. Primer-specific portion of probe 502 or of probe 512
55. Target-specific portion of probe 511
55a. First portion of target-specific portion 55
55b. Second portion of target-specific portion 55
56. SNP-detector nucleotide of probe 502 or of probe 512
57. SNP-detector nucleotide of probe 501 or of probe 511
58. Target-specific portion of probe 512
58a. First portion of target-specific portion 58
58b. Second portion of target-specific portion 58
59. Primer-specific portion of probe 501 or of probe 511
61. 5'-Terminal nucleotide of medial probe
62. 5'-Terminal nucleotide of 3'-most chimeric oligonucleotide probe
91. 3'-Terminal nucleotide of 5'-most oligonucleotide probe
92. 3'-Terminal nucleotide of medial probe
101. First chimeric oligonucleotide probe
102. Second chimeric oligonucleotide probe
103. Annealed product
104. A nick at the junction of annealed chimeric oligonucleotide probes 101 and 102
105. Ligated and RNase-treated product
106. Ligated target-specific portions
107. Unligated, RNase-treated probe products
108. Annealed, gap-filled product
109. Product 105 annealed to primers 21 and 41 and to detectable probe 31
129. Gap between annealed first and second chimeric oligonucleotide probes
300. Medial probe
301. First or 5'-most chimeric oligonucleotide probe
302. Second or 3'-most chimeric oligonucleotide probe
303. Annealed product of a plurality of probes with target nucleic acid
305. Ligated product of 303
306. Ligated target-specific portions of 305
400. Single chimeric oligonucleotide probe
403. Annealed nicked circular duplex of 400 and target nucleic acid
404. Nick present in annealed circular duplex 403
405. Ligated product
406. Ligated target-specific portions
407. Unligated, RNase-treated probe product
501. First SNP-detector probe for 503/513 assay; First chimeric oligonucleotide probe for 503/523 assay
502. First SNP-detector probe for 503/523 assay; Second chimeric oligonucleotide probe for 503/513 assay
503. Detection embodiment for single nucleotide polymorphisms 517 and 519
511. Second SNP-detector probe for 503/513 assay
512. Second SNP-detector probe for 503/523 assay
513. Detection embodiment for single nucleotide polymorphism 517
515. Target nucleic acid containing a single nucleotide polymorphism 517 or 519
517. Nucleotide position of a single nucleotide polymorphism
519. Further nucleotide position of a single nucleotide polymorphism
523. Detection embodiment for single nucleotide polymorphism 519

DESCRIPTION OF VARIOUS EMBODIMENTS

It is to be understood that both the foregoing general description and the following detailed description are exemplary and, explanatory only and are not intended to limit the scope of the current teachings. In this application, the use of the singular includes the plural unless specifically stated otherwise. For example, "at least one first chimeric oligonucleotide probe" means that more than one first chimeric oligonucleotide primer can be present; for example, one or more copies of a particular first chimeric oligonucleotide probe species, as well as one or more different first chimeric oligonucleotide probe species. Also, the use of "comprise", "contain", and "include", or modifications of those root words, for example but not limited to, "comprises", "contained", and "including", are not intended to be limiting. Use of "or" means "and/or" unless stated otherwise. The term "and/or" means that the terms before and after can be taken together or separately. For illustration purposes, but not as a limitation, "X and/or Y" can mean "X" or "Y" or "X and Y".

Whenever a range of values is provided herein, the range is meant to include the starting value and the ending value and any value or value range there between unless otherwise specifically stated. For example, "from 0.2 to 0.5" means 0.2, 0.3, 0.4, 0.5; ranges there between such as 0.2-0.3, 0.3-0.4, 0.2-0.4; increments there between such as 0.25, 0.35, 0.225, 0.335, 0.49; increment ranges there between such as 0.26-0.39; and the like.

The section headings used herein are for organizational purposes only and are not to be construed as limiting the subject matter described in any way. All literature and similar materials cited in this application including, but not limited to, patents, patent applications, articles, books, treatises, and interne web pages, regardless, of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The term "or combinations thereof" as used herein refers to all permutations and combinations of the listed items, preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context. The term "surrogate" as used herein means a product that is indicative of presence of another product. For example, an amplification product is a surrogate for a nucleic acid that has been amplified.

Nucleotide: The term "nucleotide" generally refers to a phosphate ester of a nucleoside, either as a monomer or within a dinucleotide, oligonucleotide or polynucleotide. A nucleoside generally is a purine base or a pyrimidine base linked to the C-1' carbon of a ribose (a ribonucleoside) or of a deoxyribose (deoxyribonucleoside). Naturally occurring purine bases generally include adenine (A) and guanine (G). Naturally occurring pyrimidine bases generally include cytosine (C), uracil (U) and thymine (T). When the nucleoside base is a purine, the ribose or deoxyribose is attached to the nucleobase at the 9-position of the purine, and when the nucleobase is a pyrimidine, the ribose or deoxyribose is attached to the nucleobase at the 1-position of the pyrimidine. A ribonucleotide is a phosphate ester of a ribonucleoside and a deoxyribonucleotide is a phosphate ester of a deoxyribonucleoside. The term "nucleotide" is generic to both ribonucleotides and deoxyribonucleotides. A dinucleotide generally has two nucleotides covalently bonded via a 3'-5' phosphodiester linkage. An oligonucleotide generally has more than two nucleotides and a polynucleotide generally refers to polymers of nucleotide monomers.

Nucleotide monomers are linked by "internucleotide linkages," e.g., phosphodiester linkages where, as used herein, the term "phosphodiester linkage" refers to phosphodiester bonds or bonds including phosphate analogs thereof, including associated counterions, e.g., $H^+$, $NH_4^+$, $Na^+$, if such counterions are present. Whenever an oligonucleotide is represented by a sequence of letters, such as "AUGCCUG," it will be understood that the nucleotides are in 5' to 3' order from left to right unless otherwise noted or it is apparent to the skilled artisan from the context that the converse was intended. Descriptions of how to synthesize oligonucleotides can be found, among other places, in U.S. Pat. Nos. 4,373,071; 4,401,796; 4,415,732; 4,458,066; 4,500,707; 4,668,777; 4,973,679; 5,047,524; 5,132,418; 5,153,319; and 5,262,530. Oligonucleotides can be of any length.

Base Pairing: "Base pairing," as used herein, includes both standard Watson-Crick base pairing and Hoogsteen-type hydrogen bonding. Base pairings found commonly in double-stranded (duplex) nucleic acids are G:C, A:T, and A:U. Such base pairs are referred to as complementary base pairs and one base is complementary to its paired base. Nucleotide analogs as described infra are also capable of forming hydrogen bonds when paired with a complementary nucleotide or nucleotide analog.

Complementary or Substantially Complementary: As used herein, the terms "complementary" or "complementarity" are used not only in reference to base pairs but also in reference to anti-parallel strands of oligonucleotides related by the Watson-Crick (and optionally Hoogsteen-type) base-pairing rules, to nucleic acid sequences capable of base-pairing according to the standard complementary rules, or being capable of hybridizing to a particular nucleic acid segment under relatively stringent conditions. For example, the sequence 5'-AGTTC-3' is complementary to the sequence 5'-GAACT-3'. The terms "completely complementary" or "100% complementary" and the like refer to complementary sequences that have perfect pairing of bases between the anti-parallel strands (no mismatches in the polynucleotide duplex). Nucleic acid polymers can be complementary across only portions of their entire sequences. The terms "partial complementarity," "partially complementary," "incomplete complementarity" or "incompletely complementary" and the like refer to any alignment of bases between anti-parallel polynucleotide strands that is less than 100% perfect (e.g., there exists at least one mismatch in the polynucleotide duplex). Furthermore, two sequences are said to be complementary over a portion of their length if there exists one or more mismatches, gaps or insertions in their alignment. A single-stranded nucleic acid "complement" refers a single nucleic acid strand that is complementary or partially complementary to a given single nucleic acid strand.

Furthermore, a "complement" of a target polynucleotide refers to a polynucleotide that can combine (e.g., hybridize) in an anti-parallel association with at least a portion of the target polynucleotide. The anti-parallel association can be intramolecular, e.g., in the form of a hairpin loop within a nucleic acid molecule, or intermolecular, such as when two or more single-stranded nucleic acid molecules hybridize with one another.

Hybridization or Annealing: The terms "hybridization, hybridize, annealing, anneal or variations thereof" are used interchangeably and refer to the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C. In certain embodiments, base-stacking and hydrophobic interactions can also contribute to duplex stability. Conditions under which nucleic acid sequences anneal to complementary or substantially complementary sequences are Well known in the art, e.g., as described in Tijssen (1993) *Laboratory Techniques in Biochemistry and Molecular Biology*—Hybridization with Nucleic Acid Probes part I chapter 2, "Overview of principles of hybridization and the strategy of nucleic acid probe assays," (Elsevier, N.Y.); in Ausubel (Ed.) *Current Protocols in Molecular Biology*, Volumes I, II, and III, 1997; and in Hames and Higgins (1995) Gene Probes 1 and Gene Probes 2, IRL Press at Oxford University Press, Oxford, England.

In general, annealing is influenced by, among other things, the length of the complementary portion of the sequences, pH, temperature, presence of mono- and divalent cations, the proportion of G and C nucleotides in the hybridizing region, the viscosity of the medium, and the presence of denaturants. Such variables influence the time required for hybridization. The presence of nucleotide analogs as described infra in the complementary portions of the nucleic acid sequences can also influence hybridization conditions. Thus, annealing conditions depend upon the particular application and are routinely determined by persons of ordinary skill in the art without undue experimentation. Annealing conditions are provided that allow first and second chimeric oligonucleotide probes to selectively hybridize to the target nucleic acid, but not hybridize to any significant degree to other nucleotides in the sample.

Denaturation: The terms "denaturing" or "denaturation" as used herein refer to any process in which a double-stranded oligonucleotide is converted to two single-stranded oligonucleotides. Denaturing a double-stranded oligonucleotide includes a variety of thermal or chemical techniques for denaturing a duplex, thereby releasing its two single-stranded components. Those of ordinary skill in the art will appreciate that the denaturing technique employed is generally not limiting unless it inhibits or appreciably interferes with, a subsequent amplifying, detecting, and/or quantifying step.

The term "corresponding to" when in reference to nucleic acids, means that a particular sequence is sufficiently complementary to an anti-parallel sequence such that the two sequences will anneal and form a duplex under stringent hybridization conditions. For example, a detector probe sequence that corresponds to a nucleic acid detector probe means that, under suitable hybridization conditions, the detector probe will specifically anneal to the detector probe sequence.

High stringency conditions could include about 50% formamide at 37° C. to 42° C. Reduced stringency conditions could occur at about 35° A) to 25 formamide at 30° C. to 35° C. Examples of stringency conditions for hybridization are provided in Sambrook, J., 1989, *Molecular Cloning: A Laboratory Manual*, Cold Spring Harbor Laboratory Press, Cold Spring Harbor, N.Y. Further examples of stringent hybridization conditions include. 400 mM NaCl, 40 mM PIPES pH 6.4, 1 mM EDTA, 50° C. or 70° C. for 12-16 hours, or hybridization at 70° C. in 1×SSC or 50° C. in 1×SSC, 50% formamide, or hybridization at 70° C. in 4×SSC or 50° C. in 4×SSC, 50% formamide. The temperature for hybridization is about 5-10 less than the melting temperature ($T_m$) of the duplex where $T_m$ is determined for duplexes between 19 and 49 base pairs in length using the following calculation: $T_m° C.=81.5+16.6 (\log_{10} [Na+])+0.41 (\% G+C)-(600/N)$ where N is the number of bases in the duplex, and [Na+] is the concentration of sodium ions in the hybridization buffer.

Nucleotide analogs: In certain embodiments, the present teachings comprise nucleotide analogs having enhanced affinity for base pairing as compared to non-modified nucleotides. The term, "nucleotide analogs," as used herein, refers to those nucleotide analogs that contribute to greater hybridization affinity than their naturally occurring non-modified nucleotide counterparts. Nucleotide analogs for embodiments can shift the conformation equilibrium toward the northern (C3'-endo) conformation consistent with the A-form geometry of RNA duplexes. DNA:RNA duplexes can also be stabilized thereby. In certain embodiments, contribution to greater hybridization affinity for base pairing is achieved by constructing oligonucleotide probe conformations favorable for hybrid formation, by improving base stacking by adding polarizable groups to the heterocycle, for example, by increasing the number of hydrogen bonds between base pairs, or by neutralizing the backbone charge, for example. Generally, electronegative substituents, i.e., substituents that tend to attract electrons, such as fluoro or alkoxy, at the 2' positions contribute to duplex stability by shifting the conformational equilibrium in the sugar moiety toward the C3'-endo conformation. Generally, non-electronegative groups at the 3'-position improve duplex stability and hybridization affinity. Hybridization affinity is the free energy difference between duplex and single strands at 37° C., referred to as $\Delta G°_{37}$, and can be evaluated using absorbance versus temperature profiles as known by one of ordinary skill in the art (e.g., see Freier et al., *Nucleic Acids Research* 25(22):4429-4443, 1997).

"Nucleotide analogs" in reference to nucleosides, nucleotides and/or oligonucleotides comprise synthetic analogs having modified nucleobase portions, modified pentose portions and/or modified phosphate portions, and, in the case of oligonucleotides, modified internucleotide linkages, as described generally elsewhere (e.g., Seheit, *Nucleotide Analogs* (John Wiley, New York, (1980); Englisch, *Angew. Chem. Int. Ed. Engl.* 30:613-29 (1991); Agrawal, *Protocols for Polynucleotides and Analogs*, Humana Press (1994)).

Exemplary nucleotide analogs that confer greater hybridization affinity include, without limitation:

a.) nucleotide analogs such as 2'-halo where halo is chloro, fluoro, bromo or iodo; 2'-O-alkyl where alkyl comprises lower alkyl such as methyl, ethyl, or propyl; 2'-O-$(CH_2)_4$ $NH_2$; 2'-O-anthraquinolylalkyl where alkyl comprises methyl or ethyl; 2'-O—$(CH_2)_2$—$OCH_3$; 2'-O—$(CH_2CH_2O)_n$—$CH_3$ where n is 1-4; 2'-O—$CH_2$—CHR—X where X=OH, F, $CF_3$ or $OCH_3$ and R=H, $CH_3$, $CH_2OH$ or $CH_2OCH_3$; locked nucleic acid monomers or derivatives thereof (LNA); peptide nucleic acid monomers or derivatives thereof (PNA);

b.) nucleotide analogs such as pseudo U, 7-halo-7-deaza purine, 7-propyne-7-deaza purine, 2,6-diamino purine, 5-propynyl, 5-methylthiazole, tricyclic carbazole-based pyrimidine analogs, tricyclic phenoxazine-based pyrimidine analogs, 2-thio T;

c.) nucleotide analogs having backbone modifications such as thioformacetal (—S—$CH_2$—O—$CH_2$—), methylene(methylimino), dimethylhydrazino, phosphoryl linked morpholino, —$CH_2$—CO—NH—$CH_2$—, —$CH_2$—NH—CO—$CH_2$—; and d.) a combination of any of the modifications cited in a), b), and c).

In some embodiments, further modified nucleobase portions that generally enhance hybridization affinity include, but are not limited to, 2,6-diaminopurine, hypoxanthine, pseudouridine, C-5-propyne, isocytosine, isoguanine, 2-thiopyrimidine, methylcytosine, 6-mercaptopurine, 5-fluorouracil, 5-iodo-2'-deoxyuridine, 6-thioguanine, and other like analogs. According to certain embodiments, nucleobase analogs are iso-C and iso-G nucleobase analogs available from Sulfonics, Inc., Alachua, Fla. (e.g., Benner, et al., U.S. Pat. No. 5,432,272).

In some embodiments, further modified pentose portions that generally enhance hybridization affinity include, but are not limited to, 2'- or 3'-modifications where the 2'- or 3'-position is hydrogen, hydroxy, alkoxy, e.g., methoxy, ethoxy, allyloxy, isopropoxy, butoxy, isobutoxy and phenoxy, azido, amino or alkylamino, fluoro, chloro, bromo and the like.

In some embodiments, modified internucleotide linkages that generally enhance hybridization affinity include, but are not limited to, phosphate analogs, analogs having achiral and uncharged intersubunit linkages (e.g., Sterchak, E. P., et al., *Organic Chem,* 52:4202 (1987)), and Uncharged morpholino-based polymers having achiral intersubunit linkages (e.g., U.S. Pat. No. 5,034,506). Internucleotide linkage analogs include, but are not limited to, morpholidate, acetal, and polyamide-linked heterocycles.

In some embodiments, modified phosphate portions can comprise analogs of phosphate wherein the phosphorous atom is in the +5 oxidation state and one or more of the oxygen atoms is replaced with a non-oxygen moiety, e.g., sulfur. Exemplary phosphate analogs include but are not limited to phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$, if such counterions are present.

Schematics for various embodiments of the ligation-enhanced target nucleic acid detection assay using chimeric oligonucleotide probes are provided by FIG. 1A-FIG. 1C, FIG. 2A-FIG. 2B, and FIG. 3-FIG. 5.

Target nucleic acid: A "target nucleic acid" or "target nucleic acid sequence" comprises a specific nucleic acid sequence that is to be detected and typically can be quantified. With reference to FIG. 1A-FIG. 1C, target nucleic acid 10 is a single-stranded RNA. With reference to FIG. 2A-FIG. 2B, target nucleic acid 8 is one strand of DNA. A person of ordinary skill in the art will appreciate that while the target nucleic acid sequence can be described as a single-stranded molecule, the complement thereof or a double-stranded target nucleic acid molecule can also serve as a target nucleic acid sequence.

In certain embodiments; the target nucleic acid can comprise single- or double-stranded DNA, DNA:RNA hybrids, or RNA, including, but not limited to, mRNA and its precursors, and non-coding. RNA (ncRNA) including, but not limited to, rRNA, tRNA, micro RNAs (miRNA), short interfering RNAs (siRNA), small temporal RNAs (stRNA) or short nuclear RNAs (snRNA). Target nucleic acid detected by some embodiments can be less than about 100 nucleotides in length, less than about 90 nucleotides in length, less than about 80 nucleotides in length, less than about 70 nucleotides in length, less than about 60 nucleotides in length, less than about 50 nucleotides in length, less than about 40 nucleotides in length, less than 30 nucleotides in length or even less than 20 nucleotides in length, can be degraded due to the sample source having been compromised, and can be of low abundance in a cell. Target nucleic acid detected by some embodiments can be partially double-stranded and partially single-stranded such as for a nucleic acid having a portion that forms a denatured "bubble" in which nucleotides are not base-paired. The "target" portion may be the double-stranded portion, the single-stranded portion, or the "target" portion may overlap the double-stranded and single-stranded portions.

The nucleic acid can be isolated from its normal milieu. That is, removal of any contaminant in any amount from the normal milieu of a nucleic acid accomplishes a degree of isolation of the nucleic acid. Methods for isolating nucleic acid are well known in the art. Procedures for isolation of small RNA molecules, such as microRNA and siRNA molecules are described in U.S. Published Patent Application No. 2005/0059024 to Conrad et al. filed Sep. 19, 2003. Procedures for RNA extraction from paraffin embedded tissue are described in U.S. Published Patent Application No. 2005/0059054 to Conrad et al. filed Jul. 26, 2004 using the RECOVERALL® kit from Ambion (Austin, Tex.), which kit was used herein for purifying RNA.

Sample: A sample can include at least one cell, cell culture, tissue specimen, lysate, extract, solution, or reaction mixture suspected of containing a target nucleic acid. In certain embodiments, a sample includes any collection of two or more cells that are isolated from a subject. A subject includes any organism from which a sample can be isolated. Non-limiting examples of organisms include eukaryotes such, as fungi, animals, or plants. The animal, for example, can be a mammal or a non mammal. The mammal can be, for example, a mouse, rat, rabbit, dog, pig, cow, horse, rodent, or a human. In some embodiments, the tissue sample is a human tissue sample. In certain embodiments, the tissue sample comprises blood, for example but not limited to, red blood cells, white blood cells, platelets, plasma, serum, or whole blood. The sample, in other non-limiting embodiments, comprises saliva, a cheek, throat, or nasal swab, a fine needle aspirate, a tissue print, cerebral spinal fluid, mucus, lymph, feces, urine, skin, plasma, serum, blood products, spinal fluid, peritoneal fluid, lymphatic fluid, aqueous or vitreous humor, synovial fluid, tears, semen, seminal fluid, vaginal fluids, pulmonary effusion, serosal fluid, organs, bronchio-alveolar lavage, tumors, and constituents and components of in vitro cell cultures. In certain embodiments, the tissue sample comprises a solid tissue sample. In certain embodiments, the sample comprises a virus, bacteria, or fungus. In certain embodiments, the sample comprises ex vivo tissue. In certain embodiments, a sample includes an enzymatic reaction mixture such as a PCR reaction mixture.

The sample can be compromised. The term "compromised," as used herein, refers to a sample having nucleic acids that are degraded. Compromised samples can result from exposure to physical forces, such as shear forces, to harsh environments such as heat or ultraviolet light, to chemical degradation processes such as may be employed in clinical or forensic analyses, to biological degradation processes due to microorganisms or age, to purification or isolation techniques, or a combination thereof. Degraded nucleic acids can have breaks, nicks, or chemical modifications when compared to a full-length normal form of that nucleic acid in its natural environment.

Standard preservation techniques for storage of biological tissue samples use formalin, formaldehyde or paraformaldehyde for fixation; paraffin, acrylamide or celloidin for embedding; and some embedding procedures use high temperatures such as for paraffin infiltration, for example. Such treatment can compromise a sample, including several types of chemical modifications of both DNA and RNA. Formalin-fixed and paraffin-embedded (FFPE) RNA or DNA samples typically contain nucleotide-to-nucleotide and nucleotide-to-protein cross-links, base modifications and other chemical modifications that affect the integrity of the nucleic acid. For example, the reaction between formaldehyde and nucleotides forms a methylene bridge between amino groups of two nucleotides. This modification has been shown to interrupt reverse transcription (Masuda et. al., Nucleic Acids Res. 27(22):4436-4443, 1999). Further, with time, FFPE nucleic acid samples typically degrade resulting in fragmentation, particularly of RNA. These modifications of DNA and RNA tend to inhibit the ability of traditional polymerases to replicate template sequences, thus resulting in inaccurate measurements and unreliable data.

The sample can be, for example, a preserved or archived sample such as a formalin-fixed sample, a paraffin-embedded sample, a FFPE sample, a forensic sample, a diagnostic sample such as blood or a biopsy sample, or an investigational sample such as, for example, a tissue or fluid sample from a plant or animal, or a sample from a culture of a microorganism such as a eukaryotic microorganism, for example a yeast. The sample can be a tissue slice present on a histology slide, for example. Any of these samples can be a compromised sample.

Preselected Sequence of a Target Nucleic Acid: A preselected sequence of a target nucleic acid is the specific nucleic acid sequence of the target that is to be detected. The preselected sequence is also referred to as the "target detection region" or target "footprint" of the target nucleic acid that ligation-enhanced nucleic acid detection assay embodiments are designed to detect. Target detection regions can be identified for each target nucleic acid sequence, using folding analysis similar to that disclosed in Zuker et al, "Algorithms and Thermodynamics for RNA Secondary Structure Prediction: A Practical Guide," in *RNA Biochemistry and Biotechnology*, pages 11-43, J. Barciszewski & B. F. C. Clark, eds., NATO ASI Series, Kluwer Academic Publishers (1999). To assist in selecting appropriate double-strand-specific quantitation reagent nucleotide sequences (i.e., TAQMAN® probe sequences), the potential targeting regions of each target nucleic acid sequence can be analyzed using PRIMER EXPRESS® software (Applied Biosystems, Foster City, Calif.). A melting temperature of a duplex formed between a double-strand-specific quantitation reagent nucleotide sequence and ligated chimeric oligonucleotide probes is, in some embodiments, about 68° C. to 70° C.

A Set of Chimeric Oligonucleotide Probes: A set of chimeric oligonucleotide probes, as used herein, includes at least one first chimeric oligonucleotide probe and at least one second oligonucleotide probe. In certain embodiments, the at least one second oligonucleotide probe is at least one second chimeric oligonucleotide-probe. According to various embodiments, at least one first chimeric oligonucleotide probe has at least two different types of nucleotide structures, that is, at least two selected from deoxyribonucleotides, nucleotide analogs, and ribonucleotides. In certain embodiments, at least one first chimeric oligonucleotide probe has two different portions with separate functions, the first function is that of amplification primer function and the second function is that of enhanced nucleotide-binding function.

In certain embodiments, a chimeric oligonucleotide probe comprises at least one deoxyribonucleotide and at least one nucleotide analog. First and second chimeric oligonucleotide probes are each designed to comprise a primer-specific portion and a target-specific portion. Each target-specific portion is complementary to different but contiguous preselected sequences of a target nucleic acid such that, under annealing conditions, the target-specific portion of each probe hybridizes in a sequence-specific manner with the complementary region of the target nucleic acid and, when hybridized, the first chimeric oligonucleotide probe is immediately adjacent to or "juxtaposed" to the second chimeric oligonucleotide probe in the duplexed nucleic acid as further discussed below. Chimeric oligonucleotide probes were synthesized using conventional automated nucleic acid synthesis chemistry. Probes were purified using HPLC technology known to one of ordinary skill in the art.

First Chimeric Oligonucleotide Probe: A first chimeric oligonucleotide probe is exemplified herein with reference to FIG. 1A-FIG. 1C, and FIG. 2A-FIG. 2B. The exemplary first chimeric oligonucleotide probe 101 comprises, in a 5' to 3' direction, a 5' primer-specific portion 1 comprising an amplification primer nucleotide sequence, and a target-specific portion 3.

Primer-Specific Portion of the First Chimeric Oligonucleotide Probe: The primer-specific portion 1 of exemplary first chimeric oligonucleotide probe 101 has complementarity to a primer oligonucleotide useful for priming the synthesis of a complementary nucleic acid using a polymerase, e.g., a reverse transcriptase or a DNA polymerase. Therefore, primers have 3'-enzymatically extendable ends and are useful for amplification reactions such as in PCR. Primer-specific portion 1 essentially lacks complementarity to the target nucleic acid. In certain embodiments, the primer-specific portion 1 comprises a universal primer site. In further embodiments, the primer-specific portion 1 comprises a universal reverse transcription primer site.

The first chimeric oligonucleotide probe 101 can further comprise a promoter sequence such as a T7 promoter sequence, or a reverse transcription primer sequence as part of the primer-specific portion of the probe. The first chimeric oligonucleotide probe 101 can further comprise a promoter sequence, such as a T7 promoter sequence, 5' to the primer-specific portion of the probe. A promoter sequence provides for binding of a polymerase such as T7 DNA polymerase to the ligated product. A reverse transcription primer sequence provides for binding of reverse transcriptase for transcription of the ligated product. Promoters are particularly useful, for example, for some embodiments of use in arrays.

Target-Specific Portion of the First Chimeric Oligonucleotide Probe: The target-specific portion 3 of exemplary first chimeric oligonucleotide probe 101 has complementarity to a 3'-portion of a preselected sequence Of a target nucleic acid 10, for example, as shown in FIG. 1A-FIG. 1C, and has a length of 6 nucleotides to 44 nucleotides. A 3'-portion of a preselected sequence of a nucleic acid comprises, for example, a region of a target nucleic acid 10 that is positioned 3' of a gap or nick that results from annealing, target nucleic acid 10 to the set of chimeric oligonucleotide probes.

In certain embodiments of the first chimeric oligonucleotide probe 101, the target-specific portion 3 comprises, in a 5' to 3' direction, a first portion 3a and a second portion 3b, wherein the first portion 3a comprises at least one nucleotide analog at one of the six 5'-most nucleotides wherein the nucleotide analog has enhanced affinity for base pairing as compared to a corresponding non-modified nucleotide. In certain embodiments of the target-specific portion, the 5'-most nucleotide of the first portion 3a comprises a nucleotide analog. In further embodiments, two, three, four, five or six of the six most 5'-nucleotides of the first portion 3a comprise a nucleotide analog. In certain embodiments, nucleotide analogs are contiguous. In certain embodiments, the nucleotide analogs are different from each other. In certain embodiments, second portion 3b comprises primarily non-modified ribonucleotides. In certain embodiments, all nucleotides of second portion 3b comprise modified ribonucleotides. "Primarily," as used herein, means greater than 50% of a value.

In some embodiments, the 3'-terminal nucleotide 7 and the 3'-penultimate nucleotide are independently a non-modified ribonucleotide or a nucleotide analog. In some embodiments, both the 3'-terminal nucleotide 7 and the 3'-penultimate nucleotide 5 comprise non-modified ribonucleotides or they both comprise nucleotide analogs. In some embodiments, the 3'-terminal nucleotide 7 of the target-specific portion 3 comprises a 3' hydroxyl group 9. In various embodiments, the 3'-terminal nucleotide 7 comprises a 2'-OR group wherein R comprises H or $C_1$-$C_3$ alkyl. In various embodiments, the 3'-penultimate nucleotide 5 comprises a 2'-OR group wherein R comprises H or $C_1$-$C_3$ alkyl.

The length of the target-specific portion of the first chimeric oligonucleotide probe can be from 6 nucleotides to 44 nucleotides, from 6 to 30 nucleotides, from 6 to 25 nucleotides, from 8 to 35 nucleotides, from 8 to 30 nucleotides, from 8 to 20 nucleotides, from 10 to 20 nucleotides, from 20 to 25 nucleotides, or from 10 to 15 nucleotides or any range therebetween. That is, the length of the target-specific portion can be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 nucleotides.

In various embodiments, first chimeric oligonucleotide probe comprises an addressable sequence 11 as shown in FIG. 1B and FIG. 2B. An addressable sequence can be an addressable support-specific sequence such as a hybridization pull-out sequence, or a capture sequence; or a binding portion of a detector probe sequence, such as a TAQMAN® sequence.

Second Chimeric Oligonucleotide Probe: A second chimeric oligonucleotide probe is exemplified with reference to FIG. 1A-FIG. 1C, and FIG. 2A-FIG. 2B. Exemplary second Chimeric oligonucleotide probe 102 comprises, in a 5' to 3' direction, a 5' target-specific portion 2 and a 3' primer-specific portion 4 comprising an amplification primer nucleotide sequence.

Target-Specific Portion of the Second Chimeric Oligonucleotide Probe: The target-specific portion 2 of second chimeric oligonucleotide probe 102 has complementarity to a 5' portion of a preselected sequence of the target nucleic acid 10, for example as shown in FIG. 1A-FIG. 1C, and has a length of 6 nucleotides to 44 nucleotides. A 5'-portion of a preselected sequence of a nucleic acid comprises, for example, a region of a target nucleic acid 10 that is positioned 5' of a gap or nick that results from annealing target nucleic acid 10 to the set of chimeric oligonucleotide probes.

The 5'-terminal nucleotide 6 of target-specific portion 2 of second chimeric oligonucleotide probe 102 comprises a 5' phosphate group and can be a non-modified ribonucleotide or a nucleotide analog. The 5'-terminal phosphate of the 5'-terminal nucleotide can be preadenylated as described, for example, in Yin et al., (*JBC* 278:20, 17601-17608, 2003).

In certain embodiments of exemplary second chimeric oligonucleotide probe 102, the target-specific portion 2 comprises, in, a 5' to 3' direction, a first portion 2*a* and a second portion 2*b*, wherein the second portion 2*b* comprises at least one nucleotide analog, at one of the six 3'-most nucleotides wherein the nucleotide analog has enhanced affinity for base pairing as compared to a corresponding non-modified nucleotide. In certain embodiments of the target-specific portion, the 3'-most nucleotide of the second portion 2*b* is a nucleotide analog. In further embodiments, two, three, four, five or six of the six 3'-most nucleotides of the second portion 2*b* comprise nucleotide analogs. In some embodiments, nucleotide analogs are contiguous. In certain embodiments, the nucleotide analogs are different from each other and/or from those of the first chimeric oligonucleotide probe. In certain embodiments, first portion 2*a* comprises primarily non-modified ribonucleotides.

The length of the target-specific portion of the second chimeric oligonucleotide probe can be from 6 nucleotides to 44 nucleotides, from 6 to 30 nucleotides, from 6 to 25 nucleotides, from 8 to 35 nucleotides, from 8 to 30 nucleotides, from 8 to 20 nucleotides, from 10 to 20 nucleotides, from 20 to 25 nucleotides, or from 10 to 15 nucleotides or any range therebetween. The length of the target-specific portion of the first chimeric oligonucleotide probe together with the length of the target-specific portion of the second chimeric oligonucleotide probe can be from 12 to 88 nucleotides, from 12 to 80 nucleotides, from 12 to 70 nucleotides, from 12 to 60 nucleotides, from 12 to 50 nucleotides, from 12 to 40 nucleotides, from 15 to 30 nucleotides, from 18 to 25 nucleotides, or from 12 to 25 nucleotides, or any range therebetween. In certain embodiments, the length of the target-specific portion of the first chimeric oligonucleotide probe taken together with the length of the target-specific portion of the second chimeric oligonucleotide probe can be from 12-45 nucleotides, or from 12-55 nucleotides, or from 12-65 nucleotides, or from 12-75 nucleotides, or from 12-85 nucleotides, or any range therebetween.

Primer-Specific Portion of the Second Chimeric Oligonucleotide Probe: The primer-specific portion 4 of exemplary second chimeric oligonucleotide probe 102 has complementarity to a primer oligonucleotide useful for printing the synthesis of a complementary nucleic acid using a polymerase, e.g., a reverse transcriptase or a DNA polymerase. Therefore, primers have 3'-enzymatically extendable ends and are useful for amplification reactions such as in PCR. Primer-specific portion 4 essentially lacks complementarity to the target nucleic acid. In certain embodiments, the primer-specific portion 4 comprises a universal primer site. In further embodiments, the primer-specific portion 4 comprises a universal forward primer site.

In certain embodiments, exemplary second chimeric oligonucleotide probe 102 further comprises a promoter sequence 14, such as a T7 promoter, or a universal reverse transcriptase site, 3' to the primer-specific portion as shown in FIG. 1B and FIG. 2B. The promoter sequence provides for binding of a polymerase such as T7 RNA polymerase for transcription of the ligated product.

In certain embodiments, portions of the first chimeric oligonucleotide probe can overlap another portion. Similarly, portions of the second chimeric oligonucleotide probe can overlap another portion. For example, but without limitation, a target-specific portion can overlap a primer-specific portion, a promoter sequence, or both. A primer-specific portion can comprise a promoter sequence. Also, without limitation, an addressable sequence can overlap with a target-specific portion or a primer-specific portion, or both.

Annealed Product: When annealed to target nucleic acid 10 as shown by reference no. 103 of FIG. 1A-FIG. 1C and to target nucleic acid 8 as shown by reference no. 103 of FIG. 2A-FIG. 2B, the 3'-OH group of the first chimeric oligonucleotide probe 101 is positioned immediately adjacent to the 5'-phosphate group of the second chimeric oligonucleotide probe 102 to form a nick 104. "Immediately adjacent to," as used herein, means that the 3' hydroxyl group of a first chimeric oligonucleotide probe is, juxtaposed to the 5'-phosphate group of a second chimeric oligonucleotide probe when both probes are hybridized to target nucleic acid having sequence complementarity to the nucleotide sequence of the probes. Such a nick is ligatable by ligases as described herein. For those target nucleic acids that have shorter lengths, such as some non-coding RNA including, but not limited to, miRNAS, siRNAs, stRNAs or snRNAs, the target nucleic acid can be fully hybridized throughout its length to the target-specific portion of the first probe taken together with the target-specific portion of the second probe.

FIG. 1C shows one embodiment of an annealed product wherein the 3' end of the first chimeric oligonucleotide probe and the 5' end of the second chimeric oligonucleotide probe are not immediately adjacent thereby providing a gap. The 3'-end of the first chimeric oligonucleotide probe can be extended with a polymerase to incorporate one or more nucleotides until the gap is filled and the ends are immediately adjacent.

Ligation: Ligation of annealed product 103 can comprise enzymatic ligation, autoligation, photoligation, or chemical ligation. Enzymatic ligation refers to use of a polypeptide having ligase activity where an inter-nucleotide linkage is formed between immediately adjacent ends of probes that are adjacently hybridized to a template. Formation of the linkage is double-strand dependent, also termed duplex-dependent or template-dependent. The internucleotide linkage can include, but is not limited to, phosphodiester bond formation. A ligase can include a double-strand dependent enzyme such as a DNA ligase or an RNA ligase, such as, for example, T4 DNA ligase, T4 RNA ligase, *Thermus thermophihis* (Tth) ligase, *Thermus aquaticus* (Taq) DNA ligase, *Thermus scotoductus* (Tsc) ligase, TS2126 RNA ligase, *Archaeoglobus flugidus* (Afu) ligase, *Pyrococcus furiosus* (Pfu) ligase, *Deinococcus radiodurans* RNA ligase (DraRnl) (Raymond et al., *Nucl Acids Res* 35(3):839-849, 2007), and DraRnl-type ligases include ligases such as GenBank accession no. XP_367846 from the fungi *Magnaporthe grisea*, GenBank accession no. CAE76396 from *Neurospora crassa*, accession no. XP_380758 from *Gibberella zeae*, and accession no. EAL61744 from the amoeba *Dictyostelium discoideum*.

In some embodiments, a ligase can be a reversibly inactivatable ligase such as disclosed in U.S. Pat. No. 5,773,258, or a heat-activatable ligase such as Afu ligase, T4 ligases, *E. coli* ligases, AK16D ligase, Pfu ligase, as well as enzymatically active mutants and variants thereof.

Embodiments include as ligases the bacteriophage T4 RNA ligase 1 (T4 Rnl1) and T4 RNA ligase 2 (T4 Rnl2) that represent different branches of the RNA ligase family. The T4 Rnl2 family include's vibriophage KVP40 Rnl2, the RNAediting ligases of *Trypanosoma brucei* (TbREL1 and TbREL2) and of *Leishmania tarentolae* (LtREL1 and LtREL2), among others. T4 Rnl2 ligase is commercially available from NEW ENGLAND BIOLABS® (Ipswidh, Mass.) or it can be isolated as described in Nandakumar et al., *JBC* 280(25):23484-23489, 2005; Nandakumar et al., *JBC* 279(30):1337-31347, 2004; and Nandakumar et al., *Molecular Cell* 16:211-221, 2004. The T4 Rnl2 enzyme is encoded by gene gp24.1 of phage T4. In certain embodiments, the ligase comprises T4 Rnl2.

In certain embodiments, the ligase can be preadenylated, or the 5'-terminal nucleotide of at least one second chimeric oligonucleotide probe can be preadenylated. Ho et al. (*Structure* 12:327-339) sets forth a mechanism for T4 Rnl2 where the C-terminal domain thereof functions in sealing 3'-OH and 5'-P RNA ends. The N-terminal segment (1-249) of the Rml2 protein is reported to function as an autonomous adenylyltransferase/App-RNA ligase domain. In general, RNA ligases join 3'-OH and 5'-$PO_4$ RNA termini through a series of three nucleotidyl transfer steps involving activated covalent intermediates. RNA ligase reacts with ATP to form a covalent ligase-AMP intermediate plus pyrophosphate. AMP is then transferred from ligase-adenylate to a 5'-$PO_4$ RNA end to form an RNA-adenylate intermediate (AppRNA). Ligase then catalyzes attack by an RNA 3'-OH on the RNA-adenylate to seal the two ends via a phosphodiester bond and release AMP. Mechanisms for RNA ligation are further discussed by Nandakumar et al. (ibid 2005, 2004a, 2004b) Yin et al. (*JBC* 278:20, 17601-17608; *Virology* 319:141-151, 2004), Ho et al. (ibid; *PNAS*, 99:20, 12709-12714, 2002), Gumport et al. (in *Gene Amplification and Analysis*, Vol 2, edited by Chirikjian, J. G., and Papas, T. S., 1981, 313-345) and by Raymond et al. (*Nucleic Acids Res.* 35:3, 839-849, 2007). Preadenylated agents such as ligase-adenylate and RNA-adenylate are contemplated for use in some embodiments of ligation enhanced nucleic acid detection.

Suitable conditions for carrying out the duplex-dependent ligase reaction are found in the references cited above in addition to the examples provided. Table 1 and Table 2 of Example 2 provide exemplary reagents for carrying out ligation-enhanced nucleic acid detection assay embodiments. Assay embodiments can be readily carried out using variations of the types and amounts of exemplary reagents known to be equivalent in function by one of ordinary skill in the art. For example, but not limited to, the *E. coli* RNA in the Hybridization Mix (Table 2) functions as a carrier RNA and other macromolecules carrying out the same function can be used; the Hybridization Mix can be incubated for less than 2 hr such as about 15 minutes or greater than 2 hr such as overnight; RNA dilution buffer can be warmed for serial dilution to a temperature from about 37° C. to about 75° C.; while the concentrations of total RNA sample used are 20 ng/μl, 2 ng/μl, 0.2 ng/μl and 0.02 ng/μl, the ranges of concentration can be from about 2000 ng/μl to 0.0002 ng/μl; the range of concentration of T4 Rnl2 ligase can be from about 0.001 pmol to about 100 pmol; the range of volumes of RNase Cocktail can be from about 0.01 μl to 10 μl; the 42° C. incubation of the qRT-PCR mix is optional; or combinations thereof. In certain embodiments, a cocktail containing a splint-dependent or duplex-dependent ligase, for example, T4 Rnl2, and a single-strand specific ribonuclease is added to the reaction containing the annealed product for about 30 minutes resulting in the ligation of the two probes at the nicked duplex, and inactivation of any nonannealed probes in the reaction. In some embodiments of the disclosed methods, a proteinase K digestion is then carried out to degrade protein.

In certain embodiments, non-enzymatic ligation is carried out by using a 3'-terminal first reactive group on the first chimeric oligonucleotide probe and a 5'-terminal second reactive group on the second chimeric oligonucleotide probe such that, when the first and second chimeric oligonucleotide probes are annealed to the target nucleic acid, the 3'-terminal nucleotide having the first reactive group of the first chimeric oligonucleotide probe is positioned immediately adjacent to the 5'-terminal nucleotide having the second reactive group, and the first and second reactive groups are in proximity and comprise autoligatable, chemically ligatable or photoligatable groups and, when ligated, form a 3'-5' covalent bond. In certain configurations, activating or reducing agents can be used. Examples of activating and reducing agents can include, without limitation, carbodiimide, cyanogen bromide (BrCN), imidazole, 1-methylimidazole/carbodiimide/cystamine, N-cyanoimidazole, dithiothreitol (DTT) and ultraviolet light, such as used for photoligation using routine methods known to skilled artisans. In various embodiments, chemical ligating can be accomplished as disclosed in U.S. Pat. No. 5,476,930 or U.S. Pat. No. 5,681,943. First and second autoligatable reactive groups can comprise, for example, an ester+hydrazide pair, a derivatized sulfide anion+haloalkyl pair, or a derivatized sulfide anion+α-haloacyl pair.

Ligated Product: As shown in FIG. 1A-FIG. 1C and in FIG. 2A-FIG. 2B, exemplary target-specific portions 3 and 2, when ligated, form a ligated product 106. Ligation of chimeric oligonucleotide probes hybridized to a target nucleic acid can vary in efficiency depending on the sequences selected for the target nucleic acid, and for the chimeric oligonucleotide probes. The sequences of chimeric oligonucleotide probes that ligate most efficiently can be determined empirically. Differences in efficiency of ligation can affect amounts of amplification product detected. However, in quantitative measurements of a target nucleic acid, control samples comprising known amounts of a nucleic acid can be used to produce standard curves to account for ligation efficiencies.

According to certain embodiments, forming ligated product comprises ligation techniques such as gap-filling ligation, including, without limitation, gap-filling OLA and LCR, bridging oligonucleotide ligation, FEN-LCR, and correction ligation. Descriptions of these techniques can be found, among other places, in U.S. Pat. No. 5,185,243, published European Patent Applications EP 320308 and EP 439182, published PCT Patent Application WO 90/01069, published PCT Patent Application WO 02/02823, and U.S. Pat. No. 6,511,810. Forming a ligated product can also comprise at least one gap-filling procedure such as set forth by FIG. 1C, wherein, when annealed to the target nucleic acid, the 3' end of the first chimeric oligonucleotide probe and the 5' end of the second chimeric oligonucleotide probe are not immediately adjacent thereby providing a gap. The 3'-end of the first chimeric oligonucleotide probe can be extended with a polymerase to incorporate one or more nucleotides until the gap is filled and the ends become immediately adjacent. Such a filling-in reaction using a polymerase is described, e.g. by U.S. Pat. No. 6,004,826.

A set of chimeric oligonucleotide probes for gap-filling embodiments is exemplified by FIG. 1C and comprises at least one first chimeric oligonucleotide probe 101, and at least one second chimeric oligonucleotide probe 102 wherein, when the at least one first and the at least one second chimeric oligonucleotide probes are annealed to the target nucleic acid 10, a gap 129 of one or more nucleotides separates the 3' hydroxyl group of the at least one first chimeric oligonucleotide probe and the 5' phosphate group of the at least one second chimeric oligonucleotide probe.

Certain methods for detecting a target nucleic acid in a sample using the set of chimeric oligonucleotide probes for gap-filling embodiments comprise, contacting the sample with the at least one set of chimeric oligonucleotide probes for each target nucleic acid to be detected for a time and under conditions suitable to form an annealed product; contacting the annealed product with a polymerase in the presence of nucleotides for a time and under conditions suitable to fill the gap; contacting the polymerized product with a polypeptide having double-strand dependent ligase activity for a time and under conditions suitable to form a ligated product; and detecting the target nucleic acid by detecting the ligated product, or surrogate thereof. In some embodiments, the target nucleic acid comprises RNA and the polymerase comprises reverse transcriptase. In further embodiments, the target nucleic acid comprises DNA and the polymerase comprises a DNA polymerase such as Klenow. One of skill in the art understands that rNTP's or dNTP's can be incorporated either by reverse transcriptase or Klenow, however efficiency will vary. Similarly, RNA ligase or DNA ligase can be used for any ligation embodiment, however, efficiency will vary.

In various embodiments, a plurality of oligonucleotide probes can be used for detection of a target nucleic acid in a sample, for example, a set of at least three oligonucleotide probes such as set forth by FIG. 3. Such a three-probe set comprises, in a 5' to 3' direction, at least one first or 5'-most chimeric oligonucleotide probe 301, a medial probe 300, and at least one second or 3'-most chimeric oligonucleotide probe 302. A 5'-most chimeric oligonucleotide probe 301 has complementarity to a 3' portion of a preselected sequence of the target nucleic acid and comprises, in a 5' to 3' direction, a 5' primer-specific portion 1 comprising an amplification primer nucleotide sequence, a first target-specific portion 3a comprising at least one nucleotide analog at one of the six 5'-most nucleotides wherein the nucleotide analog has enhanced affinity for base pairing as compared to a corresponding non-modified nucleotide, and 3'-OH and 2'-OR groups on 3'-terminal nucleotide 91, wherein R comprises H or $C_1$-$C_3$ alkyl.

As depicted in FIG. 3, medial probe 300 has complementarity to a portion of the preselected sequence of the target nucleic acid intermediate the first 301 and second 302 chimeric oligonucleotide probes, a length of 6 nucleotides to 44 nucleotides, a 5'-phosphate at 5'-terminal nucleotide 61, primarily non-modified ribonucleotides wherein any nucleotide analog, therein has enhanced affinity for base pairing as compared to a corresponding non-modified nucleotide, and 3'-OH and 2'-OR groups on the 3'-terminal nucleotide 92, wherein R comprises H or $C_1$-$C_3$ alkyl.

The most 3' probe of a three-probe set as depicted in FIG. 3 is referred to as at least one second or a 3'-most chimeric oligonucleotide probe 302. Second oligonucleotide probe 302 has complementarity to a 5' portion of the preselected sequence of the target nucleic acid and comprises, in a 5' to 3' direction, a 5'-phosphate at the 5'-terminal nucleotide 62 of target-specific portion 2b where target-specific portion 2b comprises at least one nucleotide analog at one of the six 3'-most nucleotides wherein the nucleotide analog has enhanced affinity for base pairing as compared to a corresponding non-modified nucleotide, and a 3' primer specific portion 4 comprising an amplification primer nucleotide sequence. When the first chimeric, medial and second chimeric oligonucleotide probes are annealed to the target nucleic acid 10, as shown at 303 of FIG. 3, the 3' hydroxyl group of the first chimeric oligonucleotide probe 301 is positioned immediately adjacent to the 5' phosphate group of the medial probe 300, and the 3' hydroxyl group of the medial probe 300, is positioned immediately adjacent to the 5' phosphate group of the second oligonucleotide probe 302. In certain embodiments, the 3' hydroxyl group of the first chimeric oligonucleotide probe is not immediately adjacent to the 5' phosphate group of the medial probe, or the 3' hydroxyl group of the medial probe is not immediately adjacent to the 5' phosphate group of the second oligonucleotide probe. For such embodiments, the probes are rendered immediately adjacent by gap-filling.

According to some embodiments, certain methods for detecting a target nucleic acid 10 in a sample using a set of three oligonucleotide probes, and depicted in FIG. 3, comprise contacting the sample with the set of at least three chimeric oligonucleotide probes for a time and under conditions suitable to form an annealed product 303; contacting annealed product 303 with a polypeptide having double-strand dependent ligase activity for a time and under conditions suitable to form a ligated product 305; and detecting the target nucleic acid in the sample by detecting the ligated product, or a surrogate thereof.

Various embodiments include a single chimeric oligonucleotide probe 400 that forms a nicked circular duplex when annealed to the target nucleic acid such as that shown at 403 in FIG. 4. Such a single chimeric oligonucleotide probe comprises, in a 5' to 3' direction, (1) a target-specific portion 2 having: a 5'-terminal nucleotide comprising a 5'-phosphate group, complementarity to a 5' portion of the preselected sequence of a target nucleic acid 10, at least one nucleotide analog at one of the six 3'-most nucleotides wherein the nucleotide analog has enhanced affinity for base pairing as compared to a corresponding non-modified nucleotide, and a length of 6 nucleotides to 44 nucleotides; (2) a reverse primer-specific portion 4 comprising an amplification primer nucleotide sequence; (3) a forward primer-specific portion 1 comprising an amplification primer nucleotide sequence; and (4) a target-specific portion 3 having: complementarity to a 3' portion of a preselected sequence of the target nucleic acid 10, a length of 6 nucleotides to 44 nucleotides, at least one nucleotide analog at one of the six 5'-most nucleotides wherein the nucleotide analog has enhanced affinity for base pairing as compared to a corresponding non-modified nucleotide, and 3'-OH and 2'-OR groups on the 3'-terminal nucleotide, wherein R comprises H or $C_1$-$C_3$ alkyl. For such embodiments, when the chimeric oligonucleotide probe is annealed to the target nucleic acid as at 403 of FIG. 4, the 3' hydroxyl group of target-specific portion 3 is positioned immediately adjacent to the 5' phosphate group of target-specific portion 2, thereby forming an annealed circular duplex having nick 404.

In some embodiments, a method for detecting a target nucleic acid in a sample comprises (a) contacting the sample with at least one single chimeric oligonucleotide probe 400 for a time and under conditions suitable to form an annealed product 403; (b) contacting the annealed product with a polypeptide having double-strand dependent ligase activity for a time and under conditions suitable to form a ligated product 405; and (c) detecting the target nucleic acid in the sample by detecting the ligated product.

Embodiments of chimeric oligonucleotide probes for non-enzymatic duplexed-enhanced ligation include a probe set comprising (1) at least one first chimeric oligonucleotide probe, comprising, in a 5' to 3' direction: a primer-specific portion comprising an amplification primer nucleotide sequence; and a target-specific portion, the target-specific portion having: complementarity to a 3' portion of a preselected sequence of a target nucleic acid, a length of 6 nucleotides to 44 nucleotides, at least one nucleotide analog at one of the six 5'-most nucleotides wherein the nucleotide analog has enhanced affinity for base pairing as compared to a corresponding non-modified nucleotide, and a 3'-terminal first reactive group; and (2) at least one second chimeric oligonucleotide probe comprising, in a 5' to 3' direction: a target-specific portion having: a 5'-terminal second reactive group, at least one nucleotide analog at one of the six 3'-most nucleotides wherein the nucleotide analog has enhanced affinity for base pairing as compared to a corresponding non-modified nucleotide, complementarity to a 5' portion of the preselected sequence of the target nucleic acid, a length of 6 nucleotides to 44 nucleotides, and a primer-specific portion comprising an amplification primer nucleotide sequence; wherein, when the first and second chimeric oligonucleotide probes are annealed to the target nucleic acid, the 3'-terminal nucleotide having the first reactive group of the first chimeric oligonucleotide probe is positioned immediately adjacent to the 5'-terminal nucleotide having the second reactive group, and the first and second reactive groups are in proximity. For such embodiments, the first and second reactive groups comprise autoligatable, chemically ligatable or photoligatable groups and, when ligated, form a 3'-5' covalent bond.

For such non-enzymatically ligatable probes, the first and second reactive groups comprise autoligatable groups and the autoligatable groups comprise an ester+hydrazide pair, a derivatized sulfide anion+haloalkyl pair, or a derivatized sulfide anion+α-haloacyl pair; chemically ligatable groups; or photoligatable groups.

A method for detecting a target nucleic acid in a sample using non-enzymatic ligation of chimeric oligonucleotide probes, comprises contacting the sample with the set of chimeric oligonucleotide probes for a time and under conditions suitable to form an annealed product; contacting the annealed product for a time and under conditions suitable to allow ligation of the 3'-terminal nucleotide and the 5'-terminal nucleotide to form a ligated product; and detecting the target nucleic acid in the sample by detecting the ligated product.

RNase treatment: Addition of a single-strand specific ribonuclease to the ligation mix as described in Table 2 of Example 2 results in degradation of the RNA portions of the probes, effectively inactivating those probes that are not annealed to target nucleic acid, and degradation of non-annealed template portions in an embodiment where the target nucleic acid comprises RNA. Non-annealed probes are thereby rendered ineffective for ligation. For studies presented herein, the RNASE COCKTAILTK™ (Ambion Inc., Austin Tex. #2286) was used that includes RNase A and RNase T1. Further RNases that can be used include RNase 1, RNase T2, RNase U2, or RNase PhyM. While the embodiment of Table 2 provide for use of 1 µl of cocktail (10 U of RNase T1 and 0.25 U of RNase A), results from further studies demonstrate that decreasing the amount of RNase can improve the performance of chimeric oligonucleotide probes that comprise nucleotide analogs. For example, decreasing the amount of RNase by a factor of 25 allowed a greater detection level of target nucleic acid using chimeric oligonucleotide probes having four nucleotide analogs in the target-specific portions proximal to the primer-specific portions.

In certain embodiments, a ligated product is purified. Purification processes include, but are not limited to, molecular weight or size exclusion processes, e.g., gel filtration Chromatography or dialysis, sequence-specific hybridization-based pullout methods, affinity capture techniques, precipitation, adsorption, or other nucleic acid purification techniques. Purification can reduce the quantity of primers needed to amplify the ligation product, thus reducing the cost of detecting a target sequence as well as decreasing possible side reactions during amplification. In certain embodiments, ligase and RNase can be removed by treatment with a protease such as proteinase K, elastase, calpain, chymotrypsin, papain, ficin, subtilisin, plasmin, trypsin, or a combination thereof, for example.

Detecting Ligated Product: Embodiments of detecting a ligated product include detection means such as amplification using the polymerase chain reaction and variations thereof, or using a mobility-dependent analysis technique such as electrophoresis including capillary electrophoresis, chromatography, mass spectroscopy, sedimentation analysis including gradient centrifugation, field-flow fractionation, multi-stage extraction techniques, or the like. A mobility inodifier can be a nucleobase polymer sequence which can increase the size of a detector probe, or in some configurations, a mobility modifier can be a non-nucleobase moiety which increases the frictional coefficient of a probe. A detector probe comprising a mobility modifier can exhibit a relative mobility in an electrophoretic or chromatographic separation medium that allows a user to identify and distinguish the detector probe from other molecules of a sample. For illustrative teachings in capillary electrophoresis, detection and mobility probes, see for example U.S. Pat. No. 5,777,096, 6,624,800, 5,470,705, 5,514,543, or 6,395,486.

Amplification: As used herein, "amplification" or "amplify" and the like refers to a process that results in an increase, in the copy number of a molecule or set of related molecules. As the term applies to ligated products, amplification means the production of multiple copies of the ligated products, or a portion of the ligated products. Amplification can encompass a variety of chemical and enzymatic processes including without limitation, a polymerase chain reaction (PCR), a strand displacement amplification reaction, a transcription mediated amplification reaction, a nucleic acid sequence-based amplification reaction, a rolling circle amplification reaction, or a ligase chain reaction. According to certain embodiments, following at least one amplification cycle, the amplification products can be separated based on their molecular weight or length or mobility by, for example, without limitation, gel electrophoresis, HPLC, MALDI-TOF, gel filtration, or mass spectroscopy. The detection and quantitation of a labeled sequence at a particular mobility address indicates that the sample or starting material contains the corresponding target nucleic acid sequence at the determined concentration.

Polymerase Chain Reaction: The PCR includes introducing a molar excess of two or more extendable oligonucleotide primers to a reaction mixture comprising the ligated product, where the primers hybridize to opposite strands of the ligated product. The reaction mixture is subjected to a program of thermal cycling in the presence of a DNA polymerase, resulting in the amplification of the target specific portions of the ligated product flanked by the primers. Reverse transcriptase PCR is a PCR reaction that uses an RNA template and a reverse transcriptase, or a polypeptide having reverse transcriptase activity, to first generate a single stranded DNA molecule prior to the multiple cycles of DNA-dependent DNA polymerase primer elongation. Methods for a wide variety of PCR applications are widely known in the art, and described in many sources, for example, Ausubel et al. (eds.), Current Protocols in Molecular Biology, Section 15, John Wiley & Sons, Inc., New York (1994).

Criteria for designing sequence-specific primers are well known to persons of ordinary skill in the art. Detailed descriptions of primer design that provide for sequence-specific annealing can be found, among other places, in Diffenbach and Dveksler, PCR Primer, A Laboratory Manual, Cold Spring Harbor Press, 1995, and Kwok et al. (*Nucl. Acid Res.* 18:999-1005, 1990). The sequence-specific portions of the primers are of sufficient length to permit specific annealing to complementary sequences, as appropriate. A primer does not need to have 100% complementarity with a primer-specific portion for primer extension to occur. Further, a primer can be detectably labeled such that the label is detected by, for example, biochemical, chemical, immunochemical, spectroscopic, photochemical, or other detection means. A primer pair is sometimes said to consist of a "forward primer" and a "reverse primer," indicating that they are initiating nucleic acid polymerization in opposing directions from different strands of the ligated product. The set of chimeric oligonucleotide probes, in some embodiments, comprises at least one deoxyribonucleotide in the primer-specific portion of the first or the second chimeric oligonucleotide probe and in further embodiments, the primer-specific portions of the first, the second, or both chimeric oligonucleotide probes comprises primarily deoxyribonucleotides.

In some embodiments, a primer-specific portion of chimeric oligonucleotide probes can comprise a universal priming site. The term "universal primer" refers to a primer comprising a universal site that is able to hybridize to all, or essentially all, potential priming sites in a multiplexed reaction. The term "semi-universal primer" refers to a primer that is capable of hybridizing with more than one (e.g., a subset), but not all, of the potential sites to be amplified in a multiplexed reaction. The terms "universal site," "universal priming site," or "universal primer site" or the like refer to a site contained in a plurality of primers, where the universal priming site that is found in a ligated product to be amplified is complementary to a universal primer.

In certain embodiments, single-stranded amplification products can be generated by methods including, without limitation, asymmetric PCR, assymetric reamplification, nuclease digestion, and chemical denaturation. For example, single-stranded sequences can be generated by combining at least one first primer or at least one second primer from a primer set, but not both, in an amplification reaction mixture.

Polymerase: The term "polymerase," as used herein, refers to a polypeptide that is able to catalyze the addition of nucleotides or analogs thereof to a nucleic acid in a template dependent manner, for example, the addition of deoxyribonucleotides to the 3'-end of a primer that is annealed to a nucleic acid template during a primer extension reaction. Nucleic acid polymerases can be thermostable or thermally degradable. Suitable thermostable polymerases include, but are not limited to, polymerases isolated from *Therms aquaticus, Thermus thermophiles, Pyrococcus woesei, Pyrococcus furiosus, Thermococcus litoralis*, and *Thermotoga maritima*. Therefore, in some embodiments, "cycle sequencing" can be performed. Suitable thermodegradable polymersases include, but are not limited to, *E. coli* DNA polymerase I, the Klenow fragment of *E. coli* DNA polymerase I, T4 DNA polymerase, T5 DNA polymerase, T7 DNA polymerase, and others. Examples of other polymerizing enzymes that can be used in the methods described herein include but are not limited to T7, T3, SP6 RNA polymerases and AMV, M-MLV and HIV reverse transcriptases.

Commercially available polymerases include, but are not limited to AMBION'S SUPERTAQ® polymerase and SUPERTAQ® Plus polymerase, TAQFS® polymerase, AMPLITAQ® CS polymerase (Perkin-Elmer), AMPLITAQ® FS polymerase (Perkin-Elmer), KENTAQ1® polymerase (AB Peptide, St. Louis, Mo.), TAQUENASE® polymerase (Scien Tech Corp., St. Louis, Mo.), THERMOSEQUENASE® polymerase (Amersham), Bst polymerase, READER™ Taq DNA polymerase, VENT® DNA polymerase, $VENT_R$® DNA Polymerase, $VENT_R$® (exo⁻) polymerase and DEEPVENT® DNA polymerase, (all VENT® polymerases can be obtained from New England Biolabs), PFUTurbo™ DNA polymerase (Stratagene), Pwo polymerase, Tth DNA polymerase, KlenTaq-1 polymerase, SEQUENASE™ 1.0 DNA polymerase (Amersham Biosciences), SEQUENASE™ 2.0 DNA polymerase (United States Biochemicals), and an enzymatically active mutant and variant thereof.

Descriptions of DNA polymerases can be found in, among other places, Lehninger *Principles of Biochemistry*, 3d ed., Nelson and Cox, Worth Publishing, New York, N.Y., 2000, particularly Chapters 26 and 29; Twyman, *Advanced Molecular Biology: A Concise Reference*, Bios Scientific Publishers, New York, N.Y., 1999; Ausubel et al., *Current Protocols in Molecular Biology*, John Wiley & Sons, Inc., including supplements through May 2005 (hereinafter "Ausubel et al."); Lin and Jaysena, *J. Mol. Biol.* 271:100-11, 1997; Pavlov et al., *Trends in Biotechnol.* 22:253-60, 2004; and *Enzymatic Resource Guide: Polymerases*, 1998, Promega, Madison, Wis.

In various detection embodiments, amplification is optionally followed by additional methods, for example, but not limited to, labeling, sequencing, purification, isolation, hybridization, size resolution, expression, detecting and/or cloning.

Detection of ligated product can be carried out by detection of an amplification product thereof. For example, the ligated product can comprise identifying portions or addressable portions, and following amplification, such identifying portions or addressable portions are detected. An addressable sequence portion can include a detector probe sequence or a hybridization capture sequence. The ligated product or an amplification product thereof can be purified by annealing the ligated product with a hybridization capture probe having complementarity to a hybridization capture sequence, for example. In yet further embodiments, the hybridization capture sequence comprises a mobility modifier sequence, and detecting a target nucleic acid comprises subjecting the ligated product or an amplification product thereof to at least one mobility-dependent analysis technique (MDAT) such as electrophoresis, chromatography, HPLC, mass spectroscopy, sedimentation, field-flow fractionation, or multi-stage fractionation.

Detection of an amplification product can comprise, for example, gel electrophoresis. Gel electrophoresis can use any separation medium, such as an agarose gel or a polyacrylamide gel. Detection can also utilize capillary gel electrophoresis. In certain aspects, one or both PCR primers can comprise a label, such as, for example, biotin, a fluorophore or a radioisotope. A label can facilitate detection of an amplification product comprising a labeled PCR primer. In various detection embodiments, following the PCR, a biotinylated strand can be captured and separated, and mobility modifiers can be hybridized to the immobilized strands. Eluted mobility modifiers are then detected via capillary electrophoresis.

Multiplex Assays: The term "multiplex assays" refers to PCR reactions that use more than two primers in a single reaction and at the same dine so that more than one different amplified product is produced and detected. For example, at least two pair of amplification primers are contacted at the same time and/or in the same solution with ligated product. Several ligated products can be detected simultaneously using multiplex assays. In addition, multiplexed ligation reactions where at least 2 target nucleic acids are queried with corresponding sets of first and second chimeric oligonucleotide probes are used in certain embodiments. In further embodiments, multiplexed ligation reactions contain a detector probe specific for each oligonucleotide probe set.

Real-tune PCR: As used herein, "real-time PCR" refers to the detection and quantitation of at least a segment of a ligated product while the reaction is ongoing. The amplified segment or "amplicon" can be detected in real time using a 5'-nuclease assay, particularly the TAQMAN® assay as described by e.g., Holland et al. (*Proc. Natl. Acad. Sci. USA* 88:7276-7280, 1991); and Heid et al. (*Genome Research* 6:986-994, 1996). For use herein, a detector probe sequence to which a TAQMAN® probe binds, for example, can be designed into the primer portion, into the target-specific portion, designed to span the junction of such portions, or designed as an additional segment as shown as reference number 11 of FIG. 1B or FIG. 2B. The detector probe 31 is typically labeled with a fluorescent reporter dye F and a quencher moiety Q in close proximity to each other to allow quenching of signal. Emission from the reporter dye is quenched by the quenching moiety when the fluor and quencher are in Close proximity, such as on the probe. In some embodiments, the probe can be labeled with only a fluorescent reporter dye or another detectable moiety.

"$T_m$," as used herein, refers to the melting temperature (temperature at which 50% of the oligonucleotide is a duplex) of the oligonucleotide determined experimentally or calculated using the nearest-neighbor thermodynamic values of Breslauer et al. (*Proc. Natl. Acad. Sci. USA* 83:3746 3750, 1986) for DNA or Freier et al. (*Proc. Natl. Acad. Sci. USA* 83:9373-9377, 1986) for RNA. In general, the $T_m$ of the TAQMAN® probe is about 10 degrees above the $T_m$ of amplification primer pairs. Amplification primer sequences and double dye-labeled TAQMAN® probe sequences were, designed using PRIMER EXPRESS™ software (Version 1.0, Applied Biosystems, Foster City, Calif.) or mFOLD™ software (now UNIFold™ software) (IDT, San Jose, Calif.). The $T_{m50}$ (the temperature at which only 50%, of a nucleic acid species is hybridized to its complement) ranged from 58° C. to 60° C. for primers and 68° C. to 70° C. for the TAQMAN® probes, respectively.

In some embodiments, a detector probe sequence is positioned within the target-specific portions of the chimeric oligonucleotide probes exclusively, and in certain embodiments, the detector probe sequence corresponds to a 3' portion of the target-specific sequence of the first chimeric oligonucleotide probe and a 5' portion of the target-specific sequence of the second chimeric oligonucleotide probe.

Protocols and reagents for means of carrying out further 5'-nuclease assays are well known to one of skill in the art, and are described in various sources. For example, 5'-nuclease reactions and probes are described in U.S. Pat. Nos. 6,214,979 issued Apr. 10, 2001; 5,804,375 issued Sep. 8, 1998; 5,487,972 issued Jan. 30, 1996; and 5,210,015 issued May 11, 1993, all to Gelfand et al.

In various embodiments, a detection method can utilize any probe that can detect a nucleic acid sequence. In some configurations, a detector probe can be, for example, a TAQMAN® probe, a stem-loop molecular beacon, a stemless or linear beacon, a PNA MOLECULAR BEACON™ probe, a linear PNA beacon, non-FRET probes, SUNRISE®/AMPLIFLUOR® probes, stem-loop and duplex SCORPION™ probes, bulge loop probes, pseudo knot probes, cyclicons, MGB ECLIPSE™ probe, a probe complementary to a ZIPCODE™ sequence, hairpin probes, peptide nucleic acid (PNA) light-up probes, self-assembled nanoparticle probes, and ferrocene-modified probes as known by one of ordinary skill in the art. A detector probe having a sequence complementary to a detector probe hybridization sequence, such as a ZIPCODE™ sequence, a fluorophore and a mobility modifier can be, for example, a ZIPCHUTE™ probe supplied commercially by Applied Biosystems (Foster City, Calif.).

A detector probe nucleotide sequence (or its complement) can comprise from about 12 nucleotides up to about 50 nucleotides, from about 12 nucleotides up to about 30 nucleotides, or from about 15 nucleotides up to about 25 nucleotides.

Hybridization-based pullout (HBP) detection comprises a process where a nucleotide sequence complementary to at least a portion of the ligated product or an amplicon thereof, for example, an addressable sequence or another identifying portion, is bound or immobilized to a solid or particulate pullout support (see, e.g., U.S. Pat. No. 6,124,0920 to O'Neill et al., granted Sep. 26, 2000). The ligation reaction mixture or amplification mixture is exposed to the pullout support. The ligation product or an amplicon thereof, under suitable conditions, hybridizes with the support-bound sequences. The unbound components are removed, purifying the bound products. Bound products can be purified and detected using various methods set forth herein.

Label or Reporter: A "label" or "reporter," refers to a moiety or property that allows the detection of that with which it is associated. The label can be attached covalently or non-covalently. Examples of labels include fluorescent labels (including, e.g., quenchers or absorbers), colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like. Fluorescent labels can include dyes that are negatively charged, such as dyes of the fluorescein family including, e.g. FAM™ dye, HEX™ dye, TET™ dye, JOE™ dye, NAN and ZOE; or dyes that are neutral in charge, such, as dyes of the rhodamine family including, e.g., TEXAS RED® dye, ROX™ dye, R110, R6G, and TAMRA™ dye; or dyes that are positively charged, such as dyes of the CYANINE™ family including e.g., Cy™2 dye, Cy™3 dye, Cy™5 dye, Cy™5.5 dye and Cy™7 dye. FAM™ dye, HEX™ dye, TET™ dye, JOE™ dye, NAN, ZOE, ROX™ dye, R110, R6G, and TAMRA™ dyes are available from, e.g., Applied Biosystems (Foster City, Calif.) or Perkin-Elmer, Inc. (Wellesley, Mass.); TEXAS RED® dye is available from, e.g., Molecular Probes, Inc. (Eugene, Oreg.); and Cy™2 dye, Cy™3 dye, Cy™5 dye, Cy™5.5 dye and Cy™7 dye, and are available from, e.g., Amersham Biosciences Corp. (Piscataway, N.J.). In certain embodiments, the fluorescer molecule is a fluorescein dye and the quencher molecule is a rhodamine dye.

A label or reporter can comprise both a fluorophore and a fluorescence quencher. The fluorescence quencher can be a fluorescent fluorescence quencher, such as the fluorophore TAMRA™ dye, or a non-fluorescent fluorescence quencher (NFQ), for example, a combined NFQ-minor groove binder (MGB) such as an MGB ECLIPSE™ minor groove binder supplied by Epoch Biosciences (Bothell, Wash.) and used with TAQMAN™ probes (Applied Biosystems, Foster City, Calif.). The fluorophore can be any fluorophore that can be attached to a nucleic acid, such as, for example, FAM™ dye, HEX™ dye, TET™ dye; JOE™ dye, NAN, ZOE, TEXAS RED® dye, ROX™ dye, R110, R6G, TAMRA™ dye, Cy™2 dye, Cy™3 dye, Cy™5 dye, Cy™5.5 dye and Cy™7 dye as cited above as well as VIC® dye, NED™ dye, LIZ® dye, ALEXA, Cy™9 dye, and dR6G.

Further examples of labels include black hole quenchers (BHQ) (Biosearch), Iowa Black (IDT), QSY quencher (Molecular Probes), and Dabsyl and Dabcel sulfonate/carboxylate Quenchers (Epoch). Labels can also comprise sulfonate derivatives of fluorescein dyes, phosphoramidite forms of fluorescein, phosphoramidite forms of CY™5 (available for example from Amersham), intercalating labels such as ethidium bromide, and SYBR™ Green I dye and PICOGREEN™ dye (Molecular Probes).

In various embodiments, detection of fluorescence of a PCR assay can be by any method known to skilled artisans, and can include, for example, real time detection as described supra or end point detection. Detection of fluorescence can be qualitative or quantitative. Quantitative results can be obtained, for example, with the aid of a fluorimeter, for example a fluorimeter comprised by an integrated nucleic acid analysis system, such as, for example, an Applied Biosystems ABI PRISM™ 7900HT Sequence Detection System. Furthermore, quantitative results can be obtained in some configurations using a real-time PCR analysis as described supra. Some-non-limiting examples of protocols for conducting fluorogenic assays such as TAQMAN® assays, including analytical methods for performing quantitative assays, can be found in, publications such as, for example, "SNPLEX™ Genotyping System 48-plex", Applied Biosystems, 2004; "User Bulletin #2 ABI PRISM™ 7700 Sequence Detection System," Applied Biosystems 2001; "User Bulletin #5 ABI PRISM™ 7700 Sequence Detection System," Applied Biosystems, 2001; and "Essentials of Real Time PCR," Applied Biosystems (Foster City, Calif.). Fluorogenic PCR assays used in some configurations of the present teachings can be performed using an automated system, such as, for example, an ABI 7700 Sequence Detection System (Applied Biosystems).

In some embodiments, detection can be achieved using microarrays and related software such as the Applied Biosystems Array System with the Applied Biosystems 1700 Chemiluminescent Microarray Analyzer and other commercially available array systems available from Affymetrix, Agilent, Illumina, and NimbleGen, among others (see also Gerry et al., *J. Mol. Biol.* 292:251-62, 1999; De Bellis et al., *Minerva Biotec* 14:247-52, 2002; and Stears et al., *Nat. Med.* 9:140-45, including supplements, 2003).

Further method embodiments for detection of a ligated product where the ligated product comprises a promoter sequence, or a complement thereof, include combining the ligated product with at least one primer comprising a sequence complementary to a 3' primer-specific portion of the ligation product and a DNA polymerase, to form at least one first amplification reaction mixture; subjecting the first amplification reaction mixture to at least one cycle of amplification to generate at least one first amplification product comprising the promoter sequence; combining the first amplification product with an RNA polymerase and a ribonucleoside triphosphate solution comprising at least one of rATP, rCTP, rGTP, rUTP, aminoallyl-rUTP, or biotin-rUTP to form a transcription reaction mixture; contacting the transcription reaction mixture under suitable conditions to generate an RNA transcription product; and detecting the target nucleic acid by detection of the RNA transcription prOduct or a portion thereof. In certain embodiments, the polymerase is reverse transcriptase.

Exemplary RNA polymerases include, T7, T3, or SP6 RNA polymerase and exemplary promoters include the T7, T3, or SP6 promoters. The RNA transcription product or a portion thereof can be detected using an addressable sequence and can also be quantified. For example, aminoallyl-rUTP can be incorporated during, transcription and detecting the product thereof comprises contacting the RNA transcription product or a portion thereof with a fluorescent succinimide ester dye.

In certain embodiments of detecting ligated product where the ligated product comprises an addressable sequence and the addressable sequence comprises a hybridization capture sequence, the method comprises purifying the ligated product or an amplification product thereof by annealing the ligated product with a bridging oligonucleotide having sequence complementarity to the hybridization capture sequence and with a hybridization capture probe.

Enzymatically Active Mutants or Variants Thereof: The term "enzymatically active mutants or variants thereof" when used in reference to an enzyme such as a polymerase, ligase, nuclease, or the like, refers to a polypeptide derived from the corresponding enzyme that retains at least some of the desired enzymatic activity. Enzymatically active mutants or variants include fragments such as Klenow fragment, Stoffel fragment, or recombinantly expressed fragments, naturally-occurring mutants, mutants generated using mutagens, genetically engineered mutants, mutants due to amino acid insertions or deletions or due to nucleic acid nonsense, missense, or frameshift mutations, reversibly modified enzymes, splice variants, polypeptides having modifications such as altered glycosylation, disulfide bonds, hydroxyl side chains, and phosphate side chains, or crosslinking, and the like. Protocols for measuring enzymatic activity using an appropriate assay are known to one of ordinary skill in the art.

Single Nucleotide Polymorphism Detection: Single nucleotide polymorphism or "SNP," when used herein, refers to a variation in a single nucleotide in a genomic sequence. "SNP genotyping" when used herein refers to identifying a polymorphic nucleotide.

In some embodiments as shown in FIG. 5 at 503 together with 513, at least two first chimeric oligonucleotide probe species 501 and 511, and one corresponding second chimeric oligonucleotide probe 502 are designed to identify the nucleotide at the polymorphic site 517. At least one first chimeric oligonucleotide probe species comprises a base pair match to the polymorphic site (probe 501 at 503) and at least one first chimeric oligonucleotide probe species comprises a mismatch to the polymorphic site (probe 511 at 513). The nucleotide and/or the position of the match or mismatch on the probe for the 503/513 embodiment is at the 3'-terminal nucleotide position (57 of 503). In some embodiments, the target-specific portions of the at least two first chimeric oligonucleotide probe species have the same nucleotide sequence other than at the 3'-terminal nucleotide position.

Thus, in some embodiments relating to FIG. 5 at 503 together with 513, a set of chimeric oligonucleotide probes comprises: at least, two different species 501 and 511 of first chimeric oligonucleotide probe wherein the 3'-terminal nucleotide 57 of the species differ; and at least one second chimeric oligonucleotide probe 502.

In some embodiments relating to FIG. 5 at 503 together with 513, each species of first chimeric oligonucleotide probe comprises: a primer-specific portion 59 comprising an amplification primer nucleotide sequence; and a target-specific portion 53 and 55, the target-specific portion having complementarity to a 3' portion of a preselected sequence of a target nucleic acid for at least all but the 3'-terminal nucleotide 57, a length of 6 nucleotides to 44 nucleotides, and 3'-OH and 2'-OR groups on the 3'-terminal nucleotide, wherein R comprises H or $C_1$-$C_3$ alkyl.

In some embodiments relating to FIG. 5 at 503 together with 513, at least one second chimeric oligonucleotide probe 502 comprises, in a 5' to 3' direction: a target-specific portion 52 having a 5'-terminal nucleotide 56 comprising a 5'-phosphate group, complementarity to a 5' portion of the preselected sequence of the target nucleic acid, a length of 6 nucleotides to 44 nucleotides, at least one nucleotide analog at one of the six 3'-most nucleotides, wherein the nucleotide analog has enhanced affinity for base pairing as compared to a corresponding non-modified nucleotide, and a primer-specific portion 54 comprising an amplification primer nucleotide sequence.

In some embodiments relating to FIG. 5 at 503 together with 513, when the two different species of first chimeric oligonucleotide probe and the second chimeric, oligonucleotide probe are contacted with target nucleic acid under conditions suitable to allow annealing, the 5' phosphate group of the second chimeric oligonucleotide probe is positioned immediately adjacent to the 3' hydroxyl group of a species of first chimeric oligonucleotide probe having 3'-terminal nucleotide sequence complementarity to the target nucleic acid, such as for 503.

In some embodiments as shown in FIG. 5 at 503 together with 523, at least two second chimeric oligonucleotide probe species 502 and 512 and one corresponding first chimeric oligonucleotide probe 501 are designed to identify the nucleotide at the polymorphic site 519. At least one second chimeric oligonucleotide probe species comprises a base pair match to the polymorphic site (probe 502 at 503) and at least one second chimeric oligonucleotide probe species comprises a mismatch to the polymorphic site (probe 512, at 523). The nucleotide and/or the position of the match or mismatch on the probe for the 503/523 embodiment is at the 5'-terminal nucleotide position 56. In some embodiments, the target-specific portions of the at least two second chimeric oligonucleotide, probe species have the same nucleotide sequence other than at the 5'-terminal nucleotide position.

In some embodiments relating to FIG. 5 at 503 together with 523, a set of chimeric oligonucleotide, probes comprises: at least two different species 502 and 512 of second chimeric oligonucleotide probe wherein the 5'-terminal nucleotide 56 of the species differ and at least one first chimeric oligonucleotide probe 501.

In some embodiments relating to FIG. 5 at 503 together with 523, each species of second chimeric oligonucleotide probe comprises, in a 5' to 3' direction: a target-specific portion 52 or 58, the target-specific portion having a 5'-terminal nucleotide 56 comprising a 5'-phosphate group, complementarity to a 5' portion of the preselected sequence of the target nucleic acid for at least all but the 5'-terminal nucleotide 56, a length of 6 nucleotides to 44 nucleotides, and a primer-specific portion 54 comprising an amplification primer nucleotide sequence.

In some embodiments relating to FIG. 5 at 503 together with 523, at least one first chimeric oligonucleotide probe 501 comprises, in a 5' to 3' direction: a primer-specific portion 59 comprising an amplification primer nucleotide sequence; and a target-specific portion 53, the target-specific portion having complementarity to a 3' portion of a preselected sequence of a target nucleic acid, a length of 6 nucleotides to 44 nucleotides, at least one nucleotide analog at one of the six 5'-most nucleotides wherein the nucleotide analog has enhanced affinity for base pairing as compared to a corresponding non-modified nucleotide, and 3'-OH and 2'-OR groups on the 3'-terminal nucleotide, wherein R comprises H or $C_1$-$C_3$ alkyl.

In some embodiments relating to FIG. 5 at 503 together with 523, when the first chimeric oligonucleotide probe 501 and the two different species 502 and 512 of second chimeric oligonucleotide probe are contacted with target nucleic acid 515 under conditions suitable to allow annealing, the 3' hydroxyl group of the first chimeric oligonucleotide probe is positioned immediately adjacent to the 5' phosphate group of a species of second chimeric oligonucleotide probe having 5'-terminal nucleotide sequence complementarity to the target nucleic acid.

In some embodiments relating to FIG. 5 at 503 together with 513, parallel singleplex methods for identifying a polymorphic nucleotide 517 in a target nucleic acid 515 comprise (1) contacting the target nucleic acid 515 with at least one chimeric oligonucleotide probe set for a time and under conditions suitable to form annealed product; (2) contacting the annealed product with a polypeptide having double-strand dependent ligase activity for a time and under conditions suitable to form ligated product; and (3) identifying the polymorphic nucleotide in the target nucleic acid.

In some embodiments relating to FIG. 5 at 503 together with 523, parallel singleplex methods for identifying a polymorphic nucleotide 519 in a target nucleic acid 515 comprise (1) contacting the target nucleic acid with at least one chimeric oligonucleotide probe set for a time and under conditions suitable to form annealed product; (2) incubating the annealed product with a polypeptide having double-strand dependent ligase activity for a time and under conditions suitable to form ligated product; and (3) identifying the polymorphic nucleotide in the target nucleic acid.

In some embodiments, multiplex methods for identifying a plurality of polymorphic nucleotides in a plurality of target nucleic acids comprise (1) contacting the plurality of target nucleic acids with a plurality of chimeric oligonucleotide probe sets for a time and under conditions suitable to form annealed product; (2) contacting the annealed product with a polypeptide having double-strand dependent ligase activity for a time and under conditions suitable to form ligated product; and (3) identifying the plurality of polymorphic nucleotides in the plurality of target nucleic acids by detecting the ligated product.

In some SNP detection embodiments, identifying comprises parallel singleplex and multiplex embodiments relating to FIG. 5. For embodiments of polymorphic nucleotide detection, when ligated product containing a first species of chimeric oligonucleotide probe is more readily detected than ligated product containing a second species of Chimeric oligonucleotide probe, the polymorphic nucleotide of the target nucleic acid is the complement of the 3'-terminal nucleotide of the first species; when ligated product containing the first species of chimeric oligonucleotide probe is detected in an equal amount to the ligated product containing the second species of chimeric oligonucleotide probe, the individual from whom the target nucleic acid was obtained is heterozygous at the SNP locus being evaluated; and when ligated product containing the first species of chimeric oligonucleotide probe is less readily, detected than ligated product containing the second species of chimeric oligonucleotide probe, the polymorphic nucleotide of the target nucleic acid is the complement of the 3'-terminal nucleotide of the second species.

In some embodiments, a plurality of species of first chimeric oligonucleotide probe and a plurality of species of second chimeric oligonucleotide probe may be contacted with target nucleic acid for identifying a polymorphic nucleotide. Labels specific to each species are detected for identification of ligated products, thereby identifying a polymorphic nucleotide.

In certain, embodiments, methods for identifying a polymorphic nucleotide comprise differentiating products based on melting temperature, wherein a ligated product with the higher melting temperature possesses the nucleotide of the matched species of chimeric oligonucleotide probe. In addition, the ligated product with the higher melting temperature can be isolated using methods known to one of ordinary skill in the art.

Kits: A "kit," as used herein, refers to a combination of at least some items for performing a ligation-enhanced nucleic acid detection assay embodiment. Embodiments of kits comprise, for example, a set of chimeric oligonucleotide probes as set forth herein. The set of chimeric oligonucleotide probes can be custom made. In some embodiments, kits comprise species of first chimeric oligonucleotide probe and/or species of second chimeric oligonucleotide probe together with corresponding, downstream or upstream probes for detecting one or more polymorphisms.

Embodiments of kits can further comprise a polypeptide having double-strand dependent ligase activity, a ligase buffer comprising ATP and $Mg^{++}$, a single-strand specific ribonuclease, a protease, or combinations thereof.

Embodiments of kits can further comprise first and second amplification primers having sequence complementarity to the primer-specific portions of first chimeric oligonucleotide probe and to at least one second chimeric oligonucleotide probe, respectively; a detector probe; an RNA or a DNA control target nucleic acid; reagents for sample collection; reagents for isolating nucleic acid; an RNA polymerase or an enzymatically active mutant or variant thereof; a DNA polymerase or an enzymatically active mutant or variant thereof; deoxyribonucleotides dATP, dCTP, dGTP, or, dTTP; or ribonucleotides rATP, rCTP, rGTP, rUTP, aminoallyl-rUTP, or biotin-rUTP. In certain kit embodiments, amplification primers are attached to a solid support such as a microarray.

Kits can include, for example, a control set of chimeric oligonucleotide probes, a control, target nucleic acid, nucleic acid amplification reagents such as a reverse transcriptase, primers suitable for reverse transcription and first strand and second strand DNA synthesis to produce a target amplicon, a detector probe, a thermostable DNA-dependent DNA polymerase and free deoxyribonucleotide triphosphates. In some embodiments, the enzyme comprising reverse transcriptase activity and thermostable DNA-dependent DNA polymerase activity are the same enzyme, e.g., *Thermus* sp. ZO5 polymerase or *Thermus thermophilus* polymerase.

In some embodiments, kits are provided for detecting degraded nucleic acids in a compromised sample, for determining nucleic acid quality in a compromised sample, for producing a gene expression profile from a compromised sample, or for measuring gene expression within compromised samples.

The container means of the kits will generally include at least one vial, test tube, flask, bottle, syringe or other packaging means, into which a component can be placed, and in some embodiments, suitably aliquoted. Where more than one component is included in the kit (they can be packaged together), the kit also will generally contain at least one second, third or other additional container into which the additional components can be separately placed. However, Various combinations of components can be packaged in a container means. The kits of the present teachings also will, typically include a means for containing the chimeric oligonucleotide probes, and any other reagent containers in close confinement for commercial sale. Such containers can include injection or blow-molded plastic containers into which the desired container means are retained. When the components of the kit are provided in one and/or more liquid solutions, the liquid solution comprises an aqueous solution that can be a sterile aqueous solution.

In certain embodiments, at least one kit component is provided as dried powder(s). When reagents and/or components are provided as a dry powder, the powder can be reconstituted by the addition of a suitable solvent. In certain embodiments, the solvent is provided in another container means. Kits can also comprise an additional container means for containing a sterile, pharmaceutically acceptable buffer and/or other diluent.

A kit can also include instructions for employing the kit components as well as the use of any other reagent not included in the kit. Instructions can include variations that can be implemented.

Embodiments of the present teachings can be further understood in light of the following examples, which should not be construed as limiting the scope of the present teachings in any way.

Example 1

Archived FFPE RNA is Fragmented

Samples were obtained from 1) frozen kidney tissue, 2) ambient-stored FFPE lung tissue blocks, and 3) ambient-stored FFPE colon tissue blocks. RNA from approximately 10 µm slices of the tissue samples was extracted and purified using the RECOVERALL® kit (Ambion Inc., Austin, Tex.). Total RNA from each sample (about 100 ng to 150 ng) was analyzed on an AGILENT® 2100 bioanalyzer (AGILENT® Technologies, Santa Clara, Calif.) using default parameters. Atypical level of detection for the AGILENT® bioanalyzer is about 0.1 ng/µl.

An analysis of RNA recovered from frozen kidney tissue is provided by FIG. 6A. An analysis of RNA recovered from ambient-stored FFPE lung tissue blocks and ambient-stored FFPE colon tissue block samples is provided by FIG. 6B and FIG. 6C, respectively. For the figures, the y-axis shows fluorescence intensity in relative units generated by dye binding to RNA, thus peak height is proportional to the amount of RNA. The x-axis depicts size in number of nucleotides which correlates with time from sample injection into the capillary as determined by using an internal standard. Frozen tissue samples demonstrated the profile of intact RNA, i.e., the 18S and 28S ribosomal RNAs are clearly evident (FIG. 6A). The FFPE samples demonstrated a profile of highly fragmented, small RNA that peaks early in the profile (FIG. 6B and FIG. 6C).

An integrity assay for determining RNA quality in FFPE samples is schematically shown in FIG. 7. The assay uses RT/PCR together with primer pairs (AB, AC, AD, AE) designed to amplify different sizes of products for analysis on the AGILENT® bioanalyzer. When the RNA quality is poor, the ability to amplify larger products is decreased. A comparison of results of integrity, assays for β-actin of a 2-year old FFPE colon sample as shown by FIG. 8A with a 13-year old FFPE colon sample as shown by FIG. 8B demonstrated that essentially no amplified product was detected in the older sample.

Example 2

Ligation-enhanced Nucleic Acid Detection Assay Protocol

The following Table 1 and Table 2 are referred to throughout the following examples.

TABLE 1

RNA Dilution Buffer

| | |
|---|---|
| 80% | Deionized formamide |
| 300 mM | Sodium acetate pH 6.4 |
| 100 mM | Sodium citrate pH 6.4 |
| 1 mM | EDTA |
| 5% | PEG 8000 |
| 100 ng/ml | E. coli RNA |

2X Hybridization Buffer

| | |
|---|---|
| 20% | Deionized formamide |
| 300 mM | Sodium acetate pH 6.4 |
| 100 mM | Sodium citrate pH 6.4 |
| 1 mM | EDTA |
| 5% | PEG 8000 |

10x Ligase Buffer

| | |
|---|---|
| 500 mM | Tris pH 7.0 |
| 100 mM | MgCl$_2$ |
| 100 mM | DTT |
| 10 mM | ATP |

RNase Cocktail (AMBION ® Inc., Austin, TX #2286)

| | |
|---|---|
| 0.5 U/µl | RNase A |
| 20 U/µl | RNase T1 |

10x Complete (SUPERTAQ ™, AMBION ® Inc., Austin, TX) Buffer

| | |
|---|---|
| 100 mM | Tris pH 9.0 |
| 500 mM | KCl |
| 15 mM | MgCl$_2$ |

TABLE 2

1. Total RNA sample is serially diluted with warmed (37° C.) RNA Dilution Buffer to a range of final concentrations (20 ng/µl, 2 ng/µl, 0.2 ng/µl and 0.02 ng/µl); each sample is heated to 65° C. for 5 minutes and then placed on ice.
2. A set of chimeric oligonucleotide probes are mixed and diluted to 50 fmol/µl (50 nM) each in nuclease-free water.
3. Hybridization Mix
   - 1.0 µl    Total RNA (dilutions from 1.)
   - 1.0 µl    Chimeric oligonucleotide probe set (50 fmol each from 2.)
   - 0.5 µl    E. coli RNA (1 µg/µl)
   - 2.5 µl    2x Hybridization Buffer (Table 1)

5.0 µl    total volume
   Heat sample to 95° C. for 3 minutes
   Centrifuge at 1000 rpm for 1 minute
   Incubate samples at room temperature (~20-25° C.) for 2 hr
4. Ligation/RNase Digestion Mix
   To
   - 5.0 µl    Hybridized mix from 3., add:
   - 2.5 µl    10x Ligase Buffer (Table 1)
   - 15.5 µl    nuclease-free water
   - 1.0 µl    T4 Rnl2 ligase (1 pmol)
   - 1.0 µl    RNase Cocktail (Table 1)

25.0 µl    total volume
   Mix well and centrifuge at 1000 rpm for 1 minute
   Incubate at room temp (20-30° C.) for 30 minutes
5. RNase Inactivation and Reverse Primer Binding
   Mix on ice:
   - 3.0 µl    nuclease-free water
   - 1.0 µl    Proteinase K (20 µg/µl)
   - 1.0 µl    Reverse (i.e., second) primer (10 µM)*

5.0 µl
   Add 5.0 µl of above mix to the 25 µl reaction from 4.
   Mix well and incubate at 75° C. for 15 minutes
   Spin 1000 rpm for 1 minute
6. One-step quantitative real time PCR Assay:
   Mix on ice:
   - 5.0 µl    Sample from 5. (1/6th of total)
   - 2.5 µl    10x Complete (SUPERTAQ ®) Buffer (Table 1.)

TABLE 2-continued

- 2.0 µl    dNTP mix (the mix contains each dNTP at a concentration of 2.5 mM)
- 1.0 µl    For/Rev (i.e., first/second) PCR primers (10 µM each)*
- 0.5 µl    5x ROX internal dye reference (INVITROGEN ™, Carlsbad, CA)
- 1.0 µl    detector probe (TAQMAN ® probe, 2 µM)*
- 0.2 µl    RNase inhibitor protein (4 units) (SUPERASIN ®, AMBION ® Inc., Austin, TX)
- 0.2 µl    SUPERTAQ ® (5 U/µl) (AMBION ® Inc., Austin, TX)
- 0.1 µl    reverse transcriptase (200 U/µl) (ARRAYSCRIPT ™, AMBION ® Inc., Austin, TX)
- 12.5 µl    nuclease-free water 25.0 µl    total
Reaction Conditions:
One cycle at 42° C. for 15 minutes followed by one cycle for 95° C. for 10 minutes
Then, 40 cycles of: 95° C. for 15 seconds followed by 60° C. for 40 seconds.

*The forward (first) and reverse (second) primers, and the detector probe (TAQMAN ® probe) sequence are designed as described by the examples.

Example 3

Standard qRT-PCR vs. Ligation-Enhanced Nucleic Acid Detection for β-Actin mRNA in Archived Tissue RNA from the 2-yr old and 13-yr old FFPE colon tissue samples depicted by FIG. 8A and FIG. 8B was used to compare standard qRT-PCR to ligation-enhanced nucleic acid detection embodiments for limits of detection of the β-actin mRNA target nucleic acid. RNA from approximately 10 µm slices of the tissue blocks was extracted and purified using the RECOVERALL® kit (Ambion Inc., Austin, Tex.). Total RNA from each sample was serially diluted with RNA Dilution Buffer (Table 1).

This study of standard qRT-PCR versus embodiments of ligation-enhanced nucleic acid detection essentially compares the ability of PCR to amplify the "target region" of a target nucleic acid using primers that have sequence complementarity to sequences that are upstream and downstream of that "target region" with the ability of PCR to amplify the "target region" as represented, by a ligated product and using primers that are specific for the primer portions of the ligated product. The primer portions of the ligated products do not have sequence complementarity to the target nucleic acid.

For the standard real-time PCR assay, the primers were designed based on sequences that are upstream and downstream of the "target region" of the target so that a small product of about 60-100 bp is amplified of which 25 base pairs represent the target-specific portion or "target footprint." Since the detector probe (TAQMAN®) probe) sequence used in this study is designed to be complementary to the target-specific portion of the target; the same detector probe (TAQMAN®) probe) was used for both the standard qRT-PCR assay and the ligation-enhanced nucleic acid detection embodiment.

A set of exemplary chimeric oligonucleotide probes having deoxyribonucleotides, 2'O-methyl nucleotide analogs and ribonucleotides was designed for detection of β-actin mRNA target nucleic acid as follows:
β-actin mRNA detection:
1$^{st}$ Chimeric oligonucleotide, probe: 5'-GCTCACCT-TAACGTAGAGTCTGCuaggauGGCAAG-3' (SEQ ID NO:1), and
2$^{nd}$ Chimeric oligonucleotide probe: 5'PO$_4$-GGACUUCcuguaaTATTGTTGGGGTAGTCGGACCT-3' (SEQ ID NO: 2)

Uppercase letters with no underlining: Deoxyribonucleotides
Lowercase letters: 2'O-methyl nucleotide analogs
Underlined uppercase letters: Unmodified ribonucleotides For this exemplary set of chimeric oligonucleotide probes, the deoxyribonucleotides of the first and second, probes represent a 5' primer-specific portion and a 3' primer-specific portion of the first and second probes, respectively. The primer-specific portions are designed not to anneal to the target nucleic acid but instead are designed to anneal to amplification primers added for a RT-PCR-detector probe (TAQ-MAN® probe) assay. The nucleotide analog region (lowercase letters) and the non-modified ribonucleotide region (uppercase underlined letters) together represent the target-specific portion of each probe. The set of chimeric oligonucleotide probes was diluted to a concentration of 50 fmol/µl in nuclease-free water.

The first and second PCR primers and the detector probe (TAQMAN® probe) have the following nucleotide sequences:
β-actin mRNA Nucleic Acid Target Detection:
First PCR primer: 5'-GCTCACCTTAACGTAGAGTCTGC-3' (SEQ ID NO:3);
Second PCR primer: 5'-AGGTCCGACTACCCCAA-CAATAT-3' (SEQ ID NO:4);
TAQMAN® probe: 5'FAM™ dye-TAGGATG-GCAAGGGA-MGB-Q-3' (SEQ ID NO:5).

Each reaction was performed in quadruplicate.

Results comparing standard qRT-PCR (open bars) for detection of β-actin mRNA to embodiments of ligation-enhanced nucleic acid detection (\\\\) for detection of the same target nucleic acid for 2-yr old and 13-yr old archived FFPE colon samples are provided by FIG. 9A and FIG. 9B. The data of FIG. 9A demonstrate that the two assays appear comparable in detection efficacy for β-actin mRNA target nucleic acid for the 2-year old sample. In contrast, the data of FIG. 9B demonstrate that the ligation-enhanced nucleic acid detection assay embodiment is more sensitive in detecting RNA by about 6-9 threshold cycles as compared to the level of RNA detected by standard qRT-PCR for the 13-year old sample.

Further FFPE archived tissue samples designated D1 (from breast tissue), D2, and D3 (both D2 and D3 are of unknown tissue type) were analyzed for RNA as for Example 1 and using the assays of Example 3 for the β-actin target nucleic acid. The bioanalyzer tracings shown in FIG. 10A, FIG. 10B, and FIG. 10C (for samples D1, D2, and D3, respectively) demonstrate that these samples are compromised since essentially no amplified bands are present other than the PCR primer band at 38 base pairs.

Results comparing detection of β-actin mRNA by qRT-PCR to detection by this embodiment of the ligation-enhanced nucleic acid detection assay for the D1, D2, and D3 archived FFPE samples are provided by FIG. 10D, FIG. 10E, and FIG. 10F, respectively. The data of each figure demonstrate that the qRT-PCR assay (open bars) essentially fails to amplify signal from the tissues while this illustrative ligation-enhanced nucleic acid detection assay embodiment (\\\\) detects target nucleic acid.

Example 4

Standard qRT-PCR vs. Ligation-Enhanced Nucleic Acid Detection for Detection of Various Target Ribonucleic Acids in FFPE-Archived Colon Tissue Samples from archived 14-year old FFPE colon tissue blocks were used to compare traditional qRT-PCR to one embodiment of ligation-enhanced nucleic acid detection assay for detection of three target nucleic acids, β-actin, glyceraldehyde-3-phosphate dehydrogenase (GAPDH), and transferrin receptor (TFRC) mRNAs. RNA from approximately 10 µm slices of the tissue blocks was extracted and purified using the RECOVERALL® kit (Ambion Inc., Austin, Tex.). Total RNA was serially diluted with RNA Dilution Buffer as set forth by the protocol of Table 2.

The set of chimeric oligonucleotide probes for detection of β-actin mRNA is described in Example 3. Illustrative chimeric oligonucleotide probe sets having deoxyribonucleotides, 2'O-methyl nucleotide analogs and ribonucleotides were designed for detection of human glyceraldehyde-3-phosphate dehydrogenase (GAPDH) mRNA and for detection of human transferrin receptor (TFRC) mRNA as follows.
GAPDH mRNA Target Nucleic Acid Detection:
1st Chimeric oligonucleotide probe:
5'-GCTCACCTTAACGTAGAGTCTGCggcugg CGACGC-3' (SEQ ID NO:6), and
2nd Chimeric oligonucleotide probe:
5'PO$_4$-AAAAGAAgaugcgTATTGTTGGGGTAGTCGGACCT-3' (SEQ ID NO:7).
TFRC mRNA Target Nucleic Acid Detection:
1st Chimeric oligonucleotide probe:
5'-GCTCACCTTAACGTAGAGTCTGCucagug GCACCA-3' (SEQ ID NO:8), and
2nd Chimeric oligonucleotide probe:
5'PO$_4$-ACCGAUCcaaaguTATTGTTGGGGTAGTCGGACCT-3' (SEQ ID NO:9).
Uppercase letters with no underlining: Deoxyribonucleotides
Lowercase letters: 2'O-methyl nucleotide analogs
Underlined uppercase letters: Unmodified ribonucleotides The deoxyribonucleotides of the first and second chimeric oligonucleotide probes represent a 5' primer-specific portion and a 3' primer-specific portion of the first and second probes, respectively. The nucleotide analog region (lowercase letters) and the non-modified ribonucleotide region (uppercase underlined letters) together represent the target-specific portion of each probe.

Standard real-time PCR primers were designed based on GAPDH and TFRC sequences that are upstream and downstream of the "target region" of the target nucleic acids so that a small product of about 80 bp was amplified of which 25 base pairs represented the target-specific portion or "target footprint." The detector probe (TAQMAN® probe) sequences shown below were designed to be complementary to the GAPDH or the TFRC target-specific portion, respectively; the same detector probe (TAQMAN® probe) was used for both the standard qRT-PCR assay and the ligation-enhanced nucleic acid detection assay embodiment for each target:
GAPDH TAQMAN® probe: VIC® dye-CTGGCGACG-CAAAA-BHQT™ dye-MGB (SEQ ID NO:10); and
TFRC TAQMAN® probe: VIC® dye-TCAGTGGCAC-CAACC-BHQ™ dye-MGB (SEQ ID NO:11).

The ligation-enhanced nucleic acid detection protocol was followed as for Example 3 using the first and second probe-specific primers cited therein. Results comparing standard qRT-PCR to this ligation-enhanced nucleic acid detection assay embodiment for detection of β-actin mRNA for archived FFPE samples presented by FIG. 11A demonstrate that the ligation-enhanced nucleic acid detection assay embodiment (\\\\) is more sensitive than qRT-PCR (open bars) since the threshold cycle for detection is 11 to 13 cycles lower.

Results comparing qRT-PCR to this exemplary ligation-enhanced nucleic acid detection assay for detection of GAPDH mRNA for archived FFPE, samples presented by FIG. 11B demonstrate that this ligation-enhanced nucleic acid detection assay embodiment (\\\\) is more sensitive by ~10-fold (~3 Ct's) as compared to the level of detection by standard qRT-PCR (open bars).

Results comparing qRT-PCR to this ligation-enhanced nucleic acid detection assay embodiment for detection of TFRC mRNA for archived FFPE samples presented by FIG. 11C demonstrate that the ligation-enhanced nucleic acid detection assay embodiment (\\\\) is at least as sensitive and, at lower concentrations of RNA, more sensitive by ~10-fold (~3 Ct's) as compared to the level of detection by standard qRT-PCR (open bars).

The ability to detect targets using both the standard qRT-PCR assay and the ligation-enhanced assay embodiment appears to differ with the particular target. Different target nucleic acids respond differently in terms of detection levels and in terms of cycle threshold differentials to both assays. Such different responses can be due to different RNA stability between targets or to behavior of RNAs in compromised samples, for example.

Example 5

Effect of Length of Nucleotide Analog Regions within Target-Specific Portions of Chimeric Oligonucleotide Probes Exemplary chimeric oligonucleotide probes designed to anneal with the target nucleic acid human β-glucuronidase (GUSB) mRNA were also designed to have either 0, 2, 4, 6, 8 or 10 contiguous 2'-O-methyl nucleotides within each target-specific portion proximal to each respective primer-specific portion as follows.

GUSB First Chimeric Oligonucleotide Probe:
5'-GCTCACCTTAACGTAGAGTCTGC
GUACCACACCCA-OH-3' (SEQ ID NO:12)
5'-GCTCACCTTAACGTAGAGTCTGCgu
ACCACACCCA-OH-3' (SEQ ID NO:13)
5'-GCTCACCTTAACGTAGAGTCTGCguac
CACACCCA-OH-3' (SEQ ID NO:14)
5'-GCTCACCTTAACGTAGAGTCTGCguacca
CACCCA-OH -3' (SEQ ID NO:15)
5'-GCTCACCTTAACGTAGAGTCTGCguaccaca
CCCA-OH -3' (SEQ ID NO:16)
5'-GCTCACCTTAACGTAGAGTCTGCguaccacaccCA-OH -3' (SEQ ID NO:17)
GUSB Second Chimeric Oligonucleotide Probe:
5'-[PO4]
GCCGACAAAAUGCTATTGTTGGGGTAGTCGGACCT -3' (SEQ ID NO:18)
5'-[PO4]
GCCGACAAAAUgcTATTGTTGGGGTAGTCGGACCT -3' (SEQ ID NO:19)
5'-[PO4]
GCCGACAAAaugcTATTGTTGGGGTAGTCGGACCT -3' (SEQ ID NO:20)
5'-[PO4]
GCCGACAaaaugcTATTGTTGGGGTAGTCGGACCT -3' (SEQ ID NO:21)
5'-[PO4]
GCCGAcaaaaugcTATTGTTGGGGTAGTCGGACCT -3' (SEQ ID NO:22)
5'-[PO4]
GCCgacaaaaugcTATTGTTGGGGTAGTCGGACCT-3' (SEQ ID NO:23)

Uppercase letters with no underlining: Deoxyribonucleotides
Lowercase letters: 2'O-Methyl nucleotide analogs
Underlined uppercase letters: Ribonucleotides Exemplary first and second chimeric oligonucleotide probes were designed similarly for β-actin mRNA, which target-specific portion is set forth in Example 3.

Following ligation, the ligated product contain a total of 0, 4, 8, 12, 16 or 20 2'-O-methyl nucleotides in two distal regions of the target-specific portion of the ligated product. Chimeric oligonucleotide probe sets (50 fmole each) were mixed with various amounts of synthetic target RNA (0-1×10$^{10}$ copies) having a length of 25 ribonucleotides (the length of the target-detection region) and carried through the protocol of Table 2. Each reaction was performed in quadruplicate.

QRT-PCR results using the exemplary GUSB chimeric oligonucleotide probes are provided by FIG. 12A and for the β-actin chimeric oligonucleotide probes in FIG. 12B. Increasing the number of 2'-O-methyl nucleotides in the probes decreased the Ct values for both probe sets. A decrease in Ct value reflects a greater ability to detect target.

The data of FIG. 12A and FIG. 12B demonstrate that, probes having six nucleotide analogs within each of the first and second probes proximal to each primer-specific portion appear to provide the least amount of background while providing desired detection. As the number of nucleotide analogs was increased beyond six, background appears to increasingly contribute to loss of specificity. As the number of nucleotide analogs was decreased to below six, efficacy of detection appears, to decrease.

Example 6

Single Nucleotide Polymorphism Detection

The ligation-enhanced nucleic acid detection assay is also useful for SNP detection. The set of GUSB first and second chimeric oligonucleotide probes of Example 5 having six nucleotide analogs proximal to each primer-specific portion was used in a test detection of a single nucleotide polymorphism present in two different locations of both a synthetic DNA target nucleic acid (total length=25 nucleotides) and a synthetic RNA target nucleic acid (total length=25 nucleotides).

The first test location for a single nucleotide polymorphism was termed SNP1 and the test nucleotide was positioned to be the 3'-terminal nucleotide of the target-specific portion of the first chimeric oligonucleotide probe. The SNP1 test position examined the differential ability of ligase to ligate a perfect match verses a mismatch at the 3'-terminal position of the first chimeric oligonucleotide probe when the probes were annealed to the target.

The second test location for a single nucleotide polymorphism was termed SNP2 and the test nucleotide was positioned to be the 5'-terminal nucleotide of the target-specific portion of the second chimeric oligonucleotide probe. The SNP2 test position examined the differential ability of ligase to ligate a perfect match verses a mismatch at the 5'-terminal position of the second chimeric oligonucleotide probe when the probes were annealed to the target.

The nucleotide sequence of the target-specific portions of the ligated product for GUSB target nucleic acid is shown below aligned with corresponding target nucleic acid, mismatched target nucleic acid SNP1, and mismatched target nucleic acid SNP2 sequences. For each sequence, the two nucleotides in bold represent the 3' nucleotide of the first chimeric oligonucleotide probe and the 5'-nucleotide of the second chimeric oligonucleotide probe, respectively. An, italicized nucleotide represents a base pair mismatch with the nucleotide sequence of the ligated product.
GUSB Ligated Product Showing Sequence of Target-Specific Portions:

```
       (SEQ ID NO: 24)  Primer-guacca
                        CACCCAGCCGACAaaaugc-Primer
                                     ↓↓
    DNA (SEQ ID NO: 25):    3' - CATGGTGTGGGTCGGCTGTTTTACG - 5'
SNP1 DNA (SEQ ID NO: 26):    3' - CATGGTGTGGGACGGCTGTTTTACG -
                                  5'
SNP2 DNA (SEQ ID NO: 27):    3' - CATGGTGTGGGTGGGCTGTTTTACG -
                                  5'
    RNA (SEQ ID NO: 28):    3' - CAUGGUGUGGGUCGGCUGUUUUACG- 5'
```

Single nucleotide polymorphisms and SNP-detector nucleotides are in bold text
SNP nucleotides are in italics In a further, study, the exemplary β-actin chimeric oligonucleotide probe set of Example 3, having six nucleotide analogs proximal to each primer-specific portion, was used in a test detection of a single nucleotide polymorphism present in two different locations of both a synthetic DNA target nucleic acid (total length=25 nucleotides) and a synthetic RNA target nucleic acid (total length=25 nucleotides).

The nucleotide sequence of the target-specific portions of the ligated product for β-actin target nucleic acid is shown below aligned with corresponding target nucleic acid, mismatched target nucleic acid SNP1, and mismatched target nucleic acid SNP2. For each nucleic acid sequence, the two nucleotides in bold represent the 3' nucleotide of the first chimeric oligonucleotide probe and the 5'-nucleotide of the second chimeric oligonucleotide probe, respectively. An italicized nucleotide represents a base pair mismatch with the nucleotide sequence of the ligated product.
Beta-Actin Ligated Product Showing Sequence of Target-Specific Portions:

```
       (SEQ ID NO: 29)  5'Primer-uaggau
                        GGCAAGGGACUUCcuguaa-Primer
                                     ↓↓
    DNA (SEQ ID NO: 30):    3' - ATCCTACCGTTCCCTGAAGGACATT - 5'
SNP1 DNA (SEQ ID NO: 31):    3' - ATCCTACCGTT GCCTGAAGGACATT -
                                  5'
SNP2 DNA (SEQ ID NO: 32):    3' - ATCCTACCGTTCGCTGAAGGACATT -
                                  5'
    RNA (SEQ ID NO: 33):    3' - AUCCUACCGUUCCCUGAAGGACAUU - 5'
```

Single nucleotide polymorphisms and SNP-detector nucleotides are in bold text
SNP nucleotides are in italics For each of the GUSB SNP target nucleic acid and the β-actin SNP target nucleic acid studies, the set of chimeric oligonucleotide probes was diluted to a concentration of 50 fmol/μl in nuclease-free water. For comparison, the studies were carried out separately with and without the addition of the RNase cocktail. The first and second PCR primers were as for Example 3. The detector probe (TAQMAN® probe) for β-actin SNP target nucleic acid was as for Example 3. The detector probe (TAQMAN® probe) for detection of GUSB SNP target nucleic acid had the sequence:
GUSB DETECTOR PROBE: 6FAM™ dye-TACCACAC-CCAGCCG-BHQ™ dye-MGB (SEQ ID NO:34).

Results regarding detection of SNP1 and SNP2 mismatched nucleic acids as compared to matched nucleic acids in both RNA and DNA β-actin nucleic acid targets are provided by FIG. 13A and FIG. 13B. The data of FIG. 13A demonstrated that without ligase or without target nucleic acid, no product is identified. Detection of matched nucleic acids was readily observed at a copy number of $1\times10^5$ and detection of DNA target nucleic acid occurred more readily than detection of RNA target nucleic acid. The mismatched β-actin target nucleic acid was not detected at that copy number. At a copy number of $1\times10^7$, the mismatched target nucleic acids were readily detected and were readily differentiated from matched target nucleic acids. A difference in cycle threshold of about 9.5 Ct's and 6.5 Ct's was observed between matched nucleic acids and the SNP1 mismatched nucleic acids and between matched nucleic acids and the SNP2 mismatched nucleic acids, respectively. The difference between the results with the SNP1 and SNP2 mismatched nucleic acids demonstrated that the more sensitive position for designing an SNP probe is for the mismatch to be positioned at the 3'-terminal nucleotide of the first chimeric oligonucleotide probe.

The data of FIG. 13B provide results of assays where RNase was not added to an embodiment of the ligation-enhanced SNP detection assay. Since the synthetic target nucleic acids in this study had a length equal to the length of the ligated product of the chimeric oligonucleotide probes, there were no single-stranded target nucleic acid ends to contribute lack of specificity. However, RNase removed ribonucleotide ends of probes that were not annealed and background signal was reduced. Without RNase, ligated products were detected even in the absence of target nucleic acid and absence of ligase, possibly due to non-specific ligation of non-duplexed single-stranded molecules or to formation of a duplex between the detector probe (TAQMAN® probe) and the single-stranded probes thereby providing amplification substrates. These results demonstrated a contribution of RNase to the SNP target nucleic acid detection embodiments.

Results regarding detection of SNP1 and SNP2 mismatched nucleic acids as compared to matched nucleic acids in both RNA and DNA GUSB nucleic acid targets are provided by FIG. 13C and FIG. 13D. The data of FIG. 13C demonstrated that without ligase or without target nucleic acid, no product was identified. Detection of matched nucleic acids was readily observed at a copy number of $1\times10^5$ and detection of DNA target nucleic acid occurred more readily than detection of RNA target nucleic acid. In contrast to the results with β-actin target nucleic acid embodiments, the SNP2 GUSB target nucleic acid was detected at that copy number. At a copy number of $1\times10^7$, the mismatched target nucleic acids were readily detected and a differential was observed in Ct between the SNP mismatched, target nucleic acid embodiments and matched target nucleic acid embodiments. Similar to the results for the β-actin target nucleic acid embodiments, the SNP1 mismatched target nucleic acid embodiment provided a greater Ct difference between matched target nucleic acids and mismatched target nucleic acids.

The data of FIG. 13D provide, results, of GUSB SNP target nucleic acid assay embodiments in the absence of RNase. The data of FIG. 13D indicated that RNase removed the ends of single-stranded chimeric oligonucleotide probes that are not annealed since background signal was reduced. Without RNase, ligated products were detected even in the absence of target nucleic acid and in the absence of ligase. A Ct differential for matched target nucleic acid verses mismatched nucleic acid was observed at a target nucleic acid copy number of $1\times10^7$, the same copy number as for the study with RNase.

The compositions, methods, and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Although the disclosed teachings have been described with reference to various applications, method's, and compositions, it will be appreciated that various changes and modifications can be made without departing from the teachings herein. The foregoing examples are provided to better illustrate the present teachings and are not intended to limit the scope of the teachings herein. Certain aspects of the present teachings can be further understood in light of the following claims.

What is claimed is:

1. A method for detecting a target nucleic acid in a sample, comprising:

a. contacting the sample with at least one set of chimeric oligonucleotide probes for a time and under conditions suitable to form an annealed product, wherein the at least one set of chimeric oligonucleotide probes comprises at least one first chimeric oligonucleotide probe and at least one second chimeric oligonucleotide probe;

wherein the at least one first chimeric oligonucleotide probe comprises, in a 5' to 3' direction:

a primer-specific portion comprising an amplification primer nucleotide sequence; and a target-specific portion, the target-specific portion having:

complementarity to a 3' portion of a preselected sequence of the target nucleic acid, a length of 6 nucleotides to 44 nucleotides, at least one nucleotide analog at one of the six 5'-most nucleotides wherein the nucleotide analog has enhanced affinity for base pairing as compared to a corresponding non-modified nucleotide, and 3'-OH and 2'-OR groups on the 3'-terminal nucleotide, wherein R comprises H or $C_1$-$C_3$ alkyl;

wherein the at least one second chimeric oligonucleotide probe comprises, in a 5' to 3' direction:

a target-specific portion having:

a 5'-terminal nucleotide comprising a 5'-phosphate group, complementarity to a 5' portion of the preselected sequence of the target nucleic acid, a length of 6 nucleotides to 44 nucleotides, and a primer-specific portion comprising an amplification primer nucleotide sequence;

wherein, when the at least one first and the at least one second chimeric oligonucleotide probes are annealed to the target nucleic acid, the 3' hydroxyl group of the first chimeric oligonucleotide probe is positioned immediately adjacent to the 5' phosphate group of the second chimeric oligonucleotide probe;

b. contacting the annealed product with a polypeptide having double-strand dependent ligase activity for a time and under conditions suitable to form a ligated product; and c. detecting the target nucleic acid in the sample by detecting the ligated product, or a surrogate thereof.

2. The method of claim 1, further comprising adding a single-strand specific ribonuclease prior to b, in or during b, or prior to c.

3. The method of claim 2, wherein the target nucleic acid is from a compromised sample.

4. The method of claim 2, wherein the target nucleic acid comprises DNA.

5. The method of claim 2, wherein the target nucleic acid comprises RNA.

6. The method of claim 5, wherein the RNA is siRNA or miRNA.

7. The method of claim 3, wherein the compromised sample comprises an FFPE sample.

8. The method of claim 2, wherein the polypeptide having double-strand dependent ligase activity comprises an RNA ligase and the RNA ligase comprises T4 Rnl2 ligase, DraRnl, KVP40 Rnl2, TbREL1, TbREL2, LtREL1, LtREL2, or an enzymatically active mutant or variant thereof.

9. The method of claim 8, wherein the RNA ligase comprises T4 Rnl2 ligase.

10. The method of claim 2, wherein the ligated product comprises an addressable sequence selected from a detector probe sequence or a hybridization capture sequence.

11. The method of claim 10, wherein the detector probe sequence comprises a 5'-nuclease probe sequence and the detector probe sequence includes a sequence that corresponds to a 3'-portion of the target-specific sequence of the first chimeric oligonucleotide probe taken together with a 5' portion of the target-specific sequence of the second chimeric oligonucleotide probe.

12. A method for detecting a target nucleic acid in a sample, comprising:

a. contacting the sample with at least one set of chimeric oligonucleotide probes for each target nucleic acid to be detected for a time and under conditions suitable to form an annealed product, wherein the at least one set of chimeric oligonucleotide probes comprises at least one first chimeric oligonucleotide probe and at least one second chimeric oligonucleotide probe;

wherein the at least one first chimeric oligonucleotide probe comprises, in a 5' to 3' direction:

a primer-specific portion comprising an amplification primer nucleotide sequence; and a target-specific portion, the target-specific portion having:

complementarity to a 3' portion of a preselected sequence of the target nucleic acid, a length of 6 nucleotides to 44 nucleotides, at least one nucleotide analog at one of the six 5'-most nucleotides wherein the nucleotide analog has enhanced affinity for base pairing as compared to a corresponding non-modified nucleotide, and 3'-OH and 2'-OR groups on the 3'-terminal nucleotide, wherein R comprises H or $C_1$-$C_3$ alkyl;

wherein the at least one second chimeric oligonucleotide probe comprises, in a 5' to 3' direction:

a target-specific portion having:

a 5'-terminal nucleotide comprising a 5'-phosphate group, complementarity to a 5' portion of the preselected sequence of the target nucleic acid, a length of 6 nucleotides to 44 nucleotides, and a primer-specific portion comprising an amplification primer nucleotide sequence;

wherein, when the first and second chimeric oligonucleotide probes are annealed to the target nucleic acid, a gap of one or more nucleotides separates the 3' hydroxyl group of the first chimeric oligonucleotide probe and the 5' phosphate group of the second chimeric oligonucleotide probe;

b. contacting the annealed product with a polymerase and nucleotides for a time and under conditions suitable to fill the gap;

c. contacting the product of b with a polypeptide having double-strand dependent ligase activity for a time and under conditions suitable to form a ligated product; and d. detecting the target nucleic acid by detecting the ligated product, or a surrogate thereof.

13. A method for detecting a target nucleic acid in a sample, comprising:

a. contacting the sample with at least one set of chimeric oligonucleotide probes for a time and under conditions suitable to form an annealed product, wherein the at least one set of chimeric oligonucleotide probes comprises at least one first chimeric oligonucleotide probe and at least one second chimeric oligonucleotide probe;

wherein the at least one first chimeric oligonucleotide probe comprises, in a 5' to 3' direction:

a primer-specific portion comprising an amplification primer nucleotide sequence; and a target-specific portion, the target-specific portion having:

complementarity to a 3' portion of a preselected sequence of the target nucleic acid, a length of 6 nucleotides to 44 nucleotides, nucleotide analogs at six of the six 5'-most nucleotides wherein each nucleotide analog has enhanced affinity for base pairing as compared to a corresponding non-modified nucleotide, and 3'-OH and 2'-OR groups on the 3'-terminal nucleotide, wherein R comprises H or $C_1$-$C_3$ alkyl;

wherein the at least one second chimeric oligonucleotide probe comprises, in a 5' to 3' direction:

a target-specific portion having:

a 5'-terminal nucleotide comprising a 5'-phosphate group, complementarity to a 5' portion of the preselected sequence of the target nucleic acid, nucleotide analogs at six of the six 3'-most nucleotides wherein each nucleotide analog has enhanced affinity for base pairing as compared to a corresponding non-modified nucleotide, a length of 6 nucleotides to 44 nucleotides, and a primer-specific portion comprising an amplification primer nucleotide sequence;

wherein, when the at least one first and at least one second chimeric oligonucleotide probes are annealed to the target nucleic acid, the 3' hydroxyl group of the at least one first chimeric oligonucleotide probe is positioned immediately adjacent to the 5' phosphate group of the at least one second chimeric oligonucleotide probe, and wherein the target-specific portion of the at least one first chimeric oligonucleotide probe together with the target-specific portion of the at least one second chimeric oligonucleotide probe has a length of 15 nucleotides to 25 nucleotides;

b. contacting the annealed product with T4 Rnl2 ligase or an enzymatically active mutant or variant thereof, and with a single-strand specific ribonuclease, for a time and under conditions suitable to form a ligated product; and c. detecting the target nucleic acid by detecting the ligated product, or a surrogate thereof.

\* \* \* \* \*